United States Patent
Evans et al.

(10) Patent No.: US 11,478,466 B2
(45) Date of Patent: Oct. 25, 2022

(54) SMALL MOLECULE PROMOTING OSTEOBLAST DIFFERENTIATION

(71) Applicant: Cornell University, Ithaca, NY (US)

(72) Inventors: Todd Evans, Pelham, NY (US); Brandoch Cook, Armonk, NY (US); Shuibing Chen, Pelham, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 17/601,001

(22) PCT Filed: Apr. 1, 2020

(86) PCT No.: PCT/US2020/026204
§ 371 (c)(1),
(2) Date: Oct. 1, 2021

(87) PCT Pub. No.: WO2020/205989
PCT Pub. Date: Oct. 8, 2020

(65) Prior Publication Data
US 2022/0088003 A1    Mar. 24, 2022

Related U.S. Application Data

(60) Provisional application No. 62/827,454, filed on Apr. 1, 2019.

(51) Int. Cl.
*A61K 31/4709*    (2006.01)

(52) U.S. Cl.
CPC .................. *A61K 31/4709* (2013.01)

(58) Field of Classification Search
None
See application file for complete search history.

(56) References Cited

U.S. PATENT DOCUMENTS

2001/0021708 A1    9/2001    Wehner et al.
2010/0105696 A1    4/2010    Garcia-Echeverria et al.

OTHER PUBLICATIONS

Pubchem, Substance Record for SID 354891002, Mar. 12, 2018, 7 pages. https://pubchem.ncbi.nlm.nih.gov/substance/354891002.
Cook, B., et al., Discovery of a Small Molecule Promoting Mouse and Human Osteoblast Differentiation via Activation of p38 MAPK-Beta, Cell Chemical Biology, Apr. 25, 2019, vol. 26, 17 pages.

*Primary Examiner* — Heidi Reese
(74) *Attorney, Agent, or Firm* — Hodgson Russ LLP

(57) ABSTRACT

Provided are compositions and methods for promoting osteogenic differentiation of undifferentiated cells, such as stem cells. An example of a compound useful in the present method is 6,8-dimethyl-3-(4-phenyl-1H-imidazol-5-yl)quinolin-2(1H)-one (DIPQUO). The present methods can be used for treatment and prevention of bone disorders.

8 Claims, 22 Drawing Sheets

Specification includes a Sequence Listing.

D.

E.

F.

G.

H.

B.

F.

G.

SMALL MOLECULE PROMOTING OSTEOBLAST DIFFERENTIATION

CROSS-REFERENCE TO RELATED APPLICATIONS

This application claims priority to U.S. Provisional patent application No. 62/827,454, filed on Apr. 1, 2019, the disclosure of which is incorporated herein by reference.

BACKGROUND OF THE DISCLOSURE

Bone fracture is the most common impact injury requiring emergent medical care. Of over 6 million fractures annually in the United States, at least 5-10% do not properly resolve. Bone non-unions and other failures of healing are often caused and exacerbated by contributing factors, such as osteoporosis which can itself be affected by lifestyle factors including obesity and poor diet. These factors result in a substantial cost burden both in terms of palliative care and lost productivity. Recombinant human bone morphogenetic proteins (BMPs) including BMP-2 and BMP-7 have been approved for therapeutic use in long bone non-unions; however, wide-ranging and poorly understood effects of growth factor treatments, deleterious side effects revealed in patient studies, and expenses associated with production and scalability, limit their common application in clinical settings (Carragee et al., 2011; Fu et al., 2013; Vaccaro et al., 2008). Additionally, therapeutics developed to block osteoporotic bone resorption (Cosman et al., 2016) have recently been abandoned due to unacceptable risks (Mullard, 2016). Therefore, fracture healing is largely accomplished through a combination of mechanical intervention and natural repair over time, and effective osteoporosis therapeutics are still in the nascent stages. There is consequently an unmet need for pharmaceutically relevant compounds that can stimulate or accelerate bone regeneration and healing.

SUMMARY OF THE DISCLOSURE

In this disclosure, a high throughput screen is used to identify activators of the bone marker alkaline phosphatase (ALP), and discovered 6,8-dimethyl-3-(4-phenyl-1H-imidazol-5-yl)quinolin-2(1H)-one (DIPQUO). DIPQUO markedly promotes osteoblast differentiation, including expression of Runx2, Osterix, and Osteocalcin. Treatment of human mesenchymal stem cells with DIPQUO results in osteogenic differentiation including a significant increase in calcium matrix deposition. DIPQUO stimulates ossification of emerging vertebral primordia in developing zebrafish larvae, and increases caudal fin osteogenic differentiation during adult zebrafish fin regeneration. The stimulatory effect of DIPQUO on osteoblast differentiation and maturation was shown to be dependent on the p38 MAPK pathway. Inhibition of p38 MAPK signaling or specific knockdown of the p38-beta isoform attenuates DIPQUO induction of ALP, suggesting that DIPQUO mediates osteogenesis through activation of p38-beta, and is a promising lead candidate for development of bone therapeutics.

In an aspect, this disclosure provides a method for promoting and/or accelerating osteoblast differentiation and maturation by contacting undifferentiated cells with an effective amount of one or more activators of the bone marker alkaline phosphatase (ALP). The activator of bone ALP may be DIPQUO. In an embodiment, the present disclosure provides a method of treating or preventing bone disorder, or promoting bone regeneration, or alleviating the symptoms of bone disorder in a subject in need thereof comprising administering to the subject DIPQUO in an amount effective to treating or preventing bone disorder, or promoting bone regeneration, or alleviating the symptoms of bone disorder.

In an embodiment, this disclosure provides compositions comprising, consisting essentially of, or consisting of one or more agents that can activate bone alkaline phosphatase. In an embodiment, this disclosure provides compositions comprising, consisting essentially of, or consisting of DIPQUO. In an embodiment, DIPQUO is the only activator of bone alkaline phosphatase present in the composition. In an embodiment, the composition comprising DIPQUO may be free is any agent that can inhibit p38 MAPK signaling.

DETAILED DESCRIPTION OF THE DISCLOSURE

Figure 1:
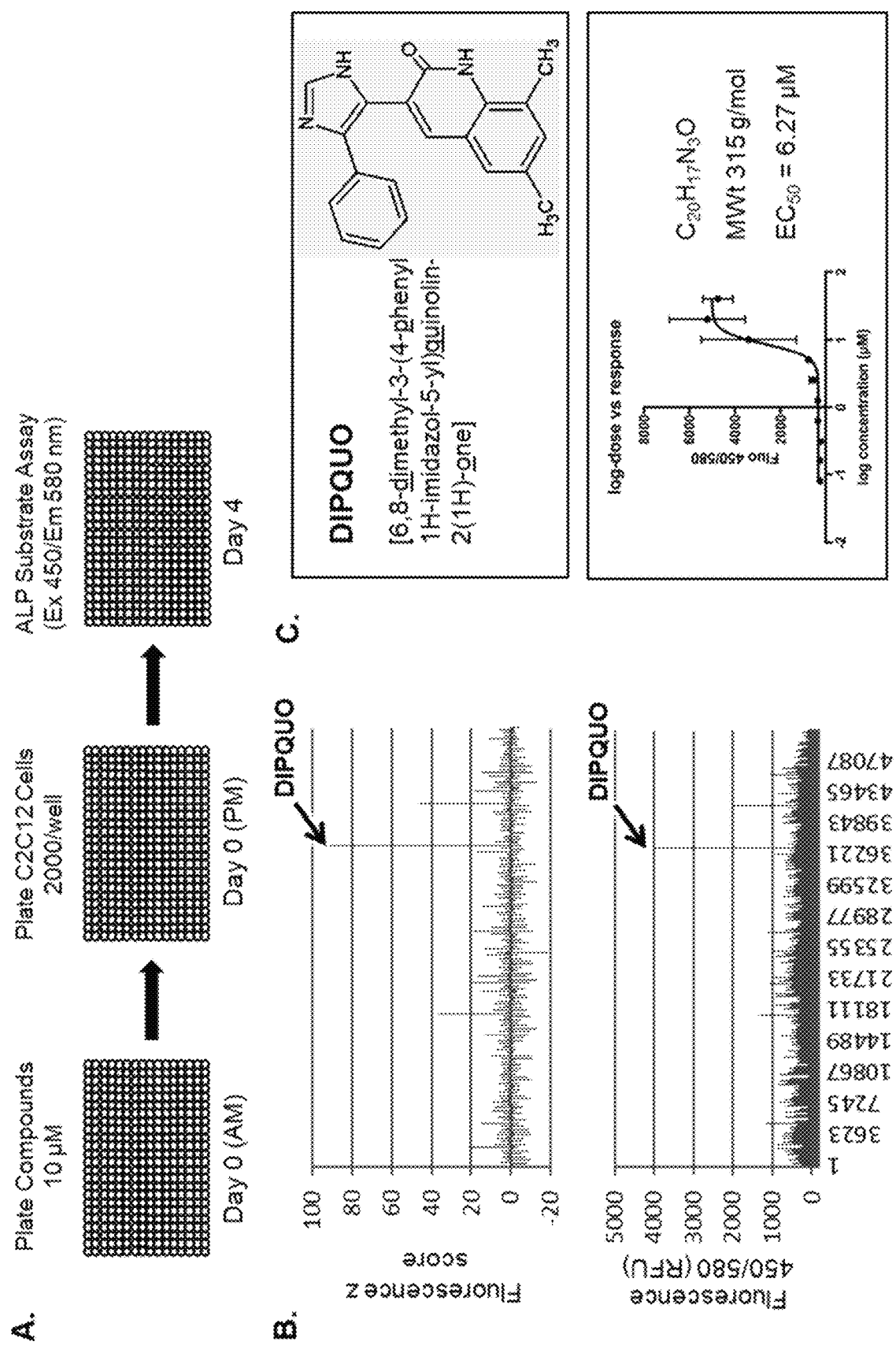
FIG. 1. A High-Throughput Screen for Activators of ALP Expression Identifies a Lead Hit Molecule DIPQUO (A) Screening workflow, with library compounds first plated onto 384-well clear-bottom plates. Next, C2C12 murine myoblasts were seeded at a density of 2,000/well and cultured for 4 days. Cells were lysed and analyzed for enzymatic digestion of fluorescent ALP substrate by automated measurement of fluorescence Ex/Em 450/580 nm. (B) Raw readings of 450/580 nm fluorescence for >47 k library compounds identified DIPQUO (labeled arrows) as clearly the strongest activator of ALP. This was confirmed by additional algorithmic comparison of fluorescence Z scores (B) and calculation of normalized percent activation (not shown). (C) Molecular structure of DIPQUO; measurement of half maximal effective concentration (EC50) was performed in triplicate using purchased re-synthesized powder (n=3). (D) Confirmation of activation of ALP expression by DIQPUO. C2C12 myoblasts were treated for 2 days with 10 mM DIPQUO and stained for ALP expression using alkaline naphthol and hematoxylin. Vehicle (DMSO) and inert structural analogs BT344 and BT345 were used as negative controls. Scale bars, 200 mm. (E) Flow cytometric analysis of ALP-positive C2C12 cell population. See also FIG. 7, Tables 1-6.
Figure 1:
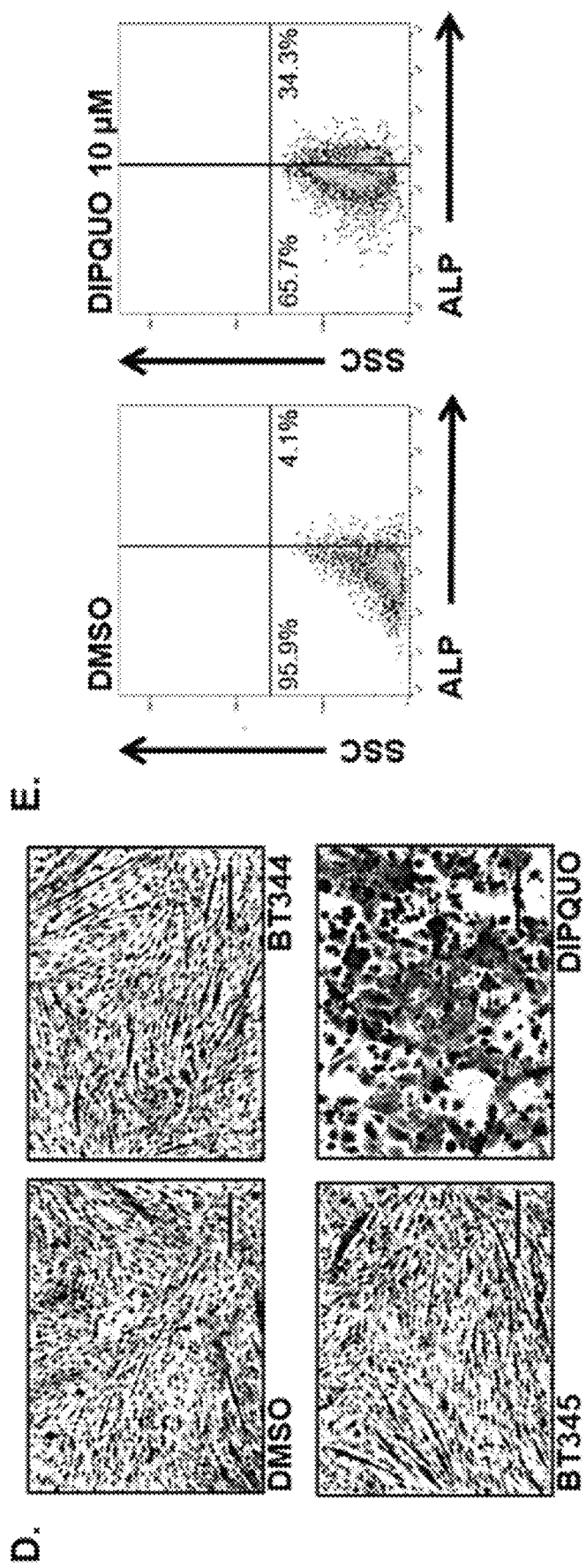

Although claimed subject matter will be described in terms of certain examples, other examples, including examples that do not provide all of the benefits and features set forth herein, are also within the scope of this disclosure. Various structural, logical, and process step changes may be made without departing from the scope of the disclosure.

Every numerical range given throughout this specification includes its upper and lower values and includes every value within those ranges to the tenth decimal place of the lowest value in the range, as well as every narrower numerical range that falls within it, as if such narrower numerical ranges were all expressly written herein.

All nucleotide sequences described herein, their RNA and DNA equivalents, and complimentary sequences are included in this disclosure. All polynucleotide and amino acid sequences associated with GenBank accession numbers (or other similar databases) described in this disclosure are incorporated herein by reference as those sequences are listed in the database as of the priority filing date of this application or patent.

The terms "a" or "an" are intended to include the singular as well as the plural of the particular item being referenced. Any reference to a singular includes its plural and vice-versa.

The term "treatment" refers to reduction in one or more symptoms or features associated with the presence of the particular condition being treated. Treatment does not necessarily mean complete cure, nor does it preclude recurrence or relapses. For example, the present disclosure provides a method for preventing or treating bone disorders or alleviating one or more symptoms of bone disorder or dysfunction—all of which are considered as "treatment"—comprising administering to an individual in need of treatment, a therapeutically effective amount of a composition disclosed herein.

The term "therapeutically effective amount" as used herein is the amount sufficient to achieve, in a single or multiple doses, over any period of time, the intended purpose of treatment.

In an aspect, this disclosure provides a method for promoting and/or accelerating osteoblast differentiation and maturation in vitro comprising contacting progenitor or undifferentiated cells with an effective amount of one or more activators of the bone marker alkaline phosphatase (ALP). In an embodiment, this disclosure provides a method for promoting and/or accelerating osteoblast differentiation and maturation in vitro comprising contacting progenitor or undifferentiated cells (such as stem cells) with an effective amount of DIPQUO.

In an aspect, this disclosure provides a method of promoting and/or accelerating osteoblast differentiation and maturation in a subject in need thereof comprising administering to the subject an amount of DIPQUO effective to promote and/or accelerate osteoblast differentiation and maturation. While not intending to be bound by any particular theory, it is considered that DIPQUO may function mechanistically to promote activation of the beta isoform of p38 MAP kinase.

In an embodiment, this disclosure provides a method of treating or preventing bone disorder or alleviating the symptoms of bone disorder in a subject in need thereof comprising administering to the subject DIPQUO in an amount effective to treat or alleviate the symptoms of the bone disorder.

In an embodiment, this disclosure provides compositions comprising, consisting essentially of, or consisting of one or more agents that can activate bone alkaline phosphatase. In an embodiment, this disclosure provides compositions comprising, consisting essentially of, or consisting of DIPQUO. In an embodiment, DIPQUO is the only activator of bone alkaline phosphatase present in the composition. In an embodiment, the composition does not contain an inhibitor of p38 MAP kinase.

The structure of DIPQUO is shown below:

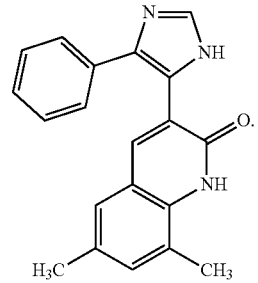 [SMILES: Cc1cc(C)c2[nH]c(=O)c(-c3[nH]cnc3-c3ccccc3)cc2c1]

In examples, a composition may comprise a compound having the following structure:

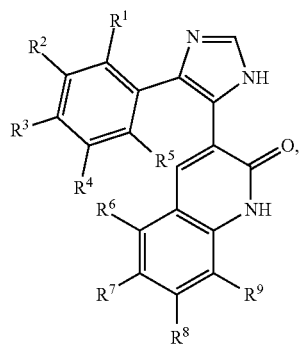

where $R^1$, $R^2$, $R^3$, $R^4$, $R^5$, $R^6$, $R^7$, $R^8$, and $R^9$ are individually at each occurrence chosen from —H, alkyl groups (e.g., linear alkyl groups such as, for example, methyl groups, ethyl groups, propyl groups, and the like and branched alkyl groups, such as, for example isopropyl groups, isobutyl groups, tert-butyl groups, neo-pentyl groups, isopentyl groups, and the like), and halogens (e.g., —I, —Cl, —Br, or —F). The compound may be a salt, a partial salt, a hydrate, a polymorph, an isomer (e.g., a structural or stereoisomer), or a mixture thereof. The compounds may have stereoisomers.

A composition may further comprise dimethylsulfoxide (DMSO), Tween-80, or a combination thereof. A composition comprising DMSO, Tween-80, and a composition may comprise DMSO and Tween-80 in a 1:1 ratio. A composition comprising a 1:1 mixture of DMSO and Tween-80 retains solubility and activity of the compound. A composition may be formed by taking a solution of a compound in DMSO (e.g., 10 mM DIPQUO solution in DMSO) and diluting the solution into an equal volume of Tween-80. In an illustrative example, a 1 mL of a DMSO solution comprising the compound may be diluted into 1 mL of Tween-80.

In an embodiment, the compounds or compositions of the present disclosure may be used for in vitro or ex vivo expansion of stem cells (e.g., pluripotent stem cells), such as mesenchymal stem cells (e.g., human mesenchymal stem cells) and coaxing of the cells toward osteogenic cell lineages. The method comprises contacting undifferentiated cells (e.g., stem cells) with the compounds (such as DIPQUO) of the present disclosure and upon generation of osteogenic cells, introducing or reintroducing (in the case of autologous cells) into the subject. For example, stem cells may be obtained from peripheral blood, umbilical cord blood, or bone marrow, and contacted with DIPQUO ex vivo and then reintroduced into the host. This method may be used on a subject who has a condition or is undergoing treatment adversely affecting bones, such as for example, a subject who is undergoing chemotherapy, a subject having or who has had or is going to have radiation therapy, a subject having aplastic anemia, and/or a subject having myelodysplasia, or any other condition or treatment affecting the bones.

In an embodiment, the present disclosure provides a method to prevent, treat, improve or and/or alleviate a bone disorder comprising administering to a subject in need thereof DIPQUO in an amount sufficient to prevent, treat, improve or and/or alleviate a bone disorder. Examples of bone disorders include, but are not limited to osteoporosis, rickets, osteomalacia, osteogenesis imperfecta, marble bone disease (osteopetrosis), fibrous dysplasia, Paget's Disease, hyperparathyroidism, hyperthyroidism, rheumatoid arthritis, Gorham-Stout disease, McCune-Albright syndrome, osteolytic metastases of various cancers or multiple myeloma. Bone disorders also include any loss of bone mass, reduced bone mineral density or slowing down of bone regeneration such as that associated with general bone fragility, joint degeneration, non-union fractures, orthopedic and dental problems, dental work (such as dental implants) periodontal diseases, skeletal aging, broken bones, bone defects, bone transplant, bone grafts, bone cancer, joint replacements or repair In an embodiment, the present method may be used in conjunction with therapeutic treatments that involve administration of agents that result in bone loss. Examples of such therapeutic drugs include synthetic glucocorticoids (e.g., prednisone, dexamethasone), chemotherapeutic drugs or therapy (e.g., breast cancer drugs, e.g., aromatase inhibitors, anastrozole, letrozole, and exemestane, prostate cancer therapy, e.g., androgen deprivation), prostate hyperplasia (e.g., tamsulosin), diuretics (e.g., furosemide), anti-seizure or mood altering drugs (e.g., carbamazepine and phenytoin), thyroid hormone replacement (e.g., Synthroid), proton pump inhibitors (used for heart burn), and certain hypertension medications. Thus, in an embodiment, DIPQUO may be administered in conjunction with (overlapping or separately) with any of the treatments that result in or can result in bone loss, reduction in bone mineral density or delay of bone regeneration.

In an embodiment, the present compound and compositions may be used to inhibit bone resorption. For example, a composition comprising DIPQUO may be administered to a female subject undergoing menopause or who is pre or post-menopausal, or other subjects who have been immobilized for long periods of time (such as subjects who may be recovering from illness or accidents necessitating immobilization).

Therapeutically effective dosages of DIPQUO will vary from subject to subject, and will depend, among other things, upon the effect or result to be achieved, the specifics of the patient, the condition of the patient and the route of delivery. Identifying the right dosage is well within the purview of one skilled in the art (such as a clinician). Examples of DIPQUO dosages can be from about 0.01 µg/kg to about 100 mg/kg. Dosages can be from 0.1 µg/kg to about 50 mg/kg, or 0.1 µg/kg to about 10 mg/kg and all ranges and values therebetween.

Administration of present compounds or compositions can be carried out using any suitable route of administration known in the art. For example, the compositions may be administered via intravenous, intramuscular, intraperitoneal, subcutaneous, intra-articular, intrasynovial, oral, topical, or inhalation routes. The compositions may be administered parenterally or enterically. The compositions may be introduced as a single administration or as multiple administrations or may be introduced in a continuous manner over a period of time. For example, the administration(s) can be a pre-specified number of administrations or daily, weekly or monthly administrations, which may be continuous or intermittent, as may be clinically needed and/or therapeutically indicated. The treatment can be carried on as long as clinically needed and/or therapeutically indicated. In embodiments, the compounds or compositions of the present disclosure may be delivered to a subject in need thereof (e.g., at a location close to the site of need, e.g., fracture or bone deformity) using a medical device. For example, the compound or compositions may be delivered using orthopedic medical devices, such as, for example, sponges, dressing, gauges, stents, bone cement, or may be incorporated into materials used in artificial joints, pins, anchors, buttons, prostheses, screws, custom implants, plates that are used in orthopedic procedures.

The compounds of the present disclosure, or pharmaceutically acceptable salts thereof can be provided in pharmaceutical compositions for administration by combining them with any suitable pharmaceutically acceptable carriers, excipients and/or stabilizers. Examples of pharmaceutically acceptable carriers, excipients and stabilizer can be found in *Remington: The Science and Practice of Pharmacy* (2011) 21st Edition, Philadelphia, Pa. Lippincott Williams & Wilkins. For example, suitable carriers include excipients, or stabilizers which are nontoxic to recipients at the dosages and concentrations employed, and include buffers such as acetate, Tris, phosphate, citrate, and other organic acids; antioxidants including ascorbic acid and methionine; preservatives such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; and/or non-ionic surfactants such as Tween or polyethylene glycol (PEG). The pharmaceutical compositions may comprise other therapeutic agents.

The compounds or compositions of the present disclosure may be administered in any suitable form. For example, the DIPQUO or a composition comprising DIPQUO may be administered in the form of a tablet, capsule, pill, powder, paste, granules, elixir, solution, suspension, dispersion, gel, syrup, extended release forms, or any other form. The compounds (e.g., DIPQUO) may be delivered via liposomes, microparticles, microcapsules, nanoparticles or encapsulation, any other delivery means. The compounds (e.g., DIPQUO) may be delivered via nanobeads or via tissue engineering constructs (e.g., comprising suitable scaffold materials), which can provided extended release of the compound.

The subject treated with the compositions and methods of this disclosure can be a human subject or a non-human animal. The subject can be of any gender or age.

The following example is presented to illustrate the present disclosure. It is not intended to be limiting in any matter.

EXAMPLE 1

Bone differentiation and mineralization can be modeled in vitro using various cell culture platforms. The murine myoblast cell line C2C12 is bipotential and can be directed toward either muscle or bone progenitor fates (Fux et al., 2004; Katagiri et al., 1994), with the latter being assayed via expression of osteogenic markers, including alkaline phosphatase (ALP). Additionally, primary mesenchymal stem cells can be derived from stem and progenitor populations, and driven toward adipogenic, chondrogenic, or osteogenic fates using permissive cytokines (Huang et al., 2007; Jaiswal et al., 1997). The course of osteoblastogenic differentiation can be dissected in a stepwise manner, with early expression of the master regulator Runx2 controlling differentiation events associated with expression of Osterix and ALP. Activation of this program precipitates expression of later differentiation markers such as Osteocalcin (OCN), and finally signatures of terminal osteoblast differentiation that include increased expression of Sclerostin (Sost) and dentin matrix acidic phosphoprotein 1 (Dmp1), as well as extracellular matrix deposition and calcium release that can be measured with vital stains.

The C2C12 cell line provides a useful screening platform because of its bipotentiality, robust culture capacity, and adaptability to scalable and automated quantitative assays. In the present study, we performed with C2C12 cells a high-throughput screen of over 47,000 compounds, and identified a small molecule activator of ALP, 6,8-dimethyl-3-(4-phenyl-1H-imidazol-5-yl)quinolin-2(1H)-one (DIPQUO), which promotes and accelerates osteoblast differentiation and maturation in vitro and in vivo. Moreover, DIPQUO functions mechanistically to promote activation of the beta isoform of p38 MAP kinase, which places it in a unique niche as a research tool for models of skeletogenesis and as a lead hit candidate to optimize for potential therapeutic discovery.

Results

A High-Throughput Chemical Screen Identifies DIPQUO, a Small Molecule that Promotes Activation of Early Osteogenesis Marker ALP. To identify small-molecule activators of osteoblast differentiation, we measured ALP activity using a fluorescent emission assay as a reporter for enzymatic digestion of ALP substrate in lysates derived from C2C12 myoblasts. ALP is an established marker for conversion of the normally myogenic-biased C2C12 cells to the osteogenic lineage (Chen et al., 2004), and BMPs are known robust activators of ALP in C2C12 (Fux et al., 2004; Katagiri et al., 1994). Therefore, before screening, the assay was calibrated using recombinant human BMP4 protein as a positive control. Compounds were robotically deposited onto 384-well plates and then overlaid by C2C12 cells for a 4-day culture period, followed by lysis and fluorescent substrate assays (FIG. 1A; Table 1). To ensure uniformity, C2C12 cells were maintained in normal culture medium containing 10% fetal bovine serum, and lysis and substrate addition achieved using a microplate multidrop device. The primary screen (Table 2) encompassed greater than 47,000 small molecules tested at a final concentration of 10 µM. Primary hit candidates were identified in three separate subsets by setting the following thresholds: (1) raw fluorescence ratio (RFU)>800 (FIG. 1B), (2) Z score>10 (FIG. 1B), and (3) normalized percent activation (Malo et al., 2006)>5 (not shown), yielding a total of 52 compounds, with an approximately 0.1% hit rate. When primary hits were ranked according to RFU and Z score values (Tables 1 and 3), the clear top candidate was DIPQUO (FIG. 1C, note the highest peak in FIG. 1B). This was confirmed by secondary screening in a concentration response experiment of the initial hits, and by a final validation screen of four potential candidates (Table 4). Purity of DIPQUO was assayed by high-pressure liquid chromatography and mass spectrometry (Table 1), and half maximal effective concentration in C2C12 cells was measured to be 6.27 mM (FIG. 1C). In addition, DIPQUO was re-synthesized by a commercial supplier (ChemBridge) and carbon and proton NMR spectra were obtained to confirm the identity and purity.

Figure 7:
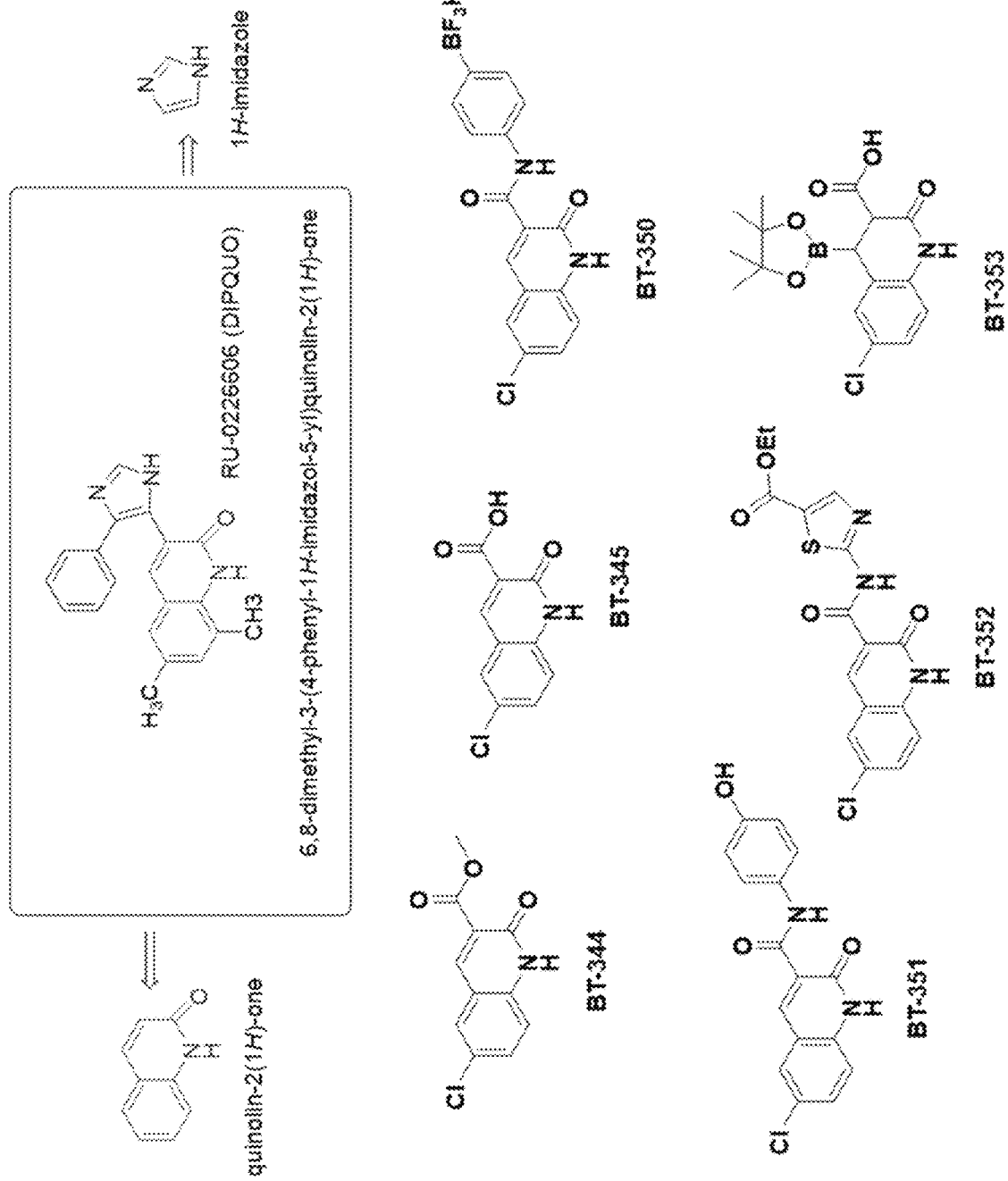
FIG. 7. Design of structural analogs. From initial screening to identify target-to-hit, we discovered the lead molecule RU-0226606 (DIPQUO). This molecule is comprised of quinolin-2(H)-one and 1H-imidazole. To accomplish SAR, we first focused on the quinolin-2(H)-one moiety to develop the 5 compounds shown. Detailed analytical data are reported in Table 5.

Following screening, the re-synthesized DIPQUO was tested in complementary cell-based assays. In C2C12 cells, DIPQUO treatment was found to rapidly stimulate ALP expression within 2 days, as visualized by the foci of bright purple staining shown in the bottom right panel of FIG. 1D. We carried out a structure activity relationship (SAR) study using several related compounds from the screening library and by synthesis of a small set of additional related compounds designed to probe either of two pharmacophores of which DIPQUO is comprised, imidazole and quinolinone (FIG. 7; Table 5 for relevant structures), which demonstrated specificity for DIPQUO in the ALP assay (Table 5). We therefore expanded the SAR study to probe a library of 154 structural chemical analogs assembled by ChemBridge from available screening library compounds. Analogs contained modifications around the quinolinone and imidazole moieties. Compounds were assigned unique identifiers and deposited on screening plates as described above. Compounds were tested for activation of ALP in C2C12 cells using conditions identical to the original screen, with the following exceptions: (1) analogs were tested in duplicate at final concentrations of 1, 5, and 10 µM and (2) DIPQUO, instead of recombinant BMP4, was used as a positive control. Table S6, for purposes of brevity, shows only data for 10 mM samples. Although there was no analog treatment that resulted in significant activation of ALP compared with DIPQUO, all compounds with greater than 10% activation were re-tested in ALP staining assays. All were confirmed to be inert, demonstrating striking specificity for DIPQUO osteogenic activity. Flow cytometry assays confirmed activation of ALP expression in >30% of the cell culture by day 2, which is significantly higher than the baseline of approximately 4% in DMSO-treated cells (FIG. 1E).

Figure 2:
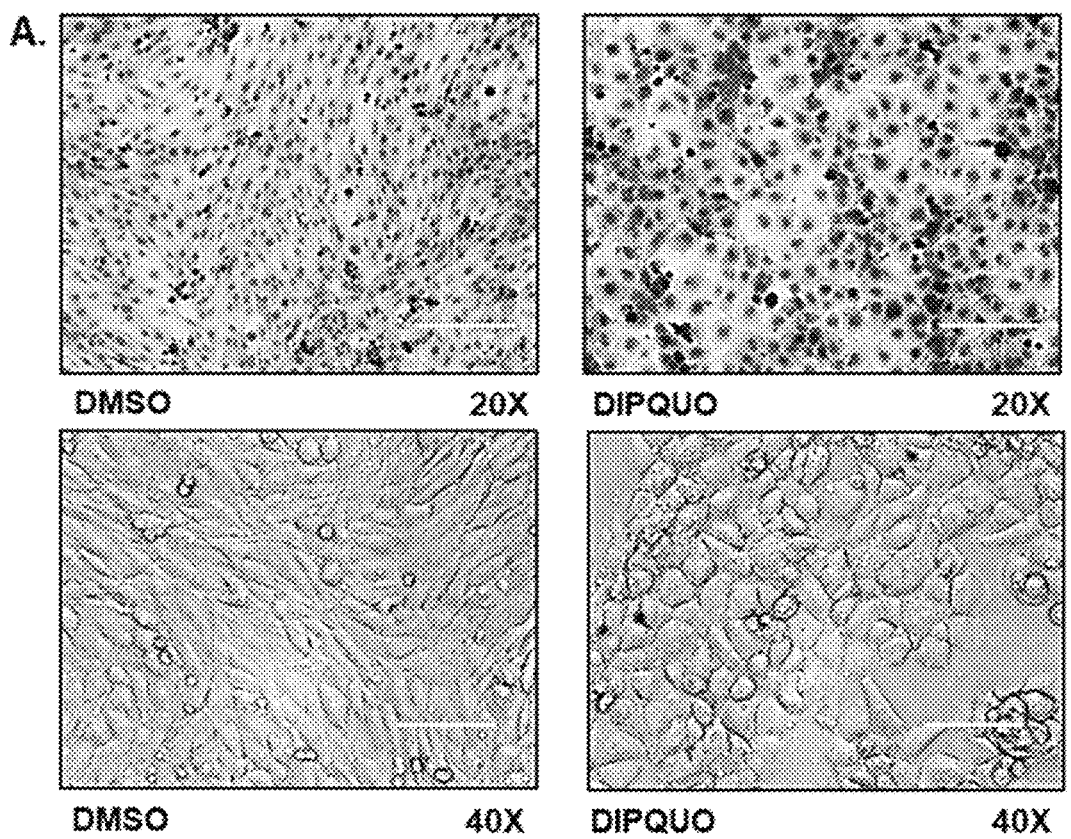
FIG. 2. Insulin-like Growth Factor 1 Protects Cell Survival during DIPQUO-Induced Osteogenesis (A) DIPQUO potentiates a rapid rearrangement of cellular morphology to a cuboidal phenotype. (B and C) Cell culture attrition over successive days (B) can be partially rescued by addition of human Insulin-like growth factor 1 (IGF-1) protein (C), which functions as an osteoblast survival factor. Scale bars, 200 mm (203ALP staining images) and 100 mm (403phase-contrast images) in (A) and 400 mm (ALP staining images) in (B and C).
Figure 2:
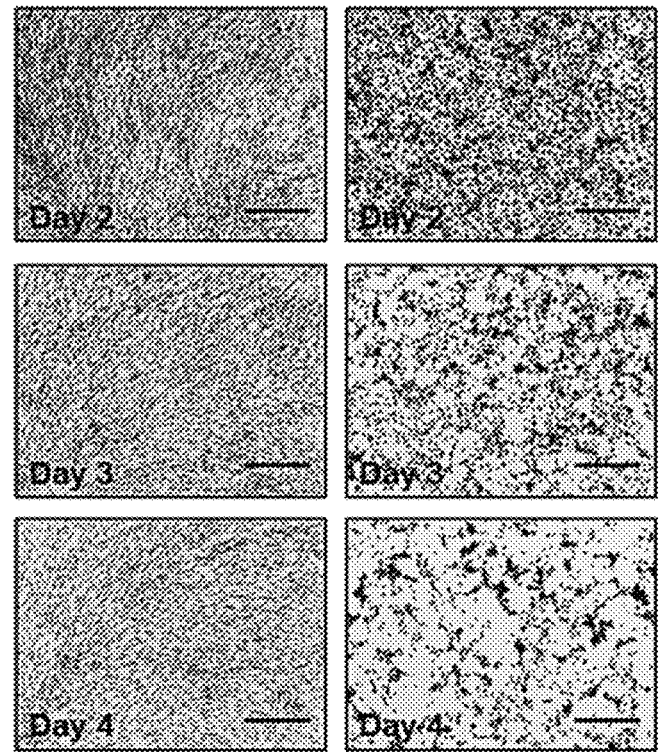
Figure 2:
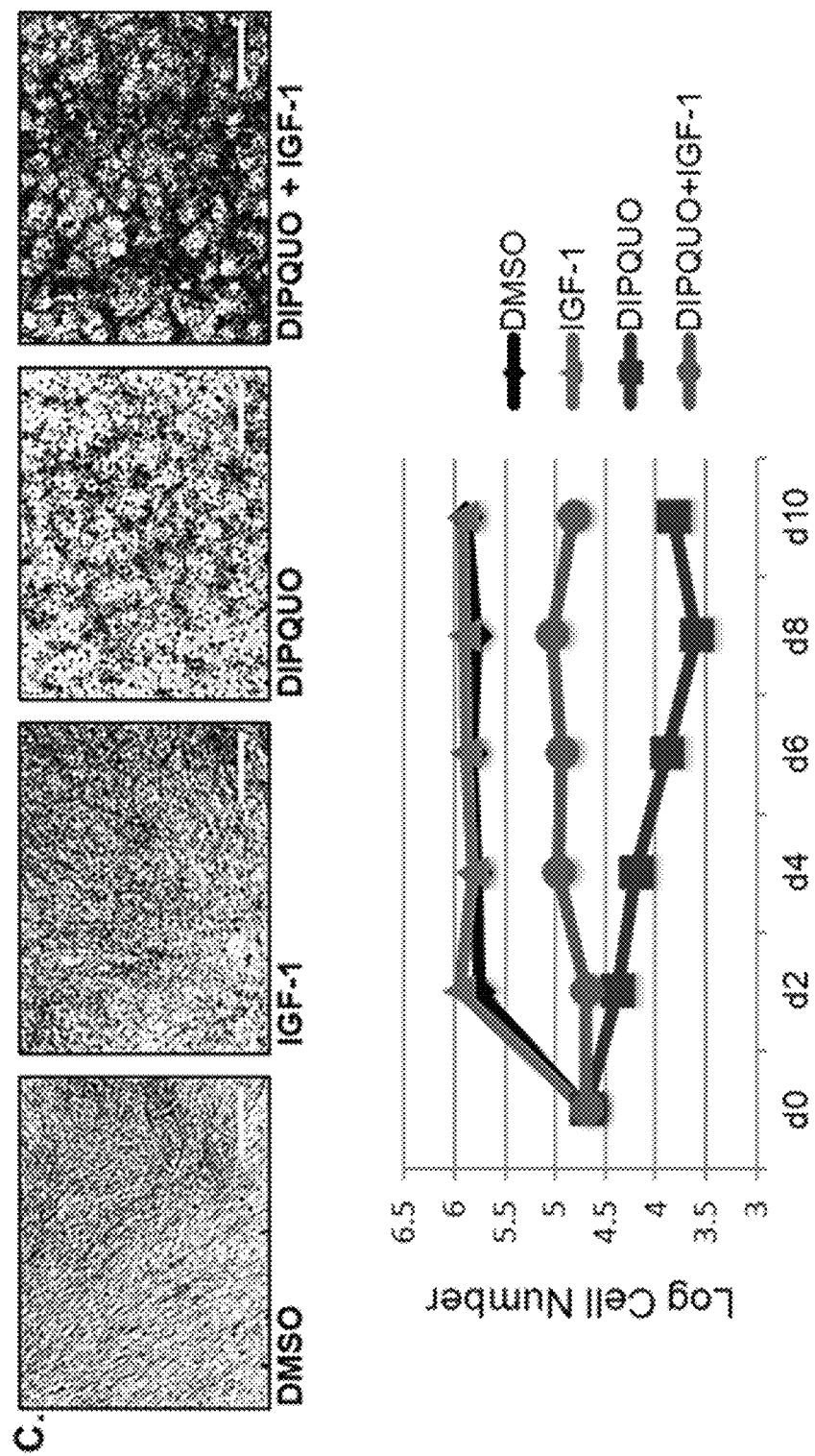

There was a marked difference in staining between DIPQUO treated cultures and those treated with DMSO or inert structural analog control molecules BT344 and BT345. In contrast to the screening strategy, which quantified day 4 substrate fluorescence, abbreviated 2-day treatment of C2C12 cells was optimal to resolve cell staining. DIPQUO treatment resulted in rapid rearrangement of cellular architecture from fibroblast-like to a cuboidal phenotype (FIG. 2A) that is a morphological hallmark of post-mitotic osteoblasts (Rutkovskiy et al., 2016). Continued treatment with 10 mM DIPQUO resulted in attrition of the C2C12 culture (FIG. 2B), which was partially rescued by addition of the osteoblast survival factor insulin-like growth factor 1 (FIG. 2C).

Figure 3:
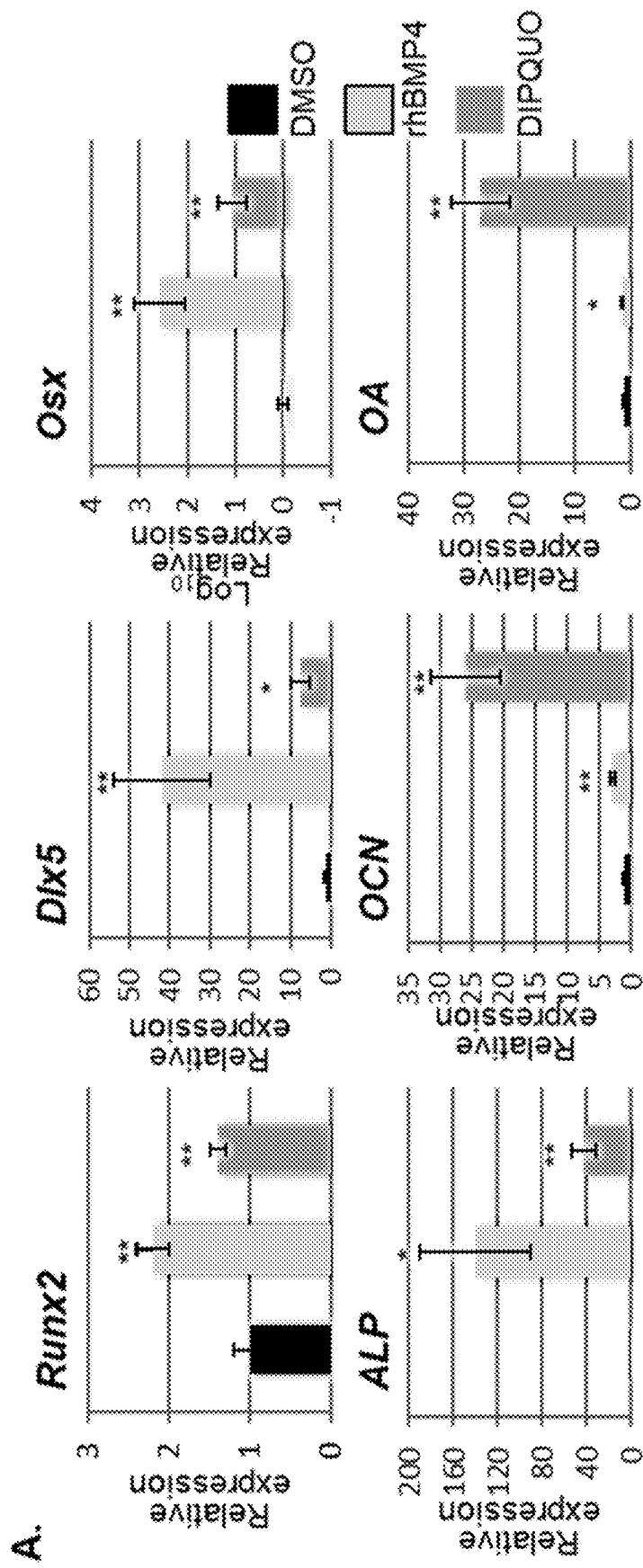
FIG. 3. DIPQUO Promotes Osteoblast Differentiation (A) qRT-PCR analysis of relative expression of transcripts indicates osteoblast differentiation, arranged from early differentiation markers through later ones denoting progress to osteoblast maturation. DIPQUO treatment was compared with BMP-treated cells, and values were normalized to DMSO-treated controls using Gapdh as a reference control (Runx2 n=6; Dlx5 n=3; Osx, ALP, and Osteoactivin [OA] n=5; OCN n=4). Error bar is ±SEM; *p<0.05, **p<0.01. (B) DIPQUO impacts regulation of gene sets involved in osteoblast differentiation and maturation. Ingenuity Pathway Analysis of day 2 RNA sequencing reads identified several subsets of genes that align with osteogenic differentiation and maturation processes (table). An expression heatmap reveals strong agreement between separate biological replicates that show a trend for upregulation by DIPQUO treatment of osteogenic genes and downregulation of antiosteogenic genes, compared with DMSO-treated controls. See also FIG. 8.
Figure 3:
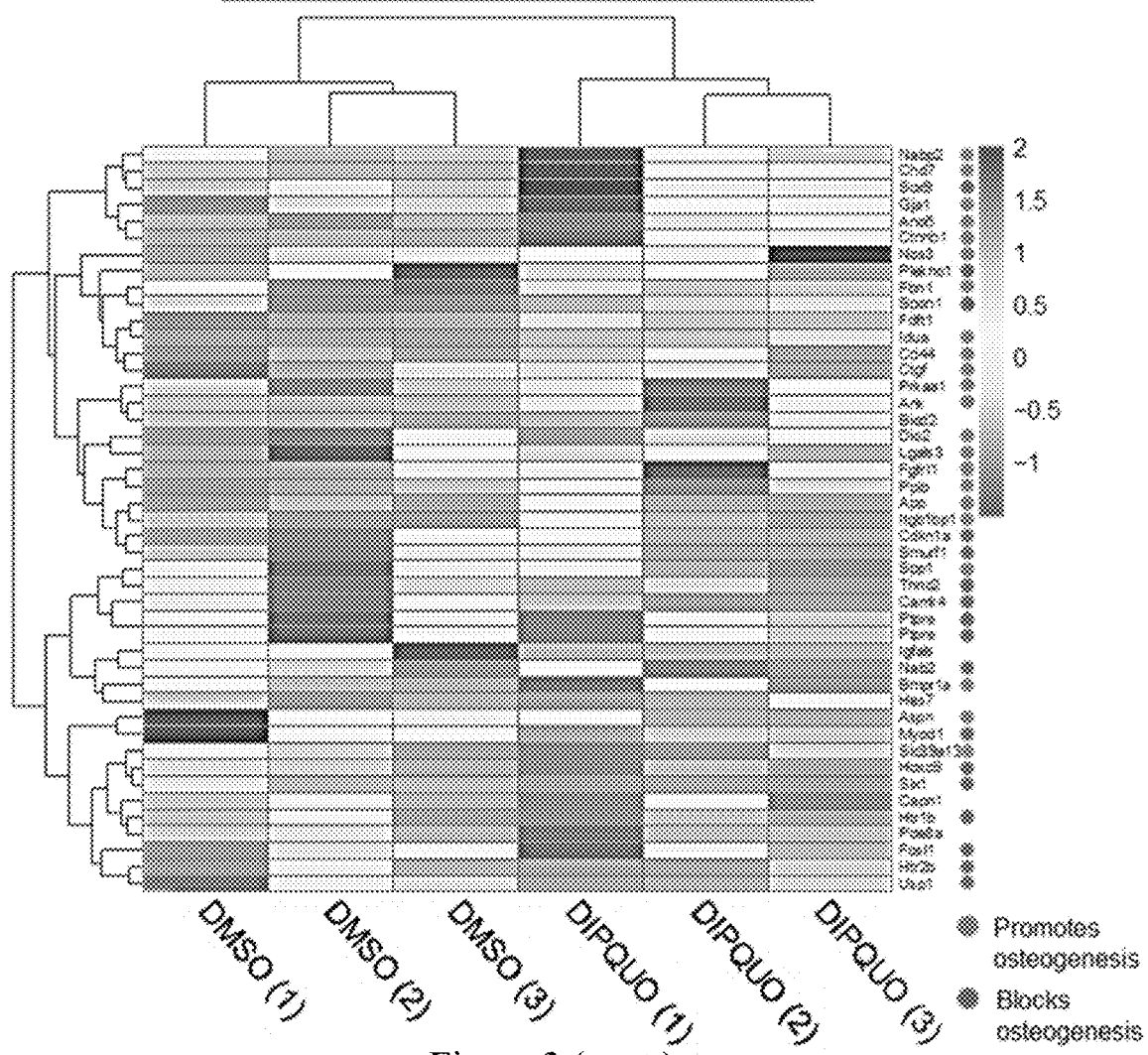

DIPQUO Differentiates Human Multipotent Progenitors toward Mature Osteoblast Fate. The robust and rapid activation of ALP in C2C12 cells after DIPQUO treatment prompted a more thorough investigation into osteoblast differentiation. Progenitor populations are known to acquire successively narrower commitment toward terminal osteoblast fate in a stepwise manner characterized by progressive expression of early, transitional, and finally mature osteoblast markers (Beederman et al., 2013; Rutkovskiy et al., 2016). A subset of these markers was measured by qRT-PCR, which showed that DIPQUO treatment of C2C12 cells resulted in significant upregulation of the master osteoblast regulator Runx2 and its immediate effector Osterix (Osx) (FIG. 3A). Notably, expression of markers associated with progressive differentiation and maturation, including ALP and OCN, respectively, were substantially increased by day 2 of DIPQUO treatment (FIG. 3A). These later-stage transcripts are not normally highly expressed during early stages of directed differentiation. Although ALP expression levels were higher in BMP-treated controls, the relative CT values were less variable in DIPQUO-treated samples (FIG. 3A). Moreover, changes in expression of later, maturation-associated transcripts OCN and Osteoactivin were much higher with DIPQUO treatment than in BMP-treated positive controls, suggesting a more robust and direct effect on osteoblast differentiation by DIPQUO. Finally, broad investigation of transcriptional programs via RNA sequencing and Ingenuity Pathway Analysis revealed several bone morphological and functional gene sets whose expression patterns correlated strongly with osteogenic activity (FIG. 3B).

Figure 4:
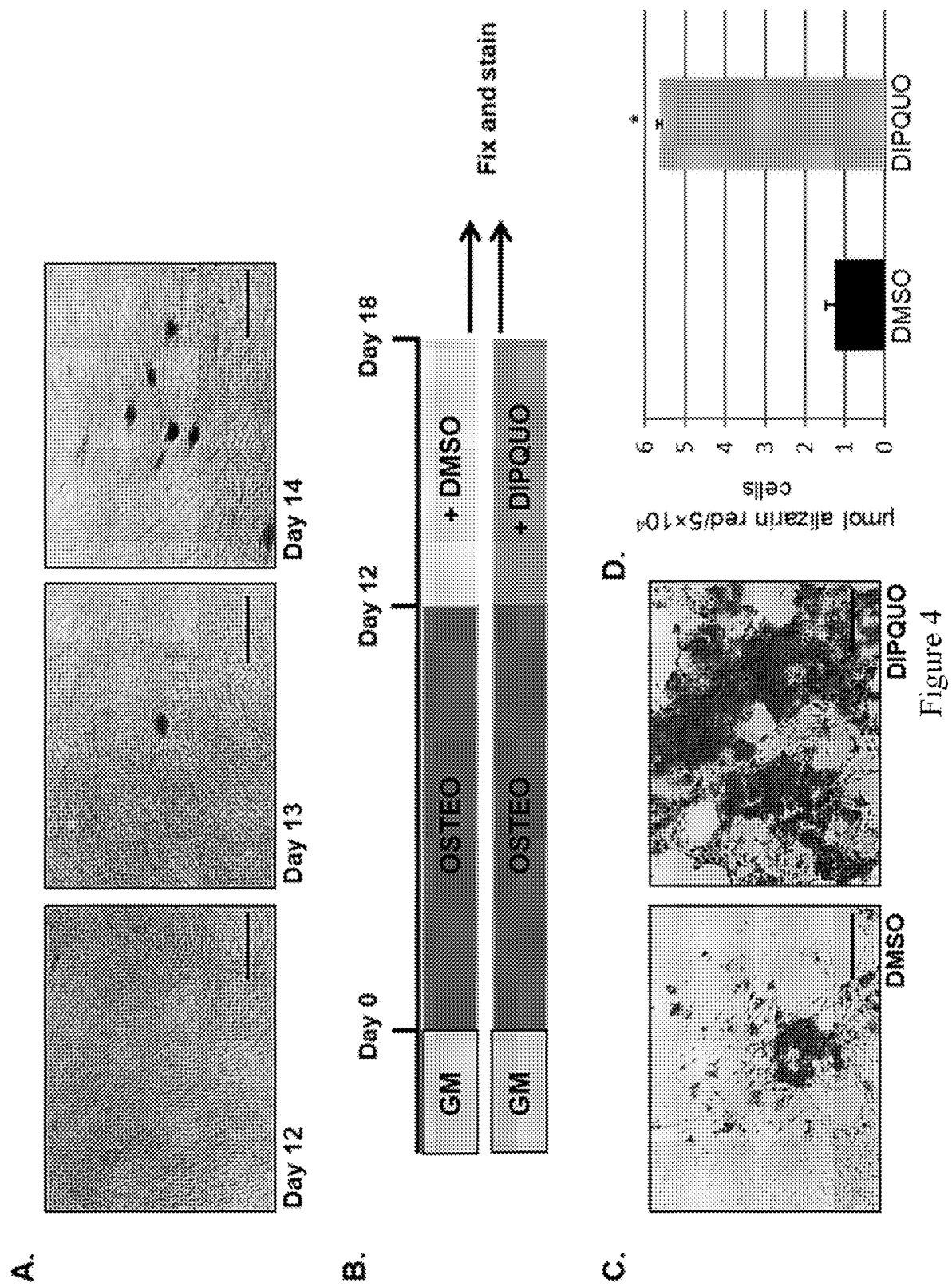
FIG. 4. DIPQUO Promotes Osteoblast Differentiation and Mineralization in Human Mesenchymal Cells (A) Timing of spontaneous mineralization in hMSCs cultured under conditions permissive for osteogenic differentiation in untreated controls. Cells were stained with 2% alizarin red on the day indicated with respect to maintenance in osteogenic medium. Representative images are shown. Scale bars, 400 mm. (B) Schematic of in vitro mineralization assay. Human mesenchymal stem cells were cultured in complete growth medium and then transferred to osteogenic medium containing known osteoblastogenic cytokines and compounds. After 12 days of differentiation, cells were treated with DMSO or 10 mM DIQPUO for an additional 6 days. At day 18, cells were fixed and stained with 2% alizarin red. (C) Representative images of day 18 alizarin redstained DMSO- and DIPQUO-treated differentiation cultures. Scale bars, 400 mm. (D) Stain was harvested at 85° C. with acetic acid and quantified by reading absorbance at 405 nm in flat-bottom 96-well plates. n=3, **p<0.01.

To extend these observations to human osteoblast maturation, a quantitative assay was used to analyze mineralization in differentiating primary human mesenchymal stem cells (hMSCs). Bone marrow-derived hMSCs were cultured in unbiased growth medium for at least two passages and then cultured in osteogenic medium for 12 to 21 days and stained with alizarin red to identify a time window in which spontaneous mineralization first occurred (FIG. 4A). Subsequently, hMSCs in osteogenic medium were treated continuously with DIPQUO from day 12 to 18, stained and compared with equivalent DMSO treated controls, and then normalized to total cell numbers (FIG. 4B). DIPQUO-treated samples incorporated alizarin red in a molar ratio approximately 5 times greater than DMSO-treated samples (FIGS. 4C and 4D). Therefore, DIPQUO showed osteogenic activity in both mouse and human model systems.

Figure 8:
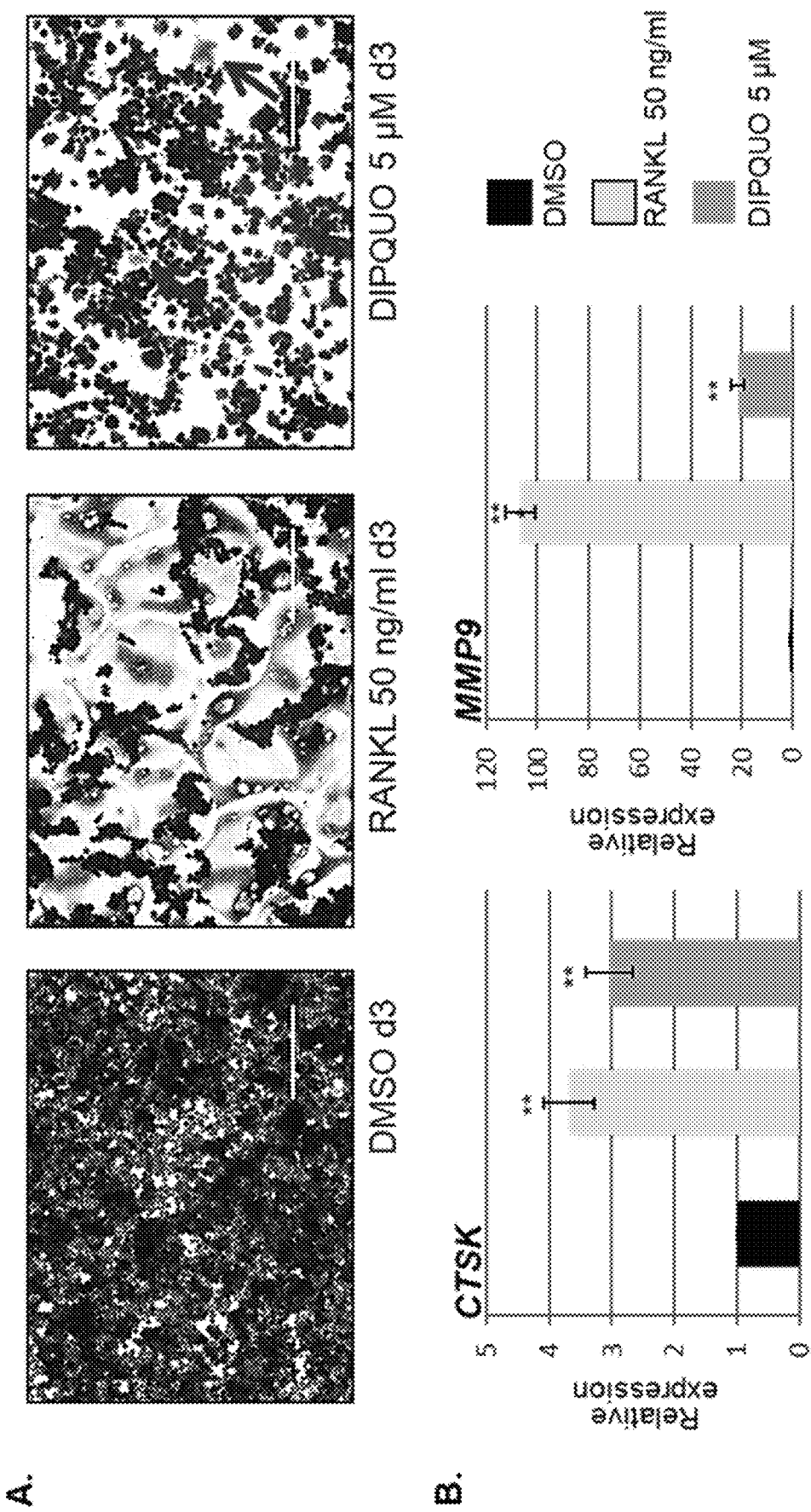
FIG. 8. DIPQUO is a minor activator of the osteoclast differentiation program. Tartrate-resistant acid phosphatase (TRAP) assays (A) for multinucleated osteoclasts (light purple cells, also marked with red arrows in DIPQUO-treated panel) and quantitative RT-PCR measurement of regulatory gene expression (B), demonstrate moderate activation by DIPQUO of the osteoclastogenic program, in contrast to much greater activation by RANKL-stimulated positive controls. Representative images are shown. For qRTPCR, RANKL- and DIPQUO-treated cultures were compared to DMSO-treated controls (n=3). Scale bar equals 200 μm.

To address the specificity of DIPQUO for stimulating an osteogenic versus osteoclastic program, the RAW 264.7 murine macrophage cell line was assayed for osteoclast differentiation by staining for tartrate-resistant acid phosphatase (TRAP) to distinguish multinucleated osteoclasts from macrophages. Receptor activator of nuclear factor kB ligand (RANKL) was used as a positive control to stimulate osteoclast differentiation, and was found to promote both TRAP staining (large, light purple cells) and expression of the osteoclast marker genes cathepsin K (CTSK) and matrix metalloprotease 9 (MMP9) (FIG. 8). DIPQUO treatment resulted in comparatively few TRAP-positive cells, and even these were much smaller than those induced by RANKL (red arrows, FIG. 8). CTSK and MMP9 were upregulated, albeit to a lower level compared with RANKL induction. Thus, DIPQUO appears to be primarily supportive of osteogenesis.

Figure 5:
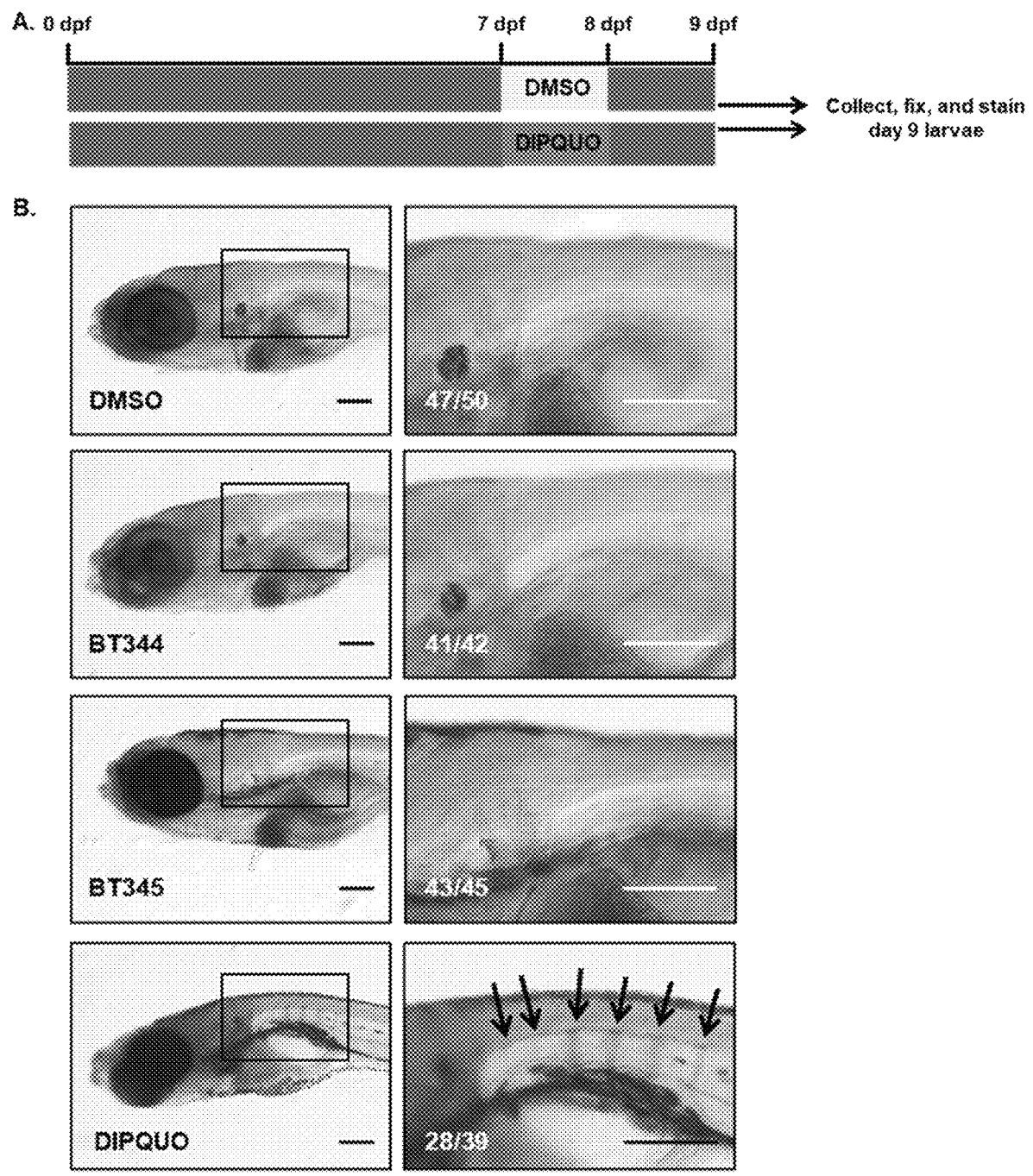
FIG. 5. DIPQUO Stimulates Ossification and Osteoblast Differentiation in Zebrafish Developmental and Regenerative Models (A) Schematic of treatment regime in larval zebrafish notochord ossification model. Zebrafish larvae at 7 days post-fertilization (dpf) were treated for 24 h with DMSO, 15 mM inert analogs BT344 or BT345, or 15 mM DIPQUO, which was washed out at 8 dpf. Larvae were then maintained for an additional 24 h and fixed and stained with alizarin red at 9 dpf. (B) Representative images of alizarin red-stained DMSO-, analog-, and DIPQUO-treated larvae at 9 dpf. DIPQUO-treated larvae displayed an accelerated and accentuated staining pattern marking ossified vertebral primordia that emerge from the developing notochord (arrows in bottom right panel). For each condition, the image to the right is expanded from the black inset box. Larvae were scored for whether >2 vertebral primordial were stained; representative images are shown with ratios reflecting the number out of total with representative staining. Independent clutches of larvae were treated and stained at least in duplicate for every condition. Scale bars, 100 mm. (C) The distal portion of caudal fin was removed on a diagonal from adult fish (dotted line) and allowed to regenerate at 32° C. After 26 h, the fin regenerate was removed more proximally, fixed, and analyzed by immunofluorescence for osteoblast markers. Black square represents area of detail shown in (D). Scale bars, 100 mm.
Figure 5:
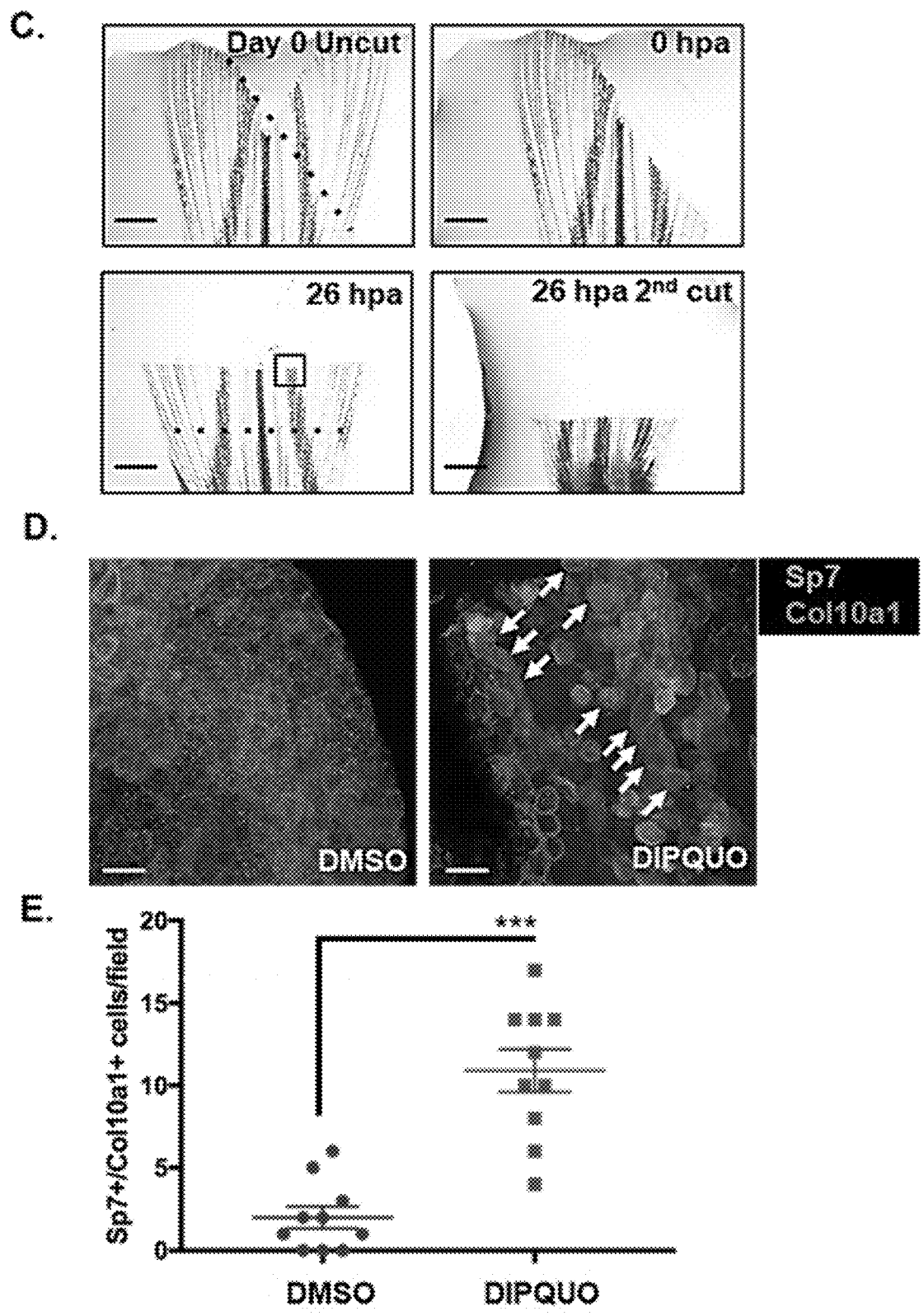

DIPQUO Promotes and Accelerates Bone Mineralization In Vivo To address whether the observed effects of DIPQUO on osteoblast differentiation and maturation could extend to an in vivo bone model, we utilized the zebrafish, Danio rerio. First, zebrafish were used as a model system to examine developmental ossification via direct vertebral specification through conversion of the notochord sheath (Inohaya et al., 2007; Laue et al., 2008). During zebrafish larval stages, the extent and pattern of ossification observable at discrete developmental time points are susceptible to perturbation by cytokines or genetic modulation. The contribution of extrinsic factors to notochord ossification and patterning can be measured by alizarin red staining in a manner analogous to its application in gauging osteoblast maturation in cultured cells. Accordingly, a 24-h pulse of DIPQUO treatment was found to accelerate and accentuate mineralization of incipient vertebral primordia by 9 days post-fertilization, in comparison with controls treated either with DMSO vehicle or with inert structural analog compounds (FIGS. 5A and 5B).

We next tested the regenerative capabilities of zebrafish, which have a robust capacity to replace and renew organs and tissues derived from all three germ layers. Regenerating fin joints are reported to constitute a pre-osteoblast niche from which OSX-expressing (Sp7+) osteoblasts radiate de novo (Ando et al., 2017). Simultaneously, osteoblasts and osteogenic hypertrophic chondrocytes in both early and later stages of differentiation express collagen10 (col10a1) (Huycke et al., 2012). In a zebrafish regeneration model system, in which the distal portion of the caudal fin was amputated and allowed to regenerate (FIG. 5C), the number of Sp7+/Col10a1+ cells emanating from new fin ray joints was significantly increased in tissue derived from DIPQUO-treated fish compared with control DMSO-treated fish (FIGS. 5D and 5E). Taken together, these findings demonstrate a strong activity for DIPQUO as a stimulator and enhancer of osteogenic differentiation and maturation in vivo.

Figure 6:
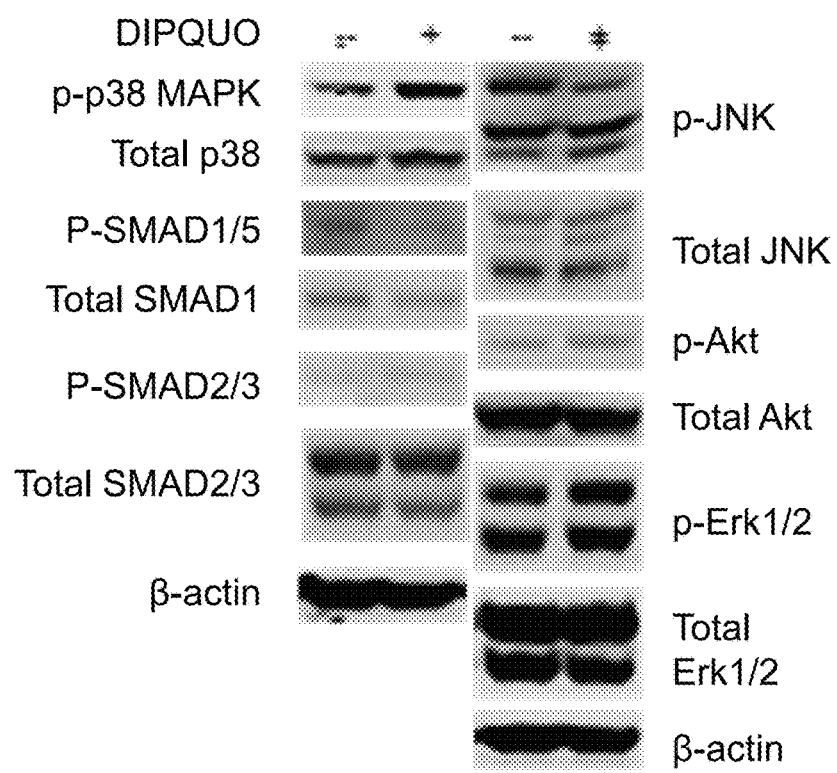
FIG. 6. DIPQUO Functions Mechanistically through Activation of p38 MAPK Signaling (A) Serum-starved C2C12 myoblasts were treated with DMSO or DIPQUO for 4 h and whole-cell extracts were examined by western blotting for a panel of TGF-β, BMP, and MAPK signaling effector molecules commonly modulated during osteoblast differentiation. p38 MAPK phosphorylation was found to be significantly activated by DIPQUO, whereas JNK p54 activity was suppressed (n=3). (B) In BRITER cells, which allow CRE-ER inducible suppression of BMP2/BMP4 expression, western blotting showed significant activation of p38 MAPK under conditions of both BMP suppression and exogenous addition of BMP4. In addition, SMAD1/5 were activated by exogenous BMP4 both in the absence and presence of DIPQUO (n=3). In all experiments *p<0.05, p<0.01, *p<0.001. (C) Western blotting analysis of p38 MAPK upstream activators in BRITER cells, at time points indicated after initial DIPQUO treatment (MKK3/6 n=4; TAK1 n=3). Shaded key for experimental treatments corresponds to (A-C). For these and all subsequent western blotting analyses, protein levels were quantified and normalized relative to DMSO-treated controls. (D) Inhibition of p38 MAPK signaling with 10 mMSCIO469 attenuated DIPQUO activation of ALP expression, and inhibition of BMP receptor II activation with 1 mM LDN193189 attenuated BMP activation of ALP expression in C2C12 cells. However, BMP inhibition did not block DIPQUO activation of ALP nor did p38 MAPK inhibition block BMP activation of ALP. Scale bars, 400 mm. (E) Western blotting analysis of isoform-specific individual knockdown of p38-α and -β after 48 h of small interfering RNA (siRNA) transfection in C2C12 cells (n=3). (F) Attenuation of ALP expression in DIPQUO-treated C2C12 cells specifically by p38-β knockdown (n=3). Representative image of C2C12 cells transfected with siRNA for 24 h, then treated with 10 mM DIPQUO for 2 days and stained for ALP expression. Scale bars, 400 mm. (G) ALP activity assay in equivalent samples depleted of p38-α and -β isoforms shows specific requirement for p38-β to mediate stimulatory effect of 10 mM DIPQUO (n=3). (H) Isoform-specific immunoprecipitation demonstrates significant decrease in p38-α and increase in p38-β activities induced by 10 mM DIPQUO treatment (n=3). See also FIG. 9.
Figure 6:
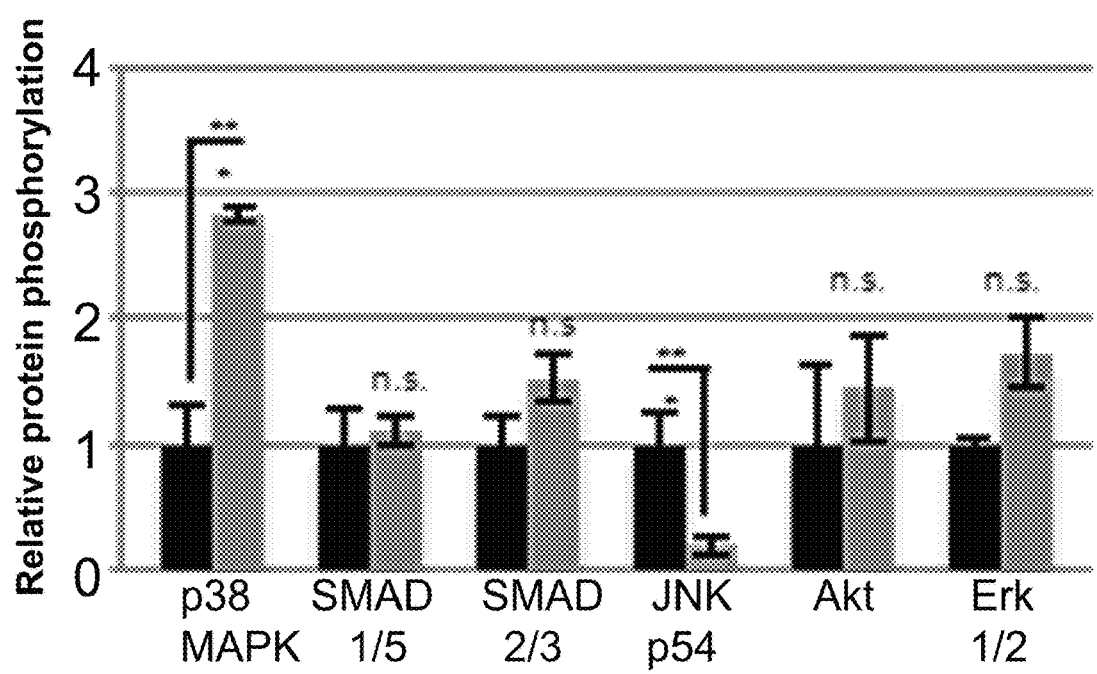
Figure 6:
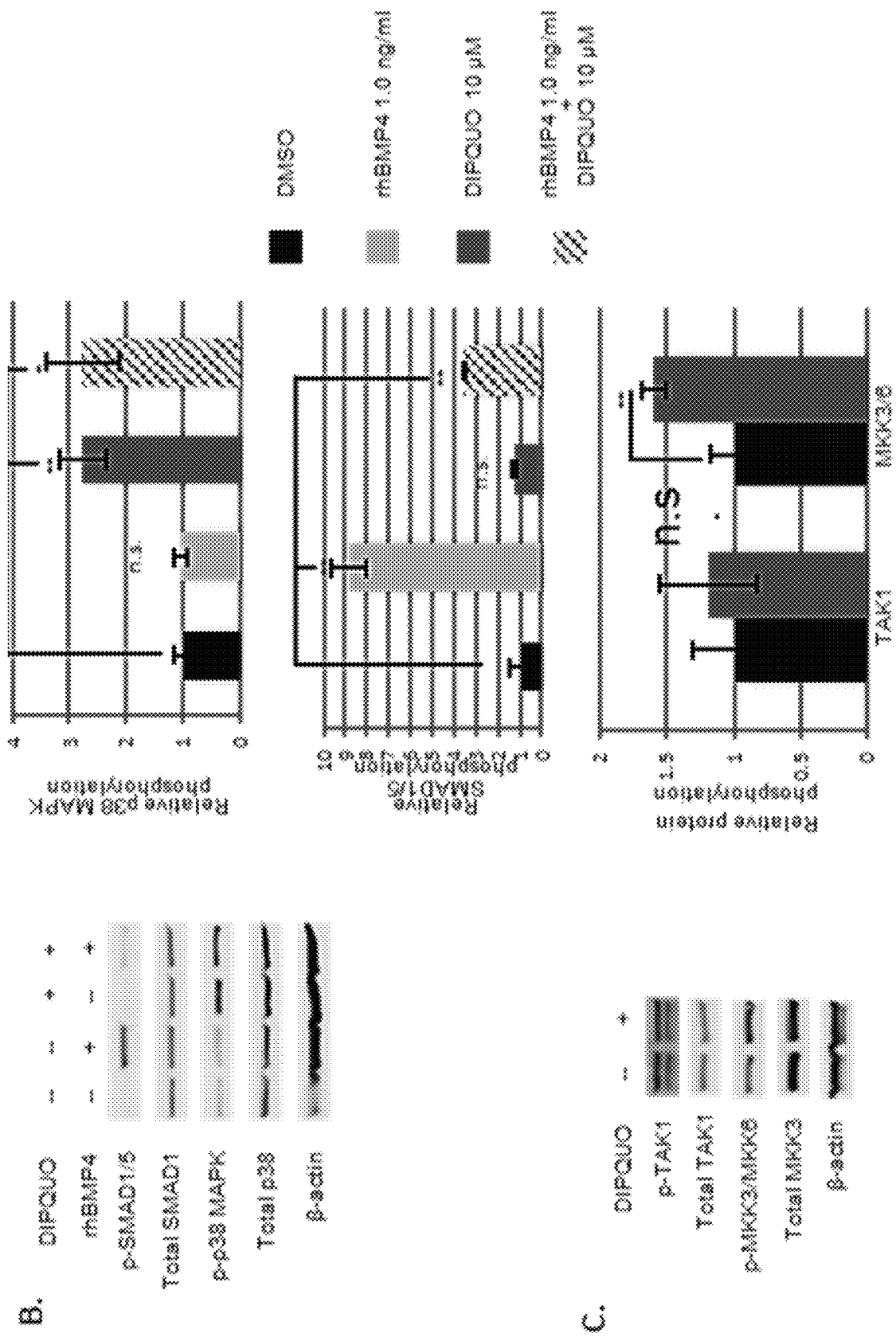
Figure 6:
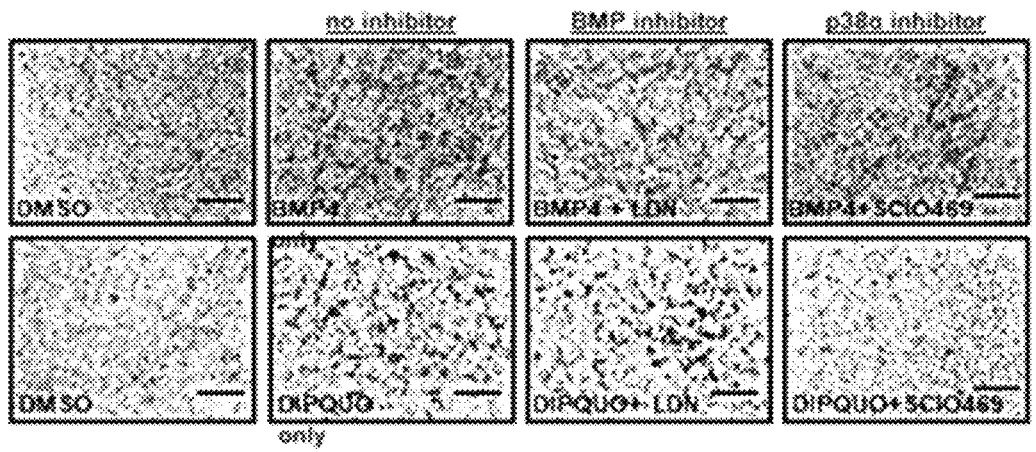
Figure 6:
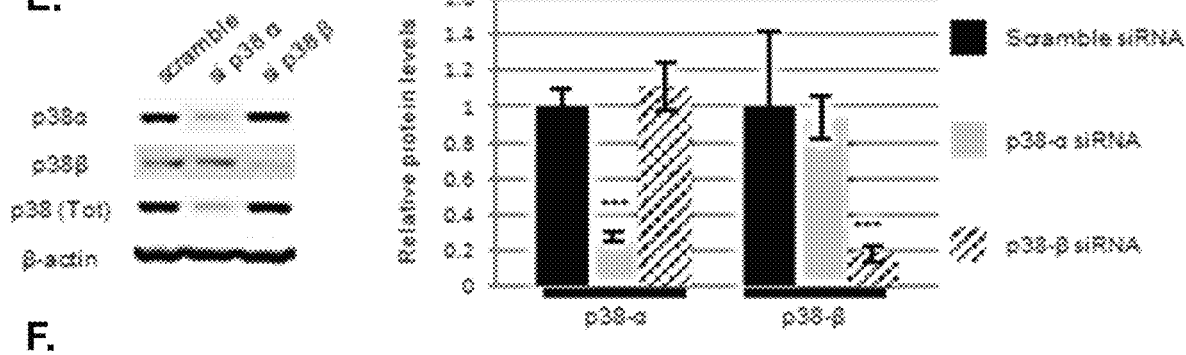
Figure 6:
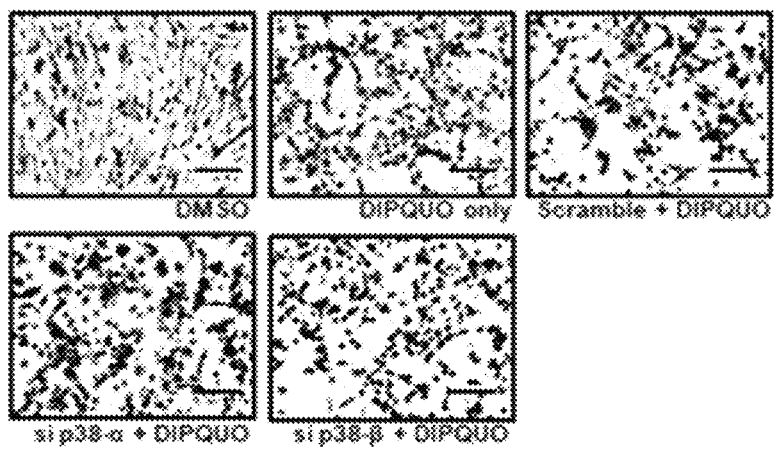
Figure 6:
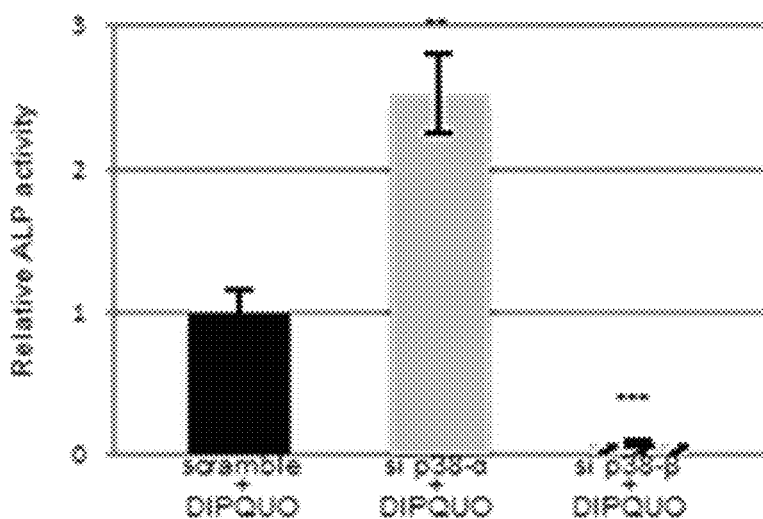
Figure 6:
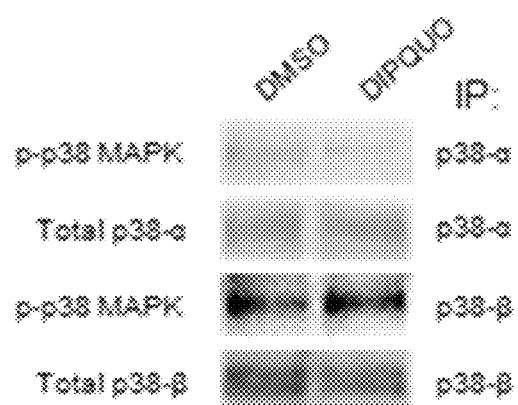
Figure 6:
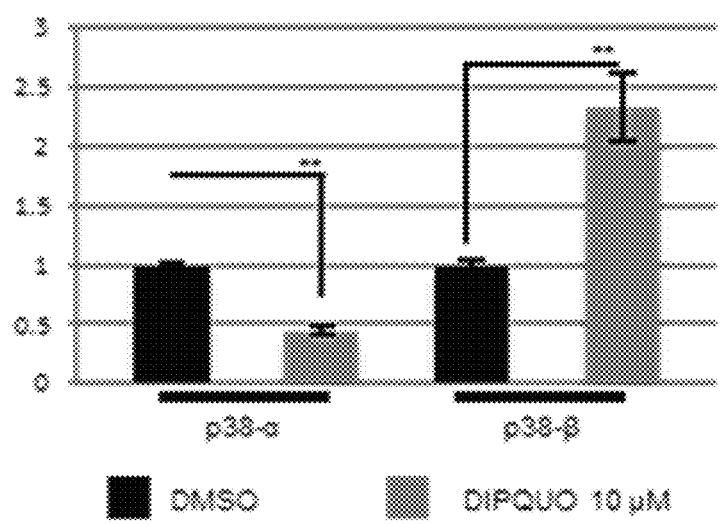

DIPQUO Leads to an Isoform-Specific Activation of p38 MAPK Signaling. The unbiased approach used to identify DIPQUO provides little information on which signaling pathways are impacted as downstream effectors to mediate osteogenesis. Therefore, we investigated the activation status of several pathways, focusing particularly on effectors of the transforming growth factor β (TGF-β superfamily including relevant branches of the mitogen-activated protein kinase (MAPK) pathway. In C2C12 cells, DIPQUO selectively activated p38 MAPK signaling, whereas it suppressed the p54 isoform of the C-terminal Jun kinase family (JNK) (FIG. 6A). Treatment with inert analog compounds did not alter p38 MAPK or JNK signaling (data not shown). There was no change observed in other pathways of interest, including phosphoinositol 3-kinase (PI3K/Akt), extracellular signal-regulated kinase (ERK), TGF-β/SMAD2/3, and notably BMP/SMAD1/5/9 (FIG. 6A). In BRITER cells, a murine transformed osteoblast line that allows tamoxifen-inducible repression of BMP-2 and BMP-4 expression (Yadav et al., 2012), DIPQUO maintained the ability to activate p38 MAPK even under conditions of BMP repression (FIG. 6B).

Figure 9:
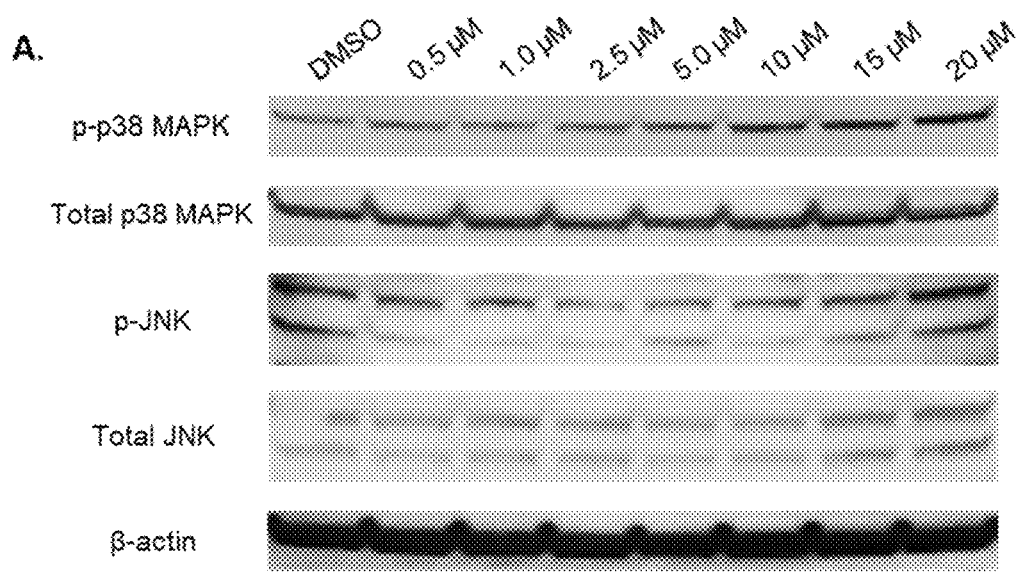
FIG. 9. (Refers to FIG. 6) Targeting p38 MAPK and JNK pathways is not sufficient to replicate the effects of DIPQUO. Dose-response (A) and time course (B) of DIPQUO treatment demonstrate overlap of kinetic effects on p38 MAPK and INK pathway activation status roughly corresponding to 5-10 μM concentration and 6-8 hours of treatment. D=DMSO control. Representative images are shown from western blotting experiments performed in triplicate or greater (n≥3). Additionally, forced expression of p38-MAPK activators MKK3 and MKK6, individually or in combination, did not impact ALP expression or activity. C) Representative western blotting image of epitope-tagged MKK3 and MKK6 proteins visualized using epitope-specific antibodies. ALP staining (D) and ALP activity assays (E) performed in triplicate showed no change in ALP status compared to un-transfected, DMSO-treated controls. F) A JNK-specific inhibitor that was found by western blotting to additionally activate p38-MAPK, did not alter ALP expression in staining assays compared to DMSO-treated controls. G) Activation status of a transiently transfected AP-1 response element-luciferase reporter construct was unaffected by treatment with DIPQUO at various concentrations in 293T cells. Luciferase signal was normalized to co-transfected Renilla expression. Data were normalized to signal obtained from negative control. Assays were performed in duplicate and repeated 3×. Error bars=SEM.
Figure 9:
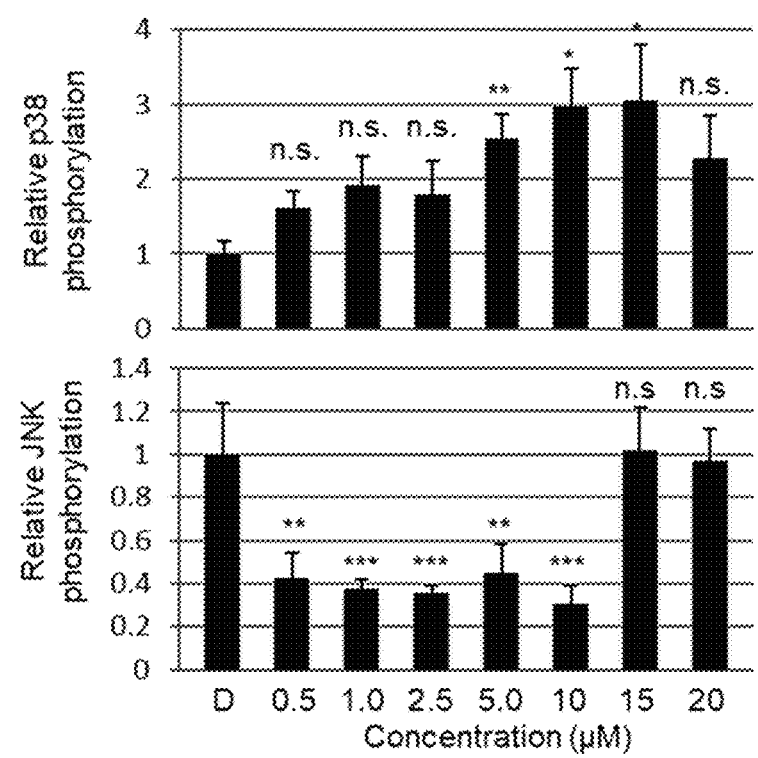
Figure 9:
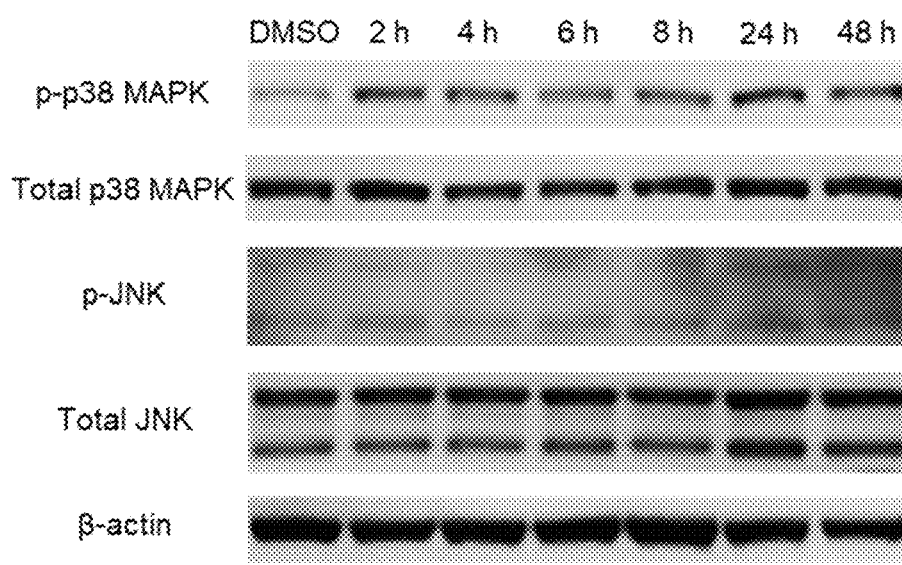
Figure 9:
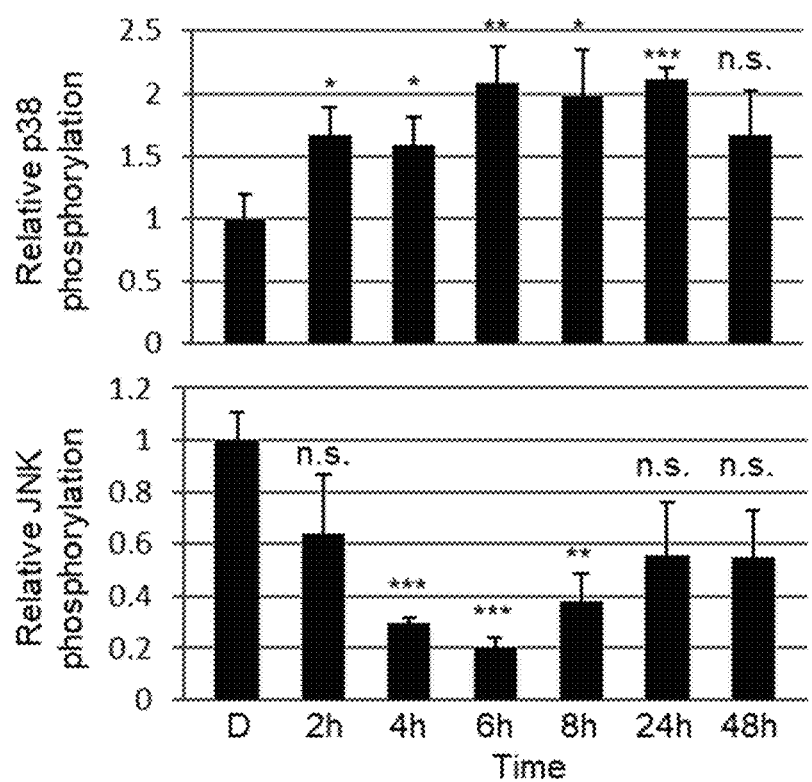
Figure 9:
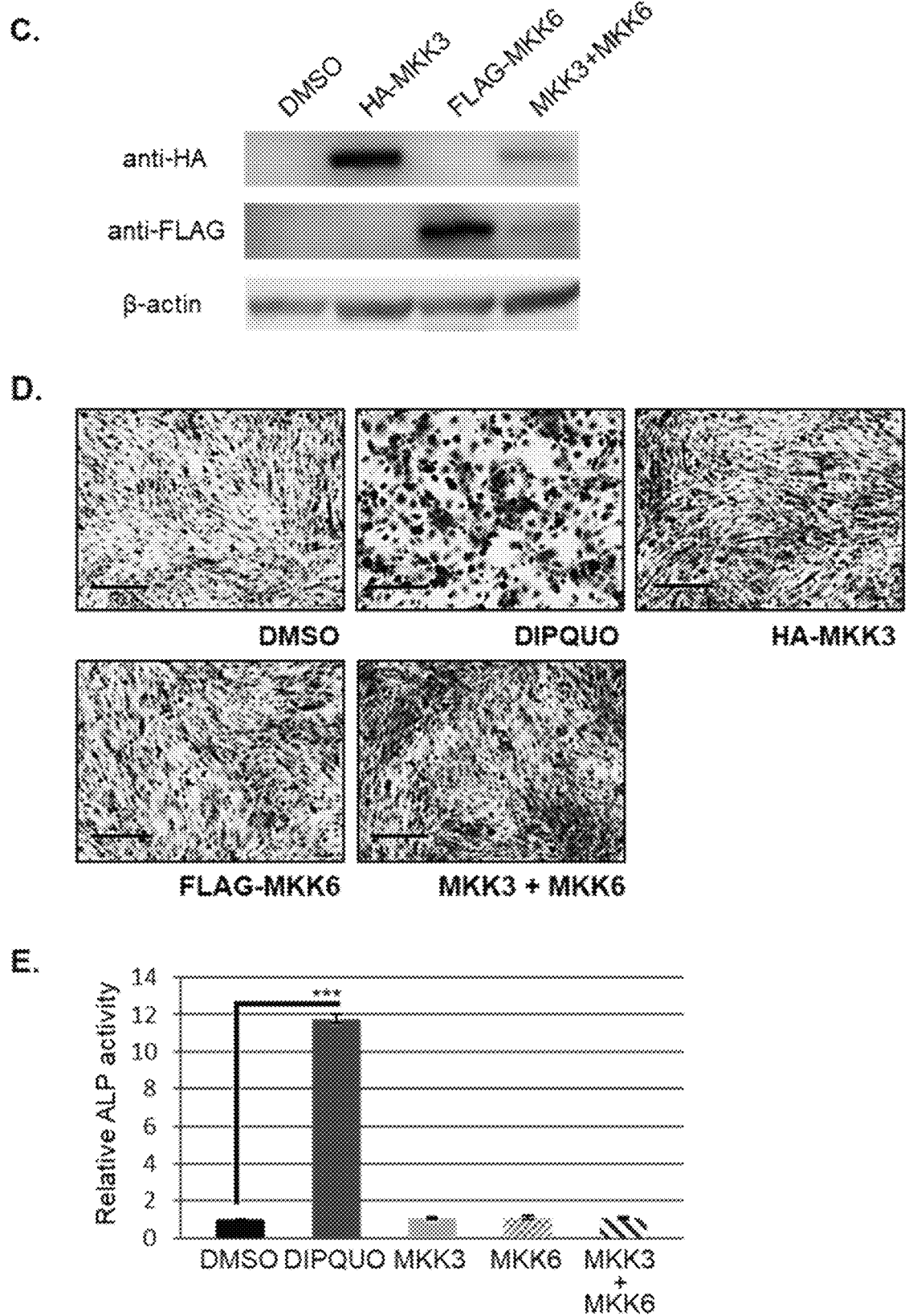
Figure 9:
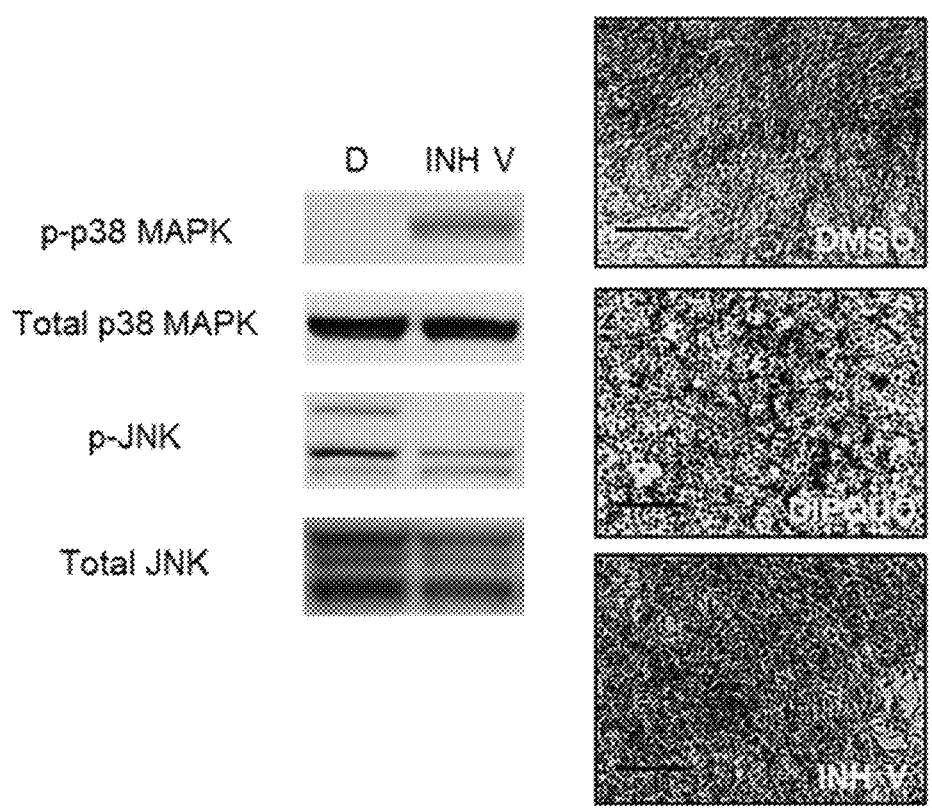
Figure 9:
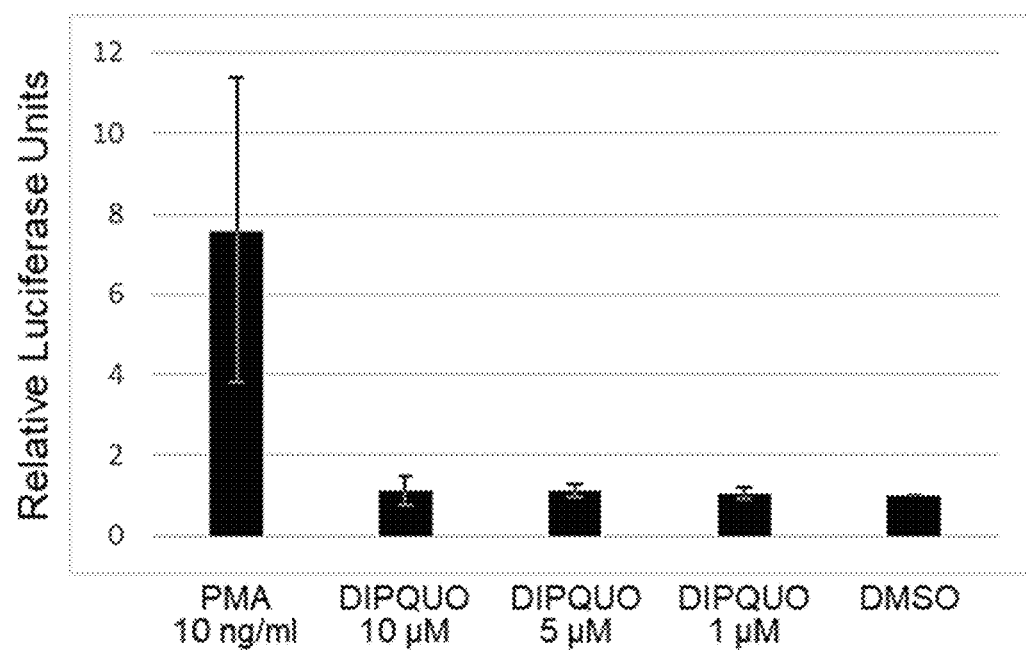
Figure 10:
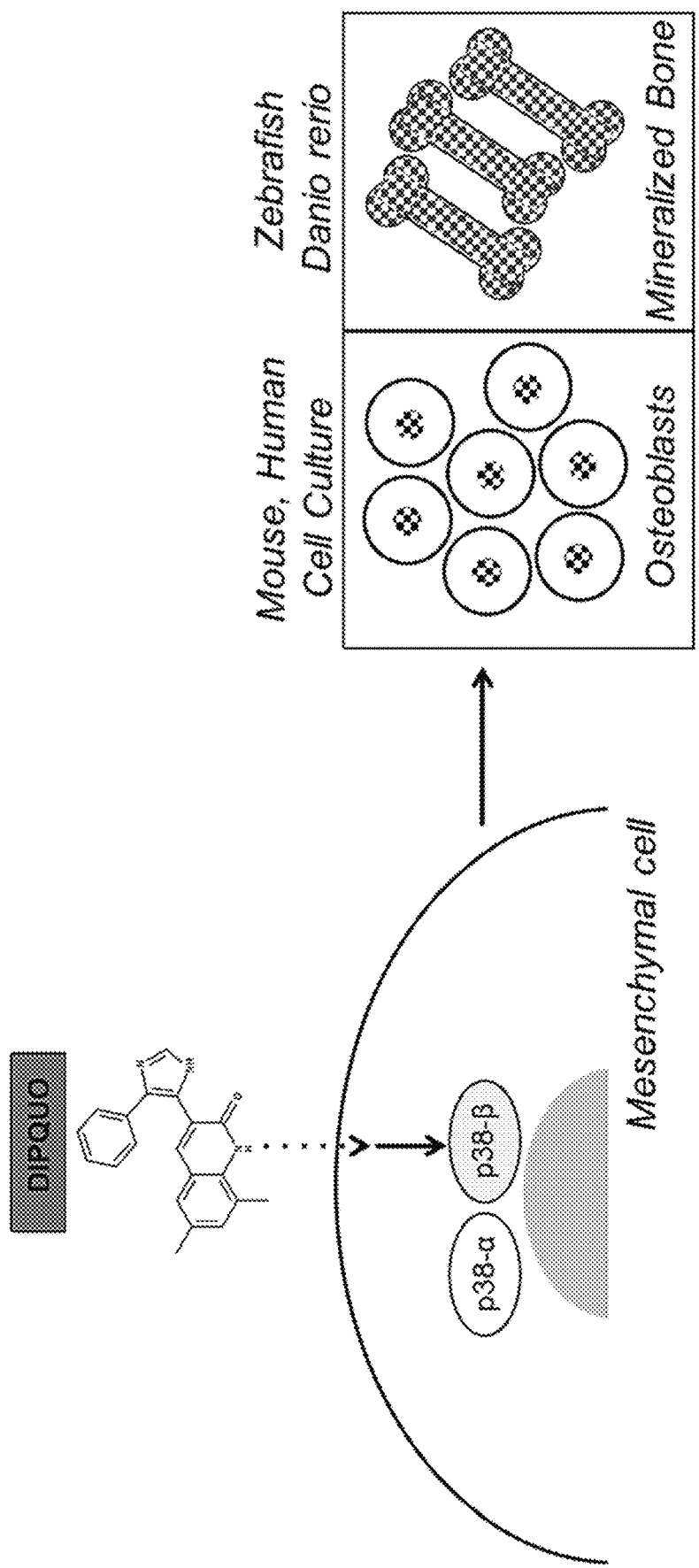
FIG. 10. A cartoon depicting DIPQUO activating p38-β, which promotes bone formation.

In differentiating osteoblasts, p38 MAPK activation is controlled by a MAP kinase cascade initiated through the MAP kinase kinases MKK3 and MKK6 (Greenblatt et al., 2010; Thouverey and Caverzasio, 2015). Accordingly, in BRITER cells DIPQUO stimulated rapid phosphorylation of MKK3/6 (FIG. 6C). Upstream control of MKK3/6 activation did not appear to function through TAK1 (FIG. 6C), or through any of several other tested putative activators, including apoptosis signal-regulating kinase (ASK1), mixed-lineage protein kinase 3 (MLK3), mitogen-activated protein kinase 3 (MEKK3), tumor progression locus 2 (TPL2), and tumor necrosis factor receptor-associated factor 6 (data not shown). The optimal dosages and time courses of treatment to impact p38 MAPK and JNK signaling did not exactly correspond, although there was overlap at 5-10 mM treatment of 6-8 h duration (FIGS. 9A and 9B). Overexpression of MKK3 and/or MKK6 was not sufficient to replicate the effects of DIPQUO (FIGS. 9C-9E). Although DIPQUO suppressed JNK signaling via its p54 isoform, chemical suppression of JNK signaling with the commercial inhibitor SP600125, either with or without p38 MAPK activation by U46619, was not adequate to induce a differentiation phenotype in C2C12 cells, as measured by ALP staining. Treatment with 10 mM JNK inhibitor V was found to both activate p38 MAPK and suppress JNK p54, but this condition also did not lead to ALP-positive staining in C2C12 cultures (FIG. 9F). Neither did DIPQUO stimulate activation of a luciferase reporter driven by the AP-1 response element (FIG. 9G). However, chemical inhibition of p38 MAPK with SCI0469 attenuated ALP expression in DIPQUO-treated cells (FIG. 6D). This effect was found to be specific, as inhibition of BMP signaling attenuated BMP-driven, but not DIPQUO-driven, differentiation (FIG. 6D).

There are four separate p38 isoforms: α, β, γ, and δ. The respective roles of the α and β isoforms in bone differentiation have been dissected to the extent that p38-β is known to be involved specifically in skeletogenesis (Greenblatt et al., 2010), while p38-α has roles that are both wide-ranging and highly specific, for instance in dentition (Greenblatt et al., 2015). Accordingly, we used small interfering RNA-mediated knockdown to probe the specificity of DIPQUO to block the activity of one or the other isoform (FIG. 6E). We found that knockdown specifically of the β isoform, but not the a isoform, attenuated ALP expression in DIPQUO-treated C2C12 cells (FIG. 6F), and resulted in an almost total block of ALP enzymatic activity (FIG. 6G). To confirm the biological significance of this observation, the α and β isoforms were immunoprecipitated from C2C12 cells and analyzed for relative activity levels. The β isoform was significantly activated after DIPQUO treatment, while p38-α was suppressed (FIG. 6H). In summary, these results suggest that p38 MAPK activation is necessary for DIQPUO driven osteoblast differentiation, and that DIPQUO functions specifically in a manner that leads to activation of p38-β.

Discussion

Through chemical screening, we report the discovery of a small molecule, 6,8-dimethyl-3-(4-phenyl-1H-imidazol-5-yl)quinolin-2(1H)-one (DIPQUO) that promotes osteoblast differentiation and maturation in murine and human progenitor cells. Furthermore, DIPQUO stimulates developmental ossification and regenerative production of differentiating zebrafish osteoblasts in vivo. It should be noted that these are normal physiological processes that are accelerated or enhanced by DIPQUO treatment. Although not intending to be bound by any particular theory, it is considered that mechanistically, DIPQUO functions to activate p38 MAPK signaling as an intracellular effector, specifically through the p38-beta isoform, although the direct interaction target is unknown. While DIPQUO has not been shown to be a p38-beta "activator", it likely targets one or more unknown proteins that result in p38-beta activation. However, p38-beta is an attractive starting point for drug discovery, given the phenotypic specificity for defects in skeletogenesis in murine models of p38-beta deficiency. DIPQUO therefore has strong potential both as a research tool and for bone repair and remodeling dysfunction.

Several signaling pathways contribute to developmental control of osteogenic programs, including those regulated by BMP, Wnt, Notch, and hedgehog ligands (Chen et al., 2012; Kim et al., 2013; Rodda and McMahon, 2006). Additionally, diverse extracellular ligands impact osteoblast differentiation, including BMPs, parathyroid hormone (PTH), fibroblast growth factors (FGFs), and noncanonical WNTs, all of which converge on MAPK cascade-driven mechanisms (Chen et al., 2012; Lin and Hankenson, 2011). Roles in early osteoblast differentiation have largely been ascribed to p38 MAPK (Rey et al., 2007; Thouverey and Caverzasio, 2015), while later roles have been identified for JNK-mediated MAPK signaling (Matsuguchi et al., 2009). The relative contributions of p38 MAPK alpha and beta isoforms to osteoblast biology have been dissected in murine genetic loss-of-function models. Although p38-alpha deletion results in pleiotropic defects that include deficits in skeletogenesis and dentition (Greenblatt et al., 2015; Greenblatt et al., 2010), p38-beta-deficient mice are phenotypically normal with the exception of a skeletal deficit in bone mineral density (Greenblatt et al., 2010). Lacking in this analysis, however, is a dedicated p38 MAPK isoform-specific activator that can be used to probe models of biological function in different cell culture and in vivo systems, and also to investigate putative uses as an ameliorative agent in preclinical models of bone repair, regeneration, and dysfunction. Although DIPQUO stimulates MKK3/6-directed activation of p38 MAPK signaling, the panel of known MAPKKK activators that can initiate a p38 signaling cascade in differentiating osteoblasts that were tested did not yield an obvious candidate. Therefore, DIPQUO may maintain an affinity for an unresolved target that has not previously been appreciated to have a role in control of p38 MAPK signaling in bone biology.

The osteogenic effect of DIPQUO is robust, significantly enhancing differentiation and calcium deposition in multipotent bone progenitors and developing notochord, and stimulating emergence of new osteoblasts in regenerating tissue. However, when tested in a cell-based model of bone resorption using osteoclast markers as surrogates, we found that while there is a modest increase in phenotypic osteoclasts, there is a significant up-regulation of two osteoclast differentiation markers. Therefore, based on this disclosure, DIPQUO can be used to stimulate physiological bone remodeling, which requires a balance between osteoblast-driven building and osteoclast-driven resorption programs. Recent studies have associated bone fracture and fragility with long-term use of approved resorption-blocking osteoporosis therapies (Drieling et al., 2016; Lloyd et al., 2017;

Ma et al., 2017; Saita et al., 2015). Thus, DIPQUO can be used for bone regenerative therapies.

There are currently few therapeutics useful for promoting bone formation following bone fracture or degeneration. This study used an unbiased high throughput screen to identify a small molecule compound, DIPQUO, that activates an osteogenic program in mouse and human cells, and promotes bone formation during zebrafish development and regeneration. Although the direct target is not known, functional activity is associated with activation specifically of the beta isoform of the p38 MAPK, known from mouse studies to be important for skeletogenesis. As such, DIPQUO can be used for bone therapeutics.

Methods

Experimental Model and Subject Details

The mouse myoblast cell line C2C12 was purchased from ATCC and cultured in Dulbecco's Modified Eagle Medium (DMEM) with 10% FBS. Primary bone marrow-derived hMSCs (Lonza) were maintained and passaged in complete hMSC growth medium (Lonza) and maintained in DMEM with 10% FBS. For AP-1 reporter assays, 293T HEK cells were used. Zebrafish were a hybrid strain from crossing AB and Tub strains. Larvae were used prior to sex determination. For adults, both males and females were used without any apparent difference. All animal work was carried out according to an IACUC-approved protocol.

Method Details

High Throughput Screening

For the primary screen, library compounds were distributed onto 384-well microplates (Greiner Bio-One 781091) at a final concentration of 10 µM in culture medium using a Perkin Elmer Janus automated workstation and WinPrep Version 4.8.3.315. Positive (rhBMP4, 1 ng/ml, R&D Systems) and negative controls (DMSO, 0.2%) were manually added to each plate by multichannel pipet. C2C12 cells were seeded onto compounds and controls at a density of 2000/well using a Thermo Multidrop Combi reagent dispenser and cultured for 4 days at 37° C., 5% $CO_2$. Culture medium was aspirated using a BioTek EL406 plate washer and cells were lysed in RIPA buffer (Millipore 20-188) at ambient temperature for 10 minutes. 10 µl fluorescent alkaline phosphatase substrate (AttoPhos, Promega S1000) was added to lysates and incubated an additional 10 minutes before measuring the fluorescence (Excitation 450 nm/Emission 580 nm) on a BioTek Synergy Neo2 stacking microplate reader. Plates were processed and relative fluorescence raw values measured in stacks of 10-20. The data were processed using Collaborative Drug Discovery web-based software (CDD Vault) to determine Z score calculated on DMSO control wells and percent activation normalized against positive and negative controls (NPA). Cherry-picked hit candidates were re-tested in concentration response experiments, from which 4 candidates were chosen and purchased for further testing from either ChemBridge or Enamine, based on availability. DIPQUO (ChemBridge 16707928) emerged as the top candidate. For all subsequent experiments, DIPQUO was used that had been re-synthesized by ChemBridge Corp. Proton and carbon nuclear magnetic resonance spectral analysis was performed on re-synthesized compound, and additional structure-activity relationship analysis was performed on several structural analogs that were modified around the imidazole and quinolinone moieties, again using the Atto-Phos assay (Table 5).

For detailed procedures used to design and synthesize analog compounds, refer to Supplementary Methods section. We also purchased a library of 154 structural chemical analogs assembled by ChemBridge Corp. from available screening library compounds. Analogs contained modifications around the quinolinone and imidazole moieties, and are shown in Table 6. Compounds were tested for activation of ALP in C2C12 cells using conditions identical to the original screen, with the following exceptions: 1) analogs were tested in duplicate at final concentrations of 1, 5, and 10 µM, and 2) DIPQUO, instead of recombinant BMP4, was used as a positive control. In-depth description of the primary screen, including a complete list of primary hits, is presented in Supplementary Tables 1-4.

Cell Culture and Staining Assays

C2C12 cells were treated for 2 days with 10 µM DIPQUO or structural analogs, 1 ng/ml rhBMP4, or with inhibitors as noted in figure legends, and then fixed briefly in 70% acetone/10% formaldehyde/20% citrate. Staining was achieved using the leukocyte alkaline phosphatase kit (Sigma 86R-1KT) according to the manufacturer's instructions. Expression of ALP was confirmed and quantified by flow cytometric analysis, using an Accuri C6 flow cytometer. Briefly, control- or DIPQUO-treated C2C12 cells were detached and harvested on day 2 using PBS-based enzyme-free cell detachment solution (ThermoFisher). $2 \times 10^5$ cells were incubated on ice for 30 minutes with 10 µl APC-conjugated ALPL antibody (R&D Systems), and washed in ice-cold PBS before analysis. Live cells were gated and analyzed in CFlow Plus software and then data was converted to FlowJo to achieve publication-level resolution. For siRNA experiments, gene-specific oligonucleotides were obtained for mouse p38-alpha (Cell Signaling) and p38-beta (Santa Cruz). Signal Silence scramble siRNA control oligonucleotide was purchased from Cell Signaling. C2C12 cells at 70% confluency were transfected in 12-well plates using Lipofectamine RNAiMax reagent (Invitrogen) according to manufacturer's instructions. Transfected cells were treated 24 hours later with DMSO or 10 µM DIPQUO, and siRNA transfection was repeated after 48 hours without changing culture media. After an additional 3 days, cells were either fixed and stained for ALP expression or analyzed for ALP activity using the AttoPhos Substrate kit. Hemagglutinin and FLAG epitope-tagged MKK3 (pMT2-HA-MKK3) and MKK6 (pcDNA3-FLAG-MKK6) constructs were obtained from Addgene and transfected into C2C12 cells using Lipofectamine LTX with Plus Reagent (ThermoFisher) according to manufacturer's instructions and cell extracts analyzed for protein expression and activity as described below.

For mineralization studies, primary bone marrow-derived hMSCs (Lonza) were maintained and passaged in complete hMSC growth medium (Lonza). Cells were then switched to osteogenic medium (Lonza PT-3002) for 12 days, after which they were treated with DMSO or 10 µM DIPQUO for an additional 6 days. On day 18, cells were washed in PBS, fixed in ice-cold 70% ethanol for 60 minutes, then incubated for 60 minutes in 2% alizarin red solution, pH 4.2. Excess stain was washed away with distilled water. Staining was quantified using the Osteogenesis Quantitation kit (Millipore ECM815) following manufacturer's instructions. Briefly, cultures were incubated in 10% acetic acid for 30 minutes, then scraped and heated to 85° for 10 minutes, placed on ice, and neutralized with NH₄OH. Absorbance was measured at 405 nm using an EMax Plus microplate reader and SoftMax Pro 7.0 software. Molar values corresponding to alizarin red incorporation were obtained in reference to a standard curve generated using serial dilutions of alizarin red in assay buffer, and final values were obtained by normalizing to cell number in each sample.

Cells were maintained in DMEM with 10% FBS. For analysis of DIPQUO effects independent of BMP signaling, BMP-2 and BMP-4 knockdown was achieved by treating cells overnight with 1 µM 4-hydroxytamoxifen (4-OHT), followed by continued maintenance in 1 µM 4-OHT. Cells were serum-starved for at least 6 hours before treatment with recombinant BMP protein or DIPQUO as noted in figure legends.

The RAW 264.7 macrophage cell line was purchased from ATCC and maintained in DMEM with 10% FBS. Cells were treated with 10 µM DIPQUO or 50 ng/ml RANKL (Sigma) for 4 days. Cells were fixed in 70% acetone/10% formaldehyde/20% citrate and TRAP staining was achieved using the Leukocyte Acid Phosphatase kit (Sigma 387A-1KT).

For AP-1 reporter assays, 293T HEK cells were seeded at $0.25 \times 10^6$ cells/well of a gelatin-coated 24-well plate one day before transfection. Plasmid transfections were performed using Lipofectamine LTX (Invitrogen) according to manufacturer's protocol. Briefly, 293T HEK cells were co-transfected with pGL4.44 AP1 [luc2P/AP1 RE/Hygro] reporter plasmid (Promega) and SV40Renilla plasmid as a transfection control. 24 hours after transfection, cells were incubated in serum free DMEM media for 24 hours. The following day, cells were treated with 10 ng/ml PMA (Phorbol 12-myristate 13-acetate; Tocris) or indicated concentration of DIPQUO in serum free DMEM for 7 hours prior to lysis with 1× Passive Lysis buffer (Promega). Luciferase expression was measured using Dual-Glo Luciferase Assay (Promega).

Gene Expression Analysis

For quantitative RT-PCR analysis of gene expression in C2C12 cultures, cells were treated for 2 days with 10 µM DIPQUO and harvested into Trizol reagent (Invitrogen). One microgram of RNA was reverse transcribed using the VILO-RT kit (Invitrogen) to generate cDNA, which was diluted 1:25 in RNase-free H₂O for qPCR with Sybr green using the Roche 480 II LightCycler and the $2^{-\Delta\Delta C_T}$ method (Livak and Schmittgen, 2001). For analysis of osteoclast gene expression, RAW 264.7 cells were treated with DMSO, 50 ng/ml RANKL, or 10 µM DIPQUO for 4 days, then harvested into Trizol reagent and processed as above. Mouse qPCR primers are as follows. Runx2: F(CGGCCCTCCCTGAACTCT) (SEQ ID NO:1); R(TGCCTGCCTGGGATCTGTA) (SEQ ID NO:2); Dlx5: F(GCCCCTACCACCAGTACG) (SEQ ID NO:3); R(TCACCATCCTCACCTCTGG) (SEQ ID NO:4); Osterix: F(AGCGACCACTTGAGCAAACAT) (SEQ ID NO:5); R(GCGGCTGATTGGCTTCTTCT) (SEQ ID NO:6); ALP: F(AACCCAGACACAAGCATTCC) (SEQ ID NO:7); R(GAGACATTTTCCCGTTCACC) (SEQ ID NO:8); Osteocalcin: F(GCAGCTTGGTGCACACCTAG) (SEQ ID NO:9); R(GGAGCTGCTGTGACATCCATAC) (SEQ ID NO:10); Osteoactivin: F(TCTGAACCGAGCCCTGACATC) (SEQ ID NO:11); R(AGCAGTAGCGGCCATGTGAAG) (SEQ ID NO:12); CTSK: F(AGGCATTGACTCTGAAGATGCT) (SEQ ID NO:13); R(TCCCCACAGGAATCTCTCTG) (SEQ ID NO:14); MMP9: F(GCGGACATTGTCATCCAGTTTG) (SEQ ID NO:15); R(CGTCGTCGAAATGGGCATC) (SEQ ID NO:16); Gapdh F(CTAACATCAAATGGGGTGAGG) (SEQ ID NO:17); R(CGGAGATGATGACCCTTTTG) (SEQ ID NO:18). RNA-seq studies were carried out with the assistance of the Weill Cornell Genomics Core Facility, using the Illumina HiSeq4000 next-generation sequencer to generate reads from cDNA libraries generated from three biological replicates of day 2 DMSO- or DIPQUO-treated C2C12 cells. Gene sets were clustered by biological/disease function using Ingenuity Pathway Analysis (Qiagen Bioinformatics). Heatmaps with hierarchical clustering were generated in R using the CRAN package for a subset of genes involved in bone morphogenesis. Following normalization of the RNA Sequencing counts in DeSeq, z-scores were computed across samples within each gene for use in the heatmap. The accession number for the sequencing data reported in this paper is NCBI GEO: GSE125052.

Western Blotting

Whole cell extracts were collected from C2C12 or BRITER cells in complete lysis buffer (20 mM Tris, 150 mM NaCl, 50 mM NaF, 1% NP40 substitute, HALT protease inhibitor cocktail (ThermoScientific). Proteins were resolved by electrophoresis on pre-cast 10% NuPage Bis-Tris gels (Invitrogen) and transferred to PVDF membranes (Bio-Rad). Membranes were blocked in 5% BSA-TBS-0.5% Tween-20 for 15 minutes, then incubated at 4° overnight with primary antibodies. Antibodies used were: rabbit anti-phospho-p38 MAPK (cat. no. 9211), anti-p38 MAPK XP (8690), anti-phospho-SMAD1/5 (9516), anti-SMAD1 XP (6944), anti-phospho-SMAD2/3 (8828), anti-SMAD2/3 XP (8685), anti-phospho-JNK (4668), anti-SAPK/JNK (9252), anti-phospho-Akt XP (4060), pan anti-Akt (4691), anti-phospho ERK p42/p44 (4377), anti-ERK p42/p44 (9102), anti-phospho-MKK3/6 (12280), anti-MKK3 (8535), anti-phospho-TAK1 (4531), anti-TAK1 (5206), anti-HA (3274), and anti-FLAG (14793); all from Cell Signaling); and mouse anti-p38α (cat. no. 33-1300), anti-p38β (33-8700; both ThermoFisher) and anti-β-actin (Sigma A1978). Proteins were visualized with HRP-conjugated secondary antibodies (Bio-Rad) with WestPico (ThermoFisher) or Immobilon (Millipore) chemiluminescence reagents. Images were obtained and analyzed for relative densitometric relationships on a LI-COR C-DiGit scanner using Image Studio software.

Zebrafish Studies

Animals studies were performed according to protocols approved by the WCMC IACUC. Wildtype (AB/TU hybrid) zebrafish were maintained at 28.5° C. Larval fish were treated from 7 dpf to 8 dpf in tank water with DMSO or with a 24-hour pulse of 15 µM DIPQUO or inert analog BT344 or BT345, and were fixed at 9 dpf in 4% paraformaldehyde overnight rocking at 4° C. Fixed larvae were washed in PBS-0.1% Tween-20 (PBST), followed by 50% ethanol/50% PBST. Larvae were transferred to staining solution (66.5% ethanol, 100 mM MgCl₂, 0.02% alizarin red) and incubated for 40 hours, rocking at room temperature in the dark. Larvae were washed in H₂O+0.1% Tween-20, and excess stain removed by bleaching for approximately 10 minutes in the dark with a 1:1 mixture of 3% H₂O and 2% KOH. Images of staining were obtained using Nikon NIS Elements-BR software version 4.6.00. For the fin regeneration study, adult fish were anaesthetized in tricaine, and the distal portion of the caudal fin was excised. Amputees were allowed to recover in 300 ml tank water, to which was added either 90 μl DMSO or DIPQUO to final concentration of 15 μM. Fish were maintained in this fashion overnight at 32° C. to optimize fin tissue regrowth. After 26 hours, fish were again anaesthetized and the caudal fin was re-amputated more proximally to ensure inclusion of the original amputation site. Tissue was fixed overnight rocking at 4° C. in 4% paraformaldehyde, washed several times in PBST, and then blocked at room temperature for 2 hours in PBST-0.2% BSA. Primary antibodies (rabbit anti-Sp7 and mouse anti-col10a1, Abcam ab94744 and ab49945 respectively) were incubated 1:250 and 1:100 in PBST-0.2% BSA overnight at 4° C., washed several times in PBST-0.2% BSA, and then incubated overnight at 4° C. in secondary antibodies (goat anti-rabbit Alexa 488 and anti-mouse Alexa 568 IgG, ThermoFisher A-11008 and A-11004). Finally, samples were washed several times in PBST and then mounted on slides in 80% glycerol with 2.5% DABCO (1,4-diazabicyclo[2.2.2]octane, Sigma) to preserve brightness. Images were acquired on a Zeiss LSM 800 confocal microscope and Sp7$^+$/col10a1$^+$ cells quantified using ImageJ.

TABLE 1

Primary high throughput screening data (Refers to FIG. 1).

| Category | Parameters | Value/Description |
|---|---|---|
| Assay | Nature of Assay | Cell-based fluorescent assay |
|  | Assay Strategy | Detection of labeled alkaline phosphatase substrate in cell lysates |
|  | Reagents and Sources | Murine C2C12 myoblasts (ATCC) AttoPhos Kit (Promega) |
|  | Assay Protocol | Shown in Table 2 |
| Library Screened | Nature of Library | Small molecule, comprised of natural products, low molecular weight screening compounds, pharmacologically active, and clinically used compounds |
|  | Size of Library | 47,196 |
|  | Source | ChemBridge; ChemDiv; Edelris; Enamine; VitasMLabs; Spectrum; Prestwick; LOPAC Sigma; Microsource; Life Chemicals; Biofocus/Charles River Laboratory |
|  | Details | The library is stored at 5 mM stock in DMSO at −20° C. Complete information on HTSRC library including link to structures: https://www.rockefeller.edu/htsrc/libraries/ |
|  | Quality Control | Sample integrity of the library is periodically confirmed by HPLC-MS of random samples and all re-confirmed hits from screening are routinely tested by HPLC-MS for purity and integrity. |
|  | Concentration Tested | 10 μM in media and 0.2% DMSO |
| HTS Process | Format | 384-well clear bottom tissue culture-treated plate (Greiner) |
|  | Plate Controls | Positive control EC$_{50}$ rhBMP4 (1 ng/ml); negative control DMSO 0.2% |
|  | Plate Number and Duration | 150 plates Stacks of 10 or 20 4 days |
|  | Reagent and Compound Dispensing Systems | Thermo Multidrop Combi with plate stacker; Perkin Elmer Janus equipped with nanohead syringes |
|  | Output, Detector, Analysis Software | BioTek Synergy Neo Gen5 2.0 |
|  | Correction Factors | B-score analysis and correction |
|  | Performance | The average Z' value for the 150 tested plates was 0.54. |
| Post-HTS Analysis | Selection of Active Compounds | Selected from primary screen using thresholds based on statistical criteria |
|  | Retesting of Initial Actives | Original samples reloaded and retested using screening assay; validated compounds tested using dose-response mode |
|  | Structure Confirmation | Compound structure verified by mass spectrometry and HPLC |
|  | Compound Purification/Re-synthesis | Purchased re-synthesized compound from ChemBridge Corp. and retested |
| Screen Results | List of Screening Positives | Shown in Table 3 |
|  | List of Validated Compounds | Shown in Table 4 |
|  | Comments on Active Compound Selection | Highest RFU, NPA, and Z scores, lowest EC$_{50}$ |

TABLE 2

High throughput screening assay protocol (Refers to FIG. 1).

| Step | Parameter | Value | Description |
|---|---|---|---|
| 1 | Plate library compounds | 10 μM in DMSO in cell media (0.2 μl) | Automated by HTSRC |
| 2 | Plate controls | 0.2% DMSO 1 ng/ml rhBMP4 (20 μl) | Added by multi-channel pipette in columns 23 and 24. |
| 3 | Plate C2C12 cells overlaid onto compounds/controls | 2000 cells/well (80 μl) | Added by plate stacking multi-drop. |
| 4 | Incubation time | 4 days | 37° C., 5% CO$_2$ |
| 5 | Aspirate media from C2C12 cells | Approximately 100 μl | Performed by BioTek EL406 plate washer. |
| 6 | Add RIPA Lysis buffer to cells | 10 μl | Added by plate stacking multi-drop. |
| 7 | Incubation time | 10 minutes | Ambient temperature |
| 8 | Add AttoPhos Assay Buffer | 10 μl | Added by plate stacking multi-drop |
| 9 | Incubation time | 10 minutes | Performed in dark at ambient temperature |

TABLE 2-continued

High throughput screening assay protocol (Refers to FIG. 1).

| Step | Parameter | Value | Description |
|---|---|---|---|
| 10 | Assay read-out | Ex 450/Em 580 nm | Performed by BioTek Synergy Analyzer with plate stacker. |

| Step | Notes |
|---|---|
| 1 | Plates used are flat, clear bottom 384-well plates with black sidewalls to block ambient light. |
| 2 | Controls added in 8X concentration so that with cell media volume, final concentration equals 1X. |
| 3 | Cells are plated and cultured in DMEM + 10% FBS. |
| 4 | No media changes during the course of the incubation. |
| 5 | Media is aspirated from corner, 0.1 mm above bottom surface to avoid aspirating cells before lysis. |
| 6 | Commercially purchased RIPA buffer is diluted to 1X from 10X in ddH$_2$O and added at ambient temperature. |
| 7 | Plates are incubated in stacks of 10 with top plate lidded in steps 7 and 9 to exclude ambient light. |
| 8 | Assay buffer is assembled fresh and stored in the dark at 4° C. for a maximum of two weeks. |
| 9 | Plates are incubated in stacks of 10 with top plate lidded in steps 7 and 9 to exclude ambient light. |
| 10 | RFU — Raw data extracted from Synergy |
| | Fluorescence Z score — $\chi$ is the sample |
| | $\dfrac{x - \mu_\chi}{\sigma_\chi}$ — $\mu_\chi$ is the mean of the negative controls; $\sigma_\chi$ is the standard deviation of the negative controls |
| | 10 µM NPA — $\chi$ is the sample |
| | $\dfrac{x - \mu_-}{\mu_+ - \mu_-} \times 100\%$ — $\mu_-$ is the mean of negative controls; $\mu_+$ is the mean of positive controls |

TABLE 3

Summary of primary screen positives and validated compounds (refers to FIG. 1). Bold = validated in secondary assay.

| RU HTSRC Identifier | Chemical Structure | RFU Score Threshold ≥ 800 (Rank/35) | Fluorescence Z Score Threshold ≥ 10 (Rank/24) | NPA Score Threshold ≥ 5.0 (Rank/20) |
|---|---|---|---|---|
| RU-0226606 | 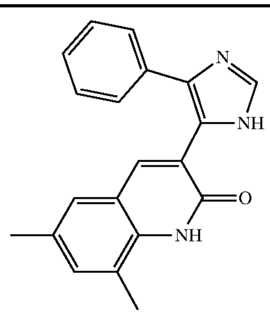 | 4000 (1) | 94.38 (1) | 8.78 (3) |

TABLE 3-continued

Summary of primary screen positives and validated compounds (refers to FIG. 1). Bold = validated in secondary assay.

| RU HTSRC Identifier | Chemical Structure | RFU Score Threshold ≥ 800 (Rank/35) | Fluorescence Z Score Threshold ≥ 10 (Rank/24) | NPA Score Threshold ≥ 5.0 (Rank/20) |
|---|---|---|---|---|
| RU-0229103 | 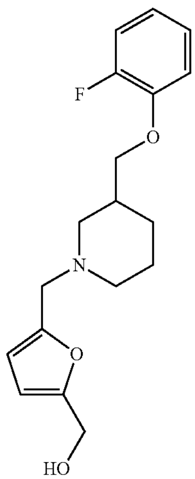 [SMILES: OCc1ccc(CN2CCCC(COc3ccccc3F)C2)o1] | 1980 (2) | 46.85 (2) | 6.82 (4) |
| RU-0238003 | 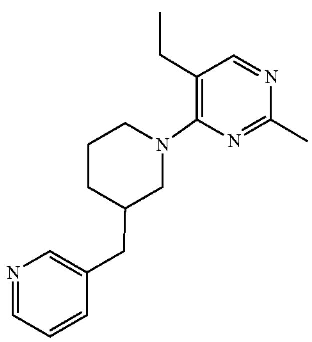 [SMILES: CCc1cnc(C)nc1N1CCCC(Cc2cccnc2)C1] | 1340 (3) | 36.44 (3) | Below Threshold |
| RU-0227215 | 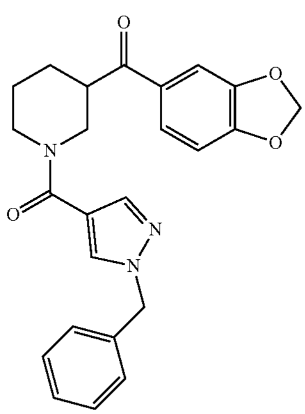 [SMILES: O=C(c1ccc2c(c1)OCO2)C1CCCN(C(=O)c2cnn(Cc3ccccc3)c2)C1] | 1310 (4) | 27.39 (4) | Below Threshold |
| RU-0213635 | 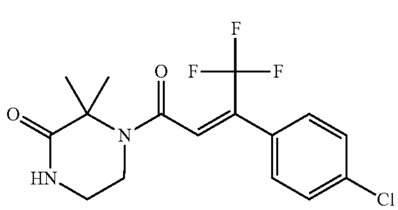 [SMILES: CC1(C)C(=O)NCCN1C(=O)/C=C(/c1ccc(Cl)cc1)C(F)(F)F] | 1170 (5) | 15.00 (14) | Below Threshold |

TABLE 3-continued

Summary of primary screen positives and validated compounds (refers to FIG. 1). Bold = validated in secondary assay.

| RU HTSRC Identifier | Chemical Structure | RFU Score Threshold ≥ 800 (Rank/35) | Fluorescence Z Score Threshold ≥ 10 (Rank/24) | NPA Score Threshold ≥ 5.0 (Rank/20) |
|---|---|---|---|---|
| RU-0223925 | 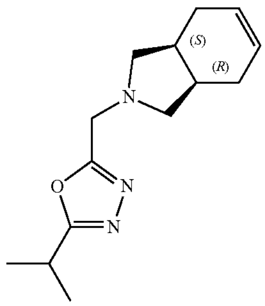 | 1120 (6) | 18.94 (8) | 11.19 (1) |
| RU-0269711 | 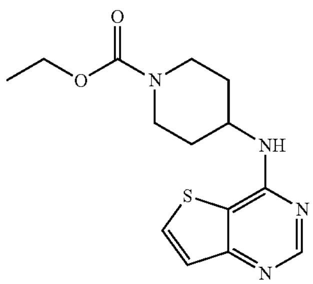 [SMILES: CCOC(=O)N1CCC(Nc2ncnc3ccsc23)CC1] | 1070 (7) | 14.73 (15) | Below Threshold |
| RU-0230205 | 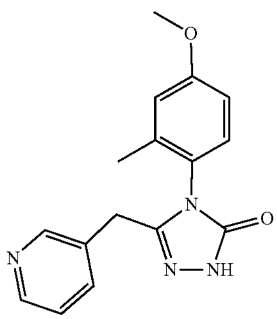 [SMILES: COc1ccc(-n2c(Cc3cccnc3)n[nH]c2=O)c(C)c1] | 1060 (8) | 19.99 (7) | Below Threshold |
| RU-0213672 | 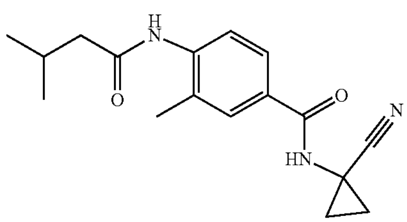 [SMILES: Cc1cc(C(=O)NC2(C#N)CC2)ccc1NC(=O)CC(C)C] | 1040 (9) | 12.15 (20) | Below Threshold |
| RU-0252111 | 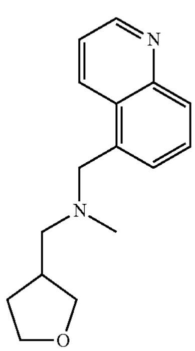 [SMILES: CN(Cc1cccc2ncccc12)CC1CCOC1] | 1010 (10) | 16.48 (12) | Below Threshold |

TABLE 3-continued

Summary of primary screen positives and validated compounds (refers to FIG. 1). Bold = validated in secondary assay.

| RU HTSRC Identifier | Chemical Structure | RFU Score Threshold ≥ 800 (Rank/35) | Fluorescence Z Score Threshold ≥ 10 (Rank/24) | NPA Score Threshold ≥ 5.0 (Rank/20) |
|---|---|---|---|---|
| RU-0248250 | 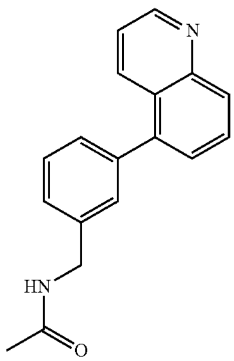 [SMILES: CC(=O)NCc1cccc(-c2cccc3ncccc23)c1] | 1000 (11) | 24.29 (5) | Below Threshold |
| RU-0245007 | 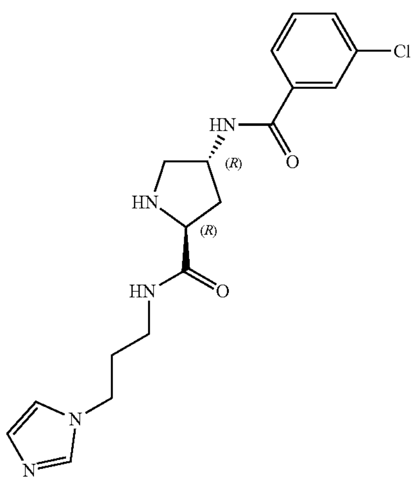 | 993 (12) | 14.31 (17) | Below Threshold |
| RU-0221380 | 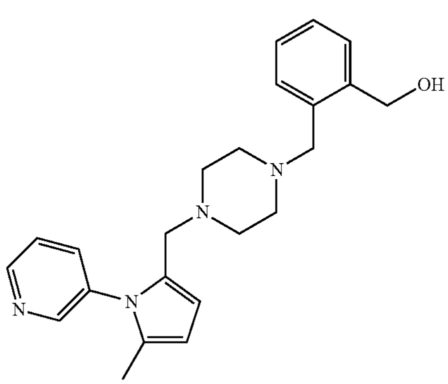 [SMILES: Cc1ccc(CN2CCN(Cc3ccccc3CO)CC2)n1-c1cccnc1] | 922 (13) | 16.89 (11) | Below Threshold |

TABLE 3-continued
Summary of primary screen positives and validated compounds (refers to FIG. 1). Bold = validated in secondary assay.
| RU HTSRC Identifier | Chemical Structure | RFU Score Threshold ≥ 800 (Rank/35) | Fluorescence Z Score Threshold ≥ 10 (Rank/24) | NPA Score Threshold ≥ 5.0 (Rank/20) |
|---|---|---|---|---|
| RU-0228950 | 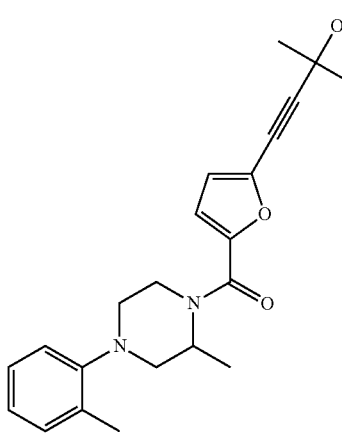 | 921 (14) | 15.58 (13) | Below Threshold |
| RU-0238394 | 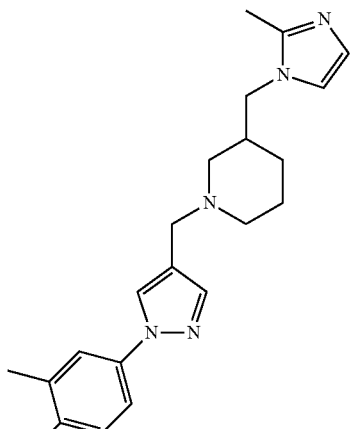 | 914 (15) | 12.45 (19) | 5.54 (11) |
| RU-0259574 | 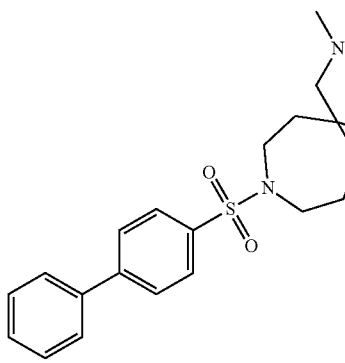 | 903 (16) | Below Threshold | 9.87 (2) |

TABLE 3-continued
Summary of primary screen positives and validated compounds (refers to FIG. 1). Bold = validated in secondary assay.
| RU HTSRC Identifier | Chemical Structure | RFU Score Threshold ≥ 800 (Rank/35) | Fluorescence Z Score Threshold ≥ 10 (Rank/24) | NPA Score Threshold ≥ 5.0 (Rank/20) |
|---|---|---|---|---|
| RU-0224115 | 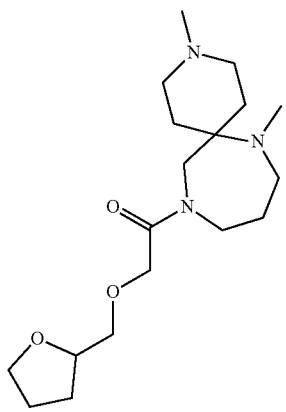 [SMILES: CN1CCC2(CC1)CN(C(=O)COCC1CCCO1)CCCN2C] | 900 (17) | Below Threshold | Below Threshold |
| RU-0261349 | 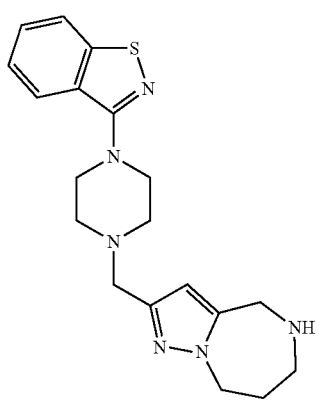 [SMILES: c1ccc2c(N3CCN(Cc4cc5n(n4)CCCNC5)CC3)nsc2c1] | 884 (18) | 11.32 (22) | 5.04 (19) |
| RU-0250475 | 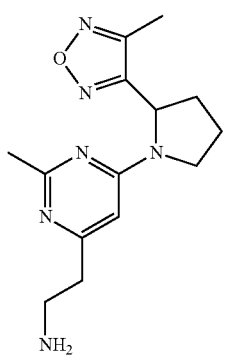 [SMILES: Cc1nc(CCN)cc(N2CCCC2c2nonc2C)n1] | 879 (19) | Below Threshold | Below Threshold |

TABLE 3-continued

Summary of primary screen positives and validated compounds (refers to FIG. 1). Bold = validated in secondary assay.

| RU HTSRC Identifier | Chemical Structure | RFU Score Threshold ≥ 800 (Rank/35) | Fluorescence Z Score Threshold ≥ 10 (Rank/24) | NPA Score Threshold ≥ 5.0 (Rank/20) |
|---|---|---|---|---|
| RU-0246723 | 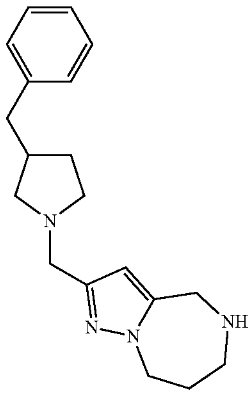 [SMILES: c1ccc(CC2CCN(Cc3cc4n(n3)CCCNC4)C2)cc1] | 873 (20) | 10.91 (23) | Below Threshold |
| RU-0261573 | 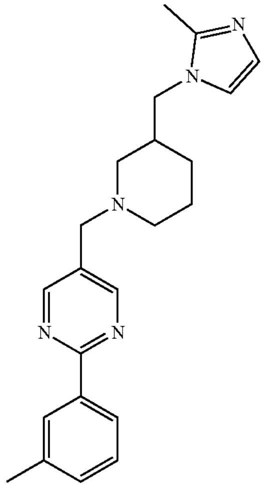 [SMILES: Cc1cccc(-c2ncc(CN3CCCC(Cn4ccnc4C)C3)cn2)c1] | 857 (21) | 10.31 (24) | Below Threshold |
| RU-0159762 | 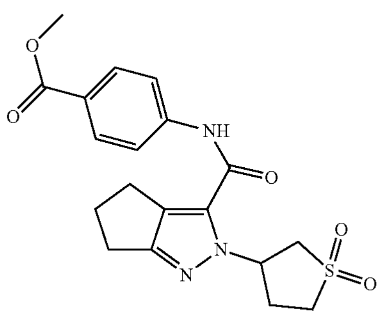 [SMILES: COC(=O)c1ccc(NC(=O)c2c3c(nn2C2CCS(=O)(=O)C2)CCC3)cc1] | 855 (22) | 21.33 (6) | Below Threshold |
| RU-0183032 | 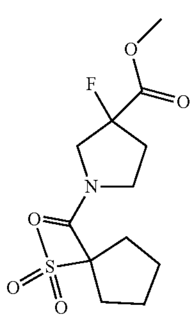 | 855 (22) | Below Threshold | Below Threshold |

TABLE 3-continued

Summary of primary screen positives and validated compounds (refers to FIG. 1). Bold = validated in secondary assay.

| RU HTSRC Identifier | Chemical Structure | RFU Score Threshold ≥ 800 (Rank/35) | Fluorescence Z Score Threshold ≥ 10 (Rank/24) | NPA Score Threshold ≥ 5.0 (Rank/20) |
| --- | --- | --- | --- | --- |
| RU-0242581 | 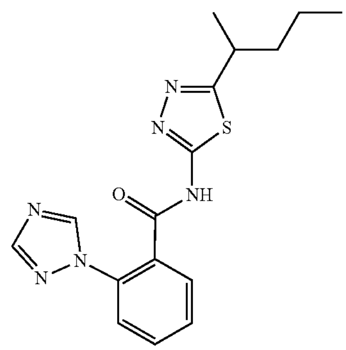 [SMILES: CCCC(C)c1nnc(NC(=O)c2ccccc2-n2cncn2)s1] | 849 (24) | Below Threshold | 5.51 (12) |
| RU-0265172 | 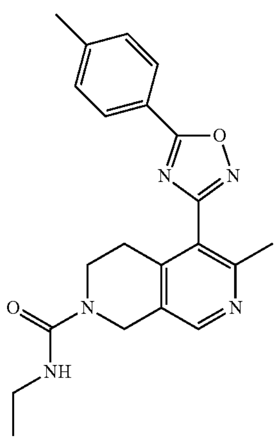 [SMILES: CCNC(=O)N1CCc2c(cnc(C)c2-c2noc(-c3ccc(C)cc3)n2)C1] | 840 (25) | 18.70 (9) | Below Threshold |
| RU-0244068 | 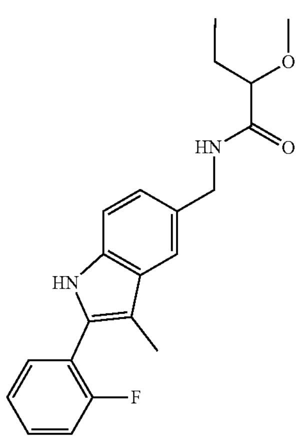 [SMILES: CCC(OC)C(=O)NCc1ccc2[nH]c(-c3ccccc3F)c(C)c2c1] | 836 (26) | Below Threshold | Below Threshold |

TABLE 3-continued

Summary of primary screen positives and validated compounds (refers to FIG. 1). Bold = validated in secondary assay.

| RU HTSRC Identifier | Chemical Structure | RFU Score Threshold ≥ 800 (Rank/35) | Fluorescence Z Score Threshold ≥ 10 (Rank/24) | NPA Score Threshold ≥ 5.0 (Rank/20) |
|---|---|---|---|---|
| RU-0236543 | 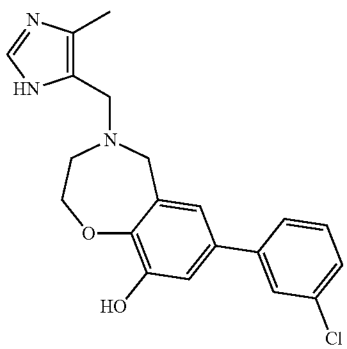 [SMILES: Cc1nc[nH]c1CN1CCOc2c(O)cc(-c3cccc(Cl)c3)cc2C1] | 821 (27) | Below Threshold | Below Threshold |
| RU-0219355 | 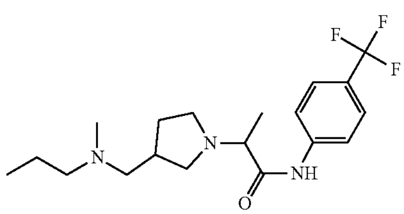 [SMILES: CCCN(C)CC1CCN(C(C)C(=O)Nc2ccc(C(F)(F)F)cc2)C1] | 819 (28) | Below Threshold | 6.14 (5) |
| RU-0244443 | 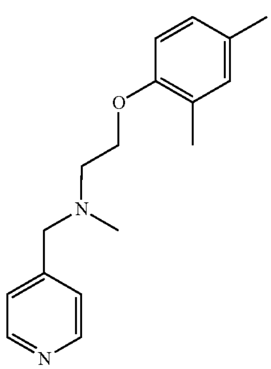 [SMILES: Cc1ccc(OCCN(C)Cc2ccncc2)c(C)c1] | 818 (29) | Below Threshold | Below Threshold |
| RU-0227959 | 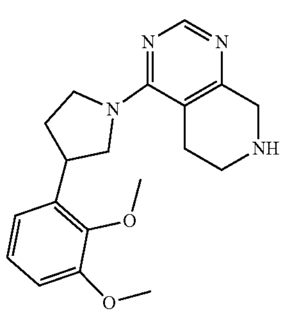 [SMILES: COc1cccc(C2CCN(c3ncnc4c3CCNC4)C2)c1OC] | 815 (30) | Below Threshold | Below Threshold |

TABLE 3-continued

Summary of primary screen positives and validated compounds (refers to FIG. 1). Bold = validated in secondary assay.

| RU HTSRC Identifier | Chemical Structure | RFU Score Threshold ≥ 800 (Rank/35) | Fluorescence Z Score Threshold ≥ 10 (Rank/24) | NPA Score Threshold ≥ 5.0 (Rank/20) |
|---|---|---|---|---|
| RU-0220454 | 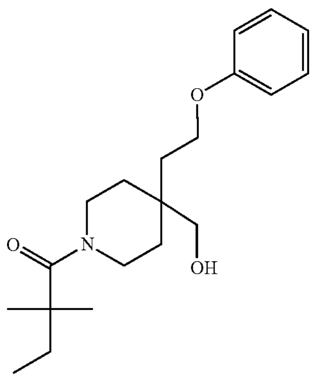 [SMILES: CCC(C)(C)C(=O)N1CCC(CO)(CCOc2ccccc2)CC1] | 811 (31) | Below Threshold | Below Threshold |
| RU-0236855 | 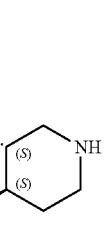 | 810 (32) | Below Threshold | Below Threshold |
| RU-0239453 | 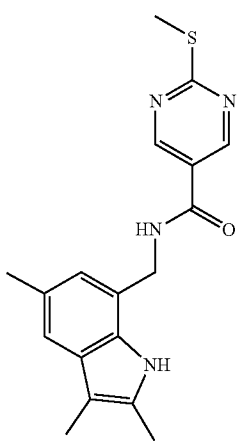 [SMILES: CSc1ncc(C(=O)NCc2cc(C)cc3c(C)c(C)[nH]c23)cn1] | 809 (33) | Below Threshold | Below Threshold |
| RU-0225107 | 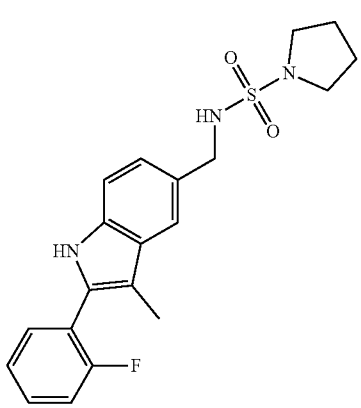 [SMILES: Cc1c(-c2ccccc2F)[nH]c2ccc(CNS(=O)(=O)N3CCCC3)cc12] | 805 (34) | Below Threshold | 5.07 (18) |

TABLE 3-continued

Summary of primary screen positives and validated compounds (refers to FIG. 1). Bold = validated in secondary assay.

| RU HTSRC Identifier | Chemical Structure | RFU Score Threshold ≥ 800 (Rank/35) | Fluorescence Z Score Threshold ≥ 10 (Rank/24) | NPA Score Threshold ≥ 5.0 (Rank/20) |
|---|---|---|---|---|
| RU-0232318 | 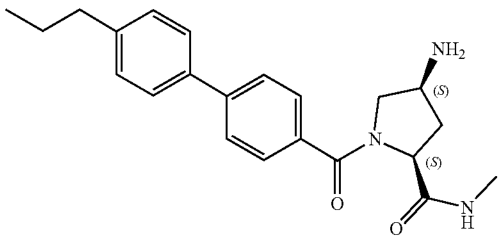 | 804 (35) | Below Threshold | Below Threshold |
| RU-0007138 | 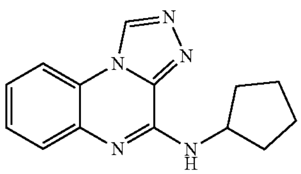 [SMILES: c1ccc2c(c1)nc(NC1CCCC1)c1nncn12] | Below Threshold | 17.92 (10) | Below Threshold |
| RU-0254439 | 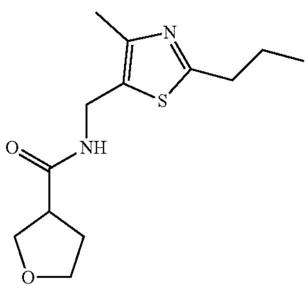 [SMILES: CCCc1nc(C)c(CNC(=O)C2CCOC2)s1] | Below Threshold | 14.37 (16) | Below Threshold |
| RU-0227303 | 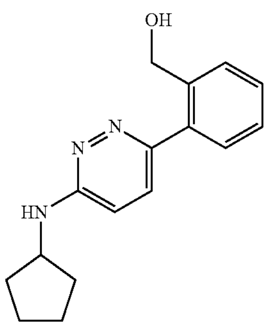 [SMILES: OCc1ccccc1-c1ccc(NC2CCCC2)nn1] | Below Threshold | 13.68 (18) | Below Threshold |
| RU-0257787 | 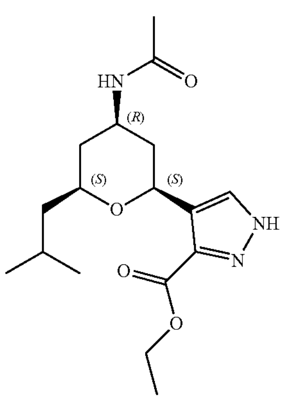 | Below Threshold | 12.09 (21) | Below Threshold |

TABLE 3-continued

Summary of primary screen positives and validated compounds (refers to FIG. 1). Bold = validated in secondary assay.

| RU HTSRC Identifier | Chemical Structure | RFU Score Threshold ≥ 800 (Rank/35) | Fluorescence Z Score Threshold ≥ 10 (Rank/24) | NPA Score Threshold ≥ 5.0 (Rank/20) |
|---|---|---|---|---|
| RU-0256394 | 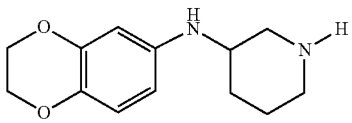 [SMILES: c1cc2c(cc1NC1CCCNC1)OCCO2] | Below Threshold | Below Threshold | 5.87 (6) |
| RU-0268068 | 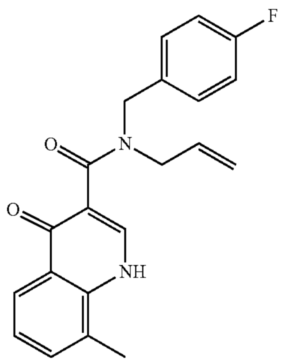 [SMILES: C=CCN(Cc1ccc(F)cc1)C(=O)c1c[nH]c2c(C)cccc2c1=O] | Below Threshold | Below Threshold | 5.81 (7) |
| RU-0242925 | 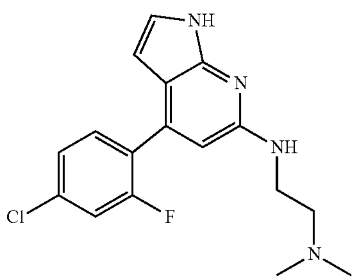 [SMILES: CN(C)CCNc1cc(-c2ccc(Cl)cc2F)c2cc[nH]c2n1] | Below Threshold | Below Threshold | 5.73 (8) |
| RU-0219256 | 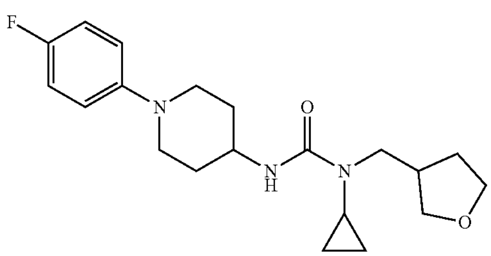 [SMILES: O=C(NC1CCN(c2ccc(F)cc2)CC1)N(CC1CCOC1)C1CC1] | Below Threshold | Below Threshold | 5.69 (9) |
| RU-0201425 | 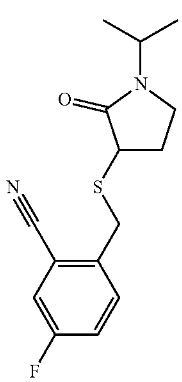 [SMILES: CC(C)N1CCC(SCc2ccc(F)cc2C#N)C1=O] | Below Threshold | Below Threshold | 5.69 (9) |

TABLE 3-continued

Summary of primary screen positives and validated compounds (refers to FIG. 1). Bold = validated in secondary assay.

| RU HTSRC Identifier | Chemical Structure | RFU Score Threshold ≥ 800 (Rank/35) | Fluorescence Z Score Threshold ≥ 10 (Rank/24) | NPA Score Threshold ≥ 5.0 (Rank/20) |
|---|---|---|---|---|
| RU-0243566 | 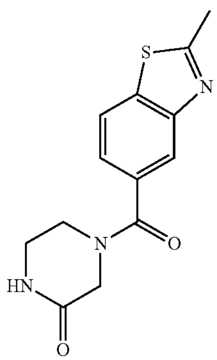 [SMILES: Cc1nc2cc(C(=O)N3CCNC(=O)C3)ccc2s1] | Below Threshold | Below Threshold | 5.55 (11) |
| RU-0231961 | 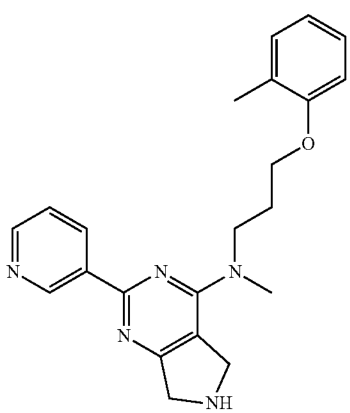 [SMILES: Cc1ccccc1OCCCN(C)c1nc(-c2cccnc2)nc2c1CNC2] | Below Threshold | Below Threshold | 5.50 (13) |
| RU-0250369 | 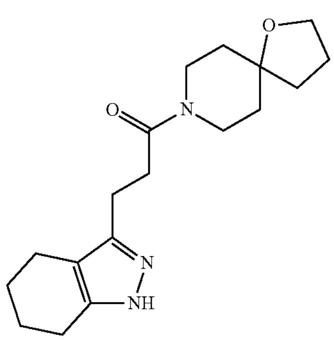 [SMILES: O=C(CCc1n[nH]c2c1CCCC2)N1CCC2(CCCO2)CC1] | Below Threshold | Below Threshold | 5.46 (14) |
| RU-0262489 | 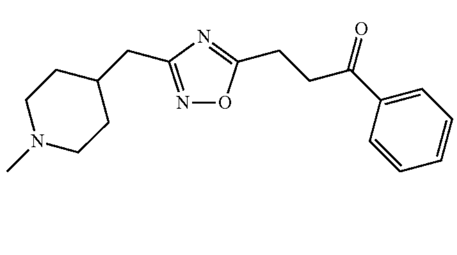 [SMILES: CN1CCC(Cc2noc(CCC(=O)c3ccccc3)n2)CC1] | Below Threshold | Below Threshold | 5.43 (15) |

TABLE 3-continued

Summary of primary screen positives and validated compounds (refers to FIG. 1). Bold = validated in secondary assay.

| RU HTSRC Identifier | Chemical Structure | RFU Score Threshold ≥ 800 (Rank/35) | Fluorescence Z Score Threshold ≥ 10 (Rank/24) | NPA Score Threshold ≥ 5.0 (Rank/20) |
|---|---|---|---|---|
| RU-0236897 | 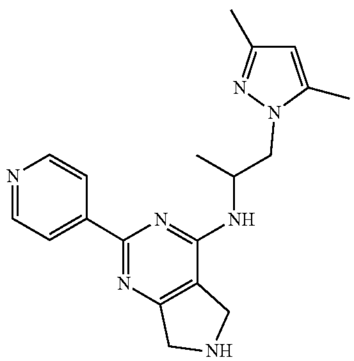 [SMILES: Cc1cc(C)n(CC(C)Nc2nc(-c3ccncc3)nc3c2CNC3)n1] | Below Threshold | Below Threshold | 5.32 (16) |
| RU-0239646 | 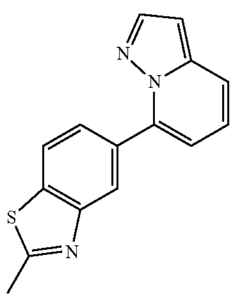 [SMILES: Cc1nc2cc(-c3cccc4ccnn34)ccc2s1] | Below Threshold | Below Threshold | 5.22 (17) |
| RU-0221236 | 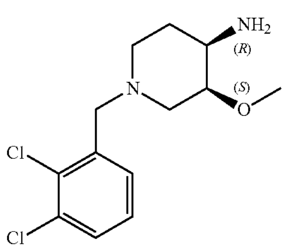 | Below Threshold | Below Threshold | 5.13 (18) |
| RU-0221613 | 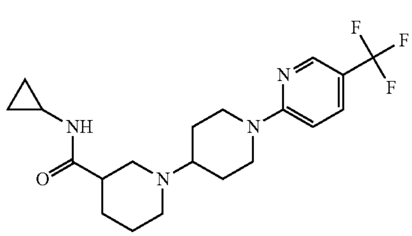 [SMILES: O=C(NC1CC1)C1CCCN(C2CCN(c3ccc(C(F)(F)F)cn3)CC2)C1] | Below Threshold | Below Threshold | 5.00 (20) |

TABLE 4

*Properties of compounds validated in secondary screen (Refers to FIG. 1).*

| RU HTSRC Identifier | Compound Structure | Compound Name | Measured $EC_{50}$ |
|---|---|---|---|
| RU-0226606 | 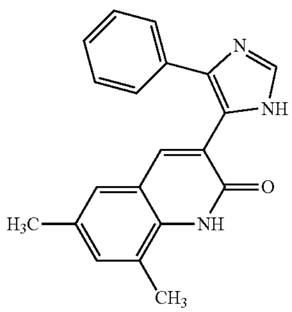 [SMILES: Cc1cc(C)c2[nH]c(=O)c(-c3[nH]cnc3-c3ccccc3)cc2c1] | 6,8-dimethyl-3-(4-phenyl-1H-imidazol-5-yl)quinolin-2(1H)-one $C_{20}H_{17}N_3O$ 315 g/mol | 8.6 μM |
| RU-0238003 | 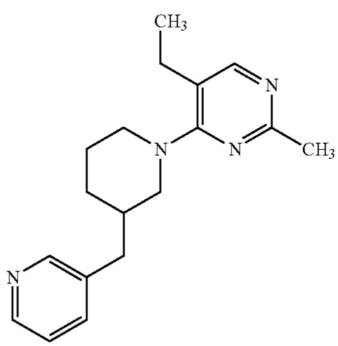 [SMILES: CCc1cnc(C)nc1N1CCCC(Cc2cccnc2)C1] | 5-ethyl-2-methyl-4-[3-(pyridin-3-ylmethyl)piperidin-1-yl]pyrimidine $C_{18}H_{24}N_4$ 296 g/mol | >40 μM |
| RU-0269711 | 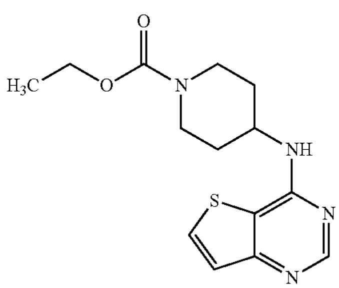 [SMILES: CCOC(=O)N1CCC(Nc2ncnc3ccsc23)CC1] | ethyl 4-(thieno[2,3-e]pyrimidin-4-ylamino)piperidine-1-carboxylate $C_{14}H_{18}N_4O_2S$ 306 g/mol | 28.3 μM |
| RU-0248250 | 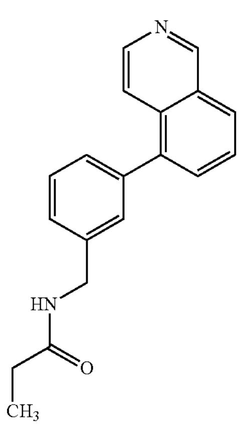 [SMILES: CCC(=O)NCc1cccc(-c2cccc3cnccc23)c1] | N-(3-isoquinolin-5-ylbenzyl)propanamide $C_{19}H_{18}N_2O$ 290 g/mol | >40 μM |

TABLE 5

Structure-activity relationship analysis of library and proprietary chemical analogs (Refers to FIG.1).

Figure 11:
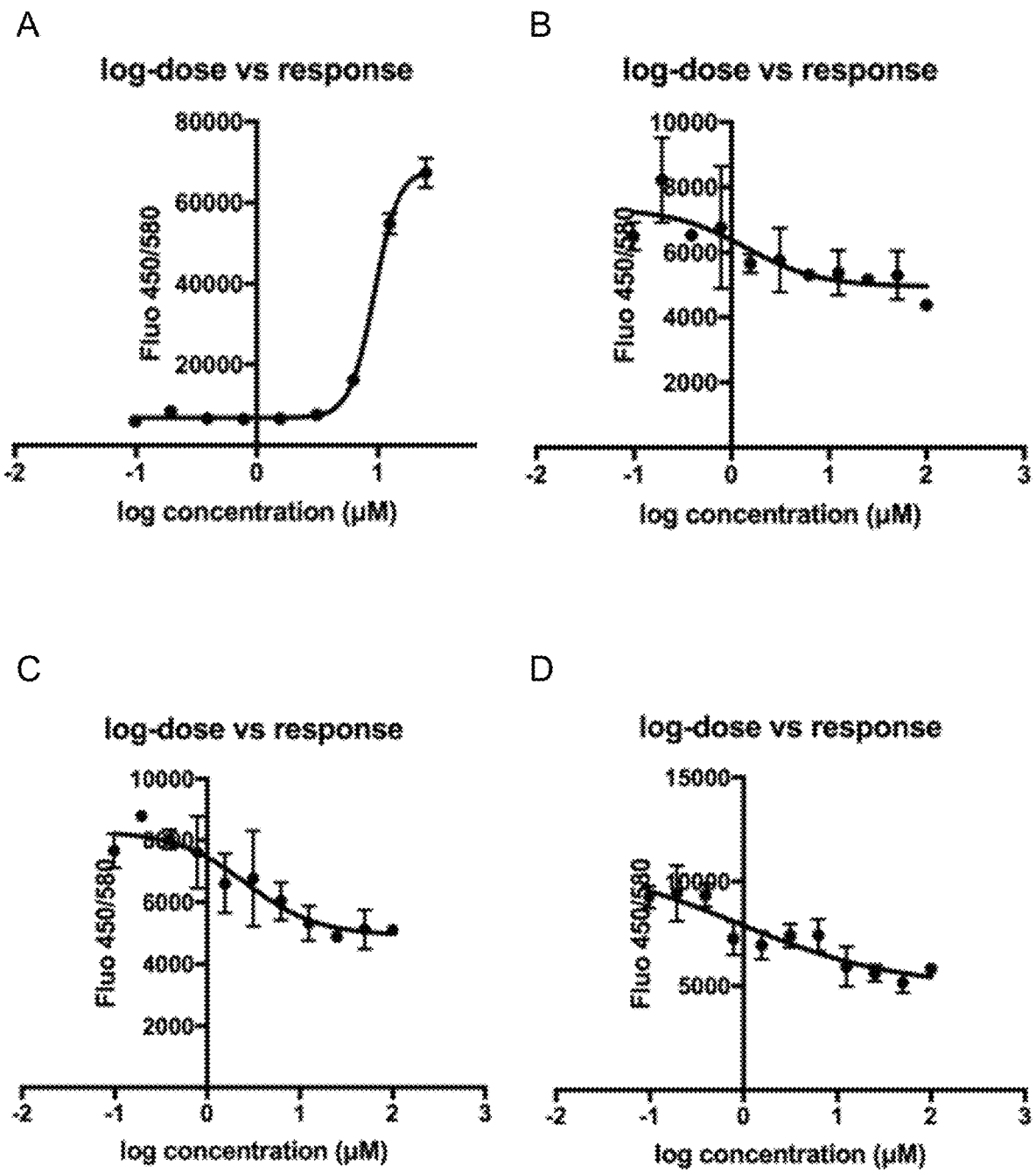
FIG. 11. Dose response plots as shown in Table 5. (A) Dose response plot of RU-0226606 (DIPQUO). (B) Dose response plot of RU-0266582. (C) Dose response plot of RU-0220396. (D) Dose response plot of BT344. (E) Dose response plot of BT345. (F) Dose response plot of BT350. (G) Dose response plot of BT351. (H) Dose response plot of BT353.
Figure 11:
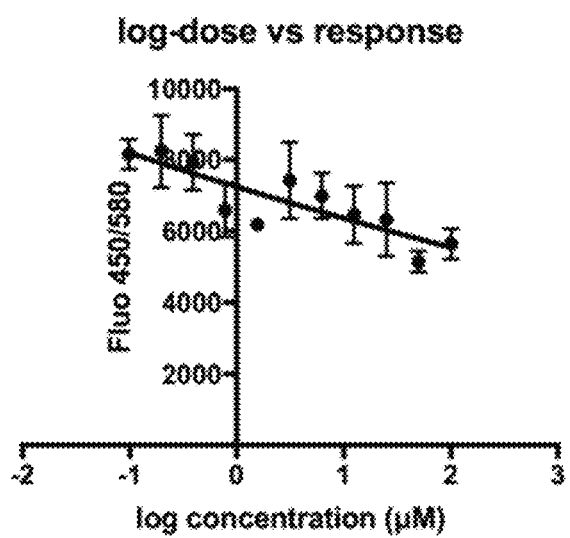
Figure 11:
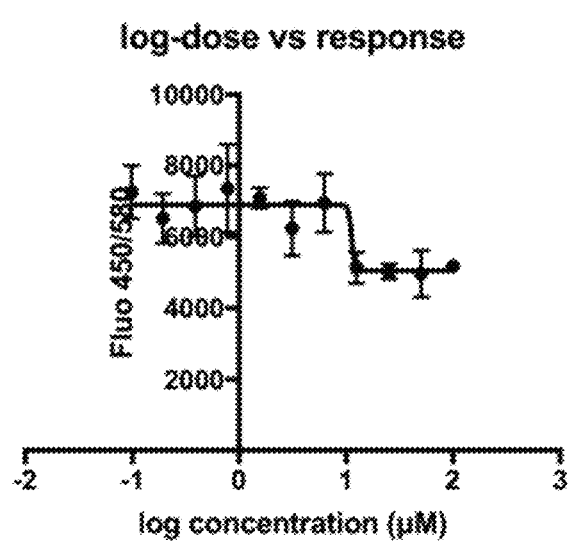
Figure 11:
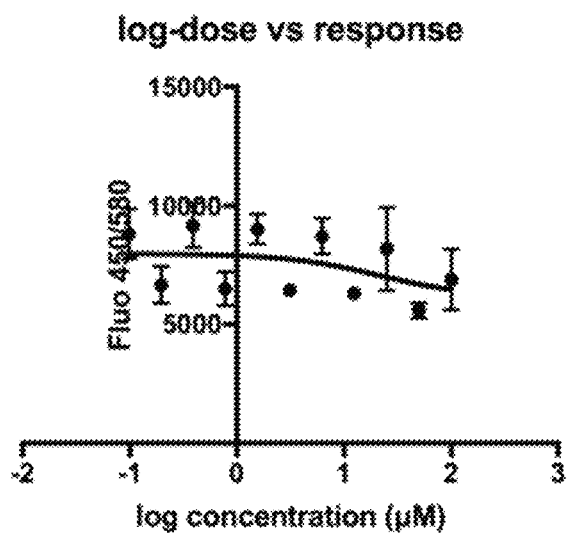
Figure 11:
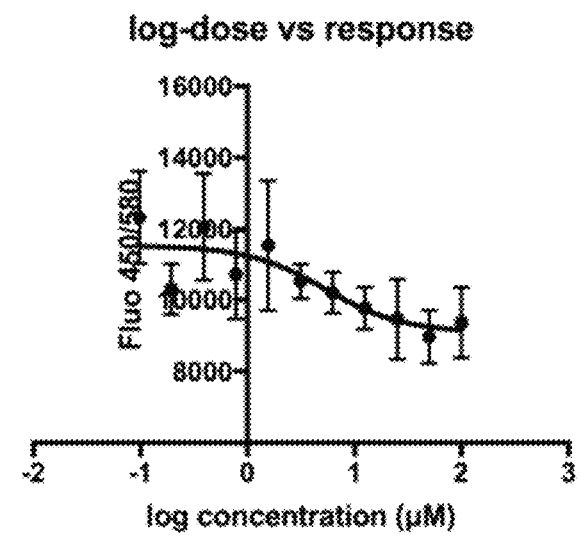

| Identifier | Compound Structure | Dose Response (shown in FIG. 11) | $EC_{50}$ Fluo. Z Score Significance |
|---|---|---|---|
| RU-0226606 (DIPQUO) | 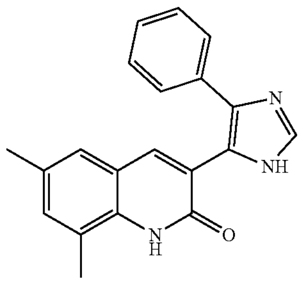 [SMILES: Cc1cc(C)c2[nH]c(=O)c(-c3[nH]cnc3-c3ccccc3)cc2c1] | (A) | 9.3 μM<br>34.56 ± 1.80<br>p < 10.000 |
| RU-0266582 | 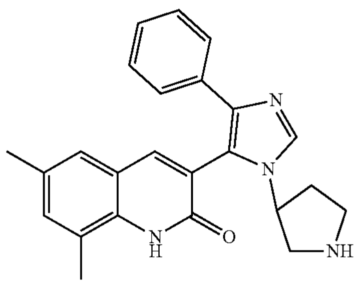 [SMILES: Cc1cc(C)c2[nH]c(=O)c(-c3c(-c4ccccc4)ncn3C3CCNC3)cc2c1] | (B) | 1.42 μM<br>0.48 ± 1.10<br>n.s. |
| RU-0220396 | 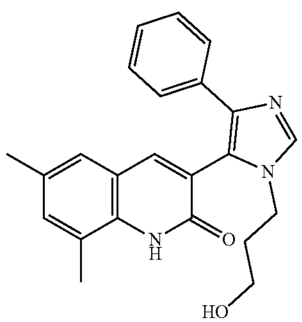 [SMILES: Cc1cc(C)c2[nH]c(=O)c(-c3c(-c4ccccc4)ncn3CCCO)cc2c1] | (C) | 2.63 μM<br>−0.3 ± 0.20<br>n.s. |
| BT344 | 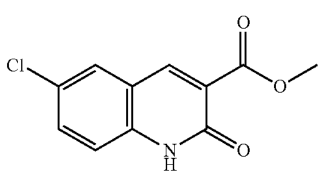 [SMILES: COC(=O)c1cc2cc(Cl)ccc2[nH]c1=O] | (D) | 0.92 μM<br>0.61 ± 0.47<br>n.s. |
| BT345 | 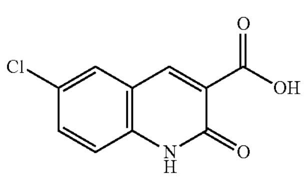 [SMILES: O=C(O)c1cc2cc(Cl)ccc2[nH]c1=O] | (E) | n/a |
| BT350 | 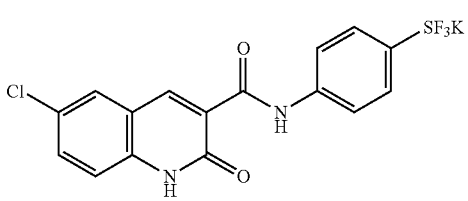 | (F) | 11.24 μM<br>0.61 ± 0.58<br>n.s. |

TABLE 5-continued

Structure-activity relationship analysis of library and proprietary chemical analogs (Refers to FIG.1).

| Identifier | Compound Structure | Dose Response (shown in FIG. 11) | $EC_{50}$ Fluo. Z Score Significance |
|---|---|---|---|
| BT351 | 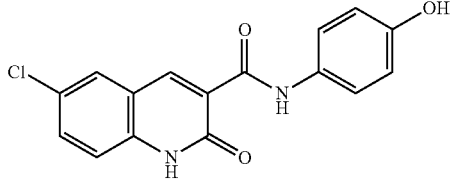 [SMILES: O=C(Nc1ccc(O)cc1)c1cc2cc(Cl)ccc2[nH]c1=O] | (G) | 20.87 μM<br>1.48 ± 1.26<br>n.s. |
| BT353 | 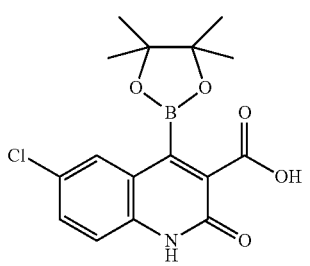 [SMILES: CC1(C)OB(c2c(C(=O)O)c(=O)[nH]c3ccc(Cl)cc23)OC1(C)C] | (H) | 5.31 μM<br>3.15 ± 0.34<br>p = 0.0004 |

TABLE 6

Structure-activity relationship analysis of chemical analogs (Refers to FIG. 1).

| Identifier | Compound Structure | RFU Score (10 μM) | % Activation |
|---|---|---|---|
| RU-0226606 (DIPQUO) Positive Control | 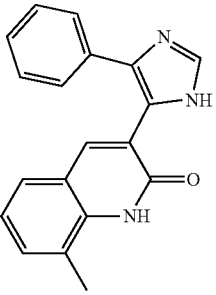 | 3104 | 100 |
| DMSO Negative Control | 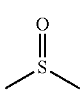 | 384 | n/a |
| RU-0424558 | 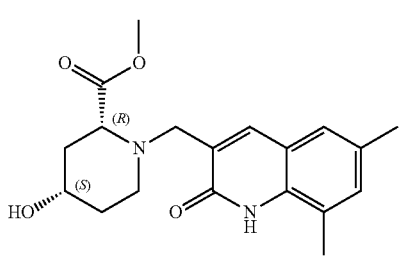 | 399 | 4.15 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424557 | 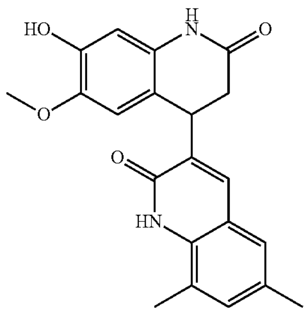 | 430 | 5.24 |
| RU-0424556 | 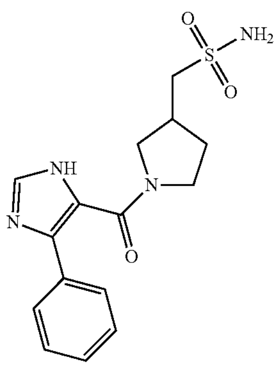 [SMILES: NS(=O)(=O)CC1CCN(C(=O)c2[nH]cnc2-c2ccccc2)C1] | 435 | 5.40 |
| RU-0424555 | 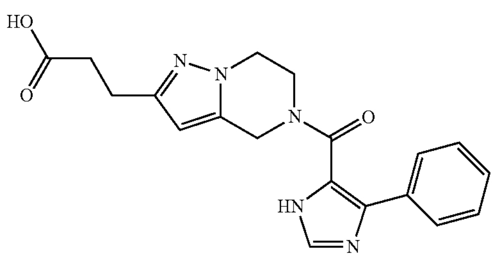 [SMILES: O=C(O)CCc1cc2n(n1)CCN(C(=O)c1[nH]cnc1-c1ccccc1)C2] | 443 | 5.68 |
| RU-0424554 | 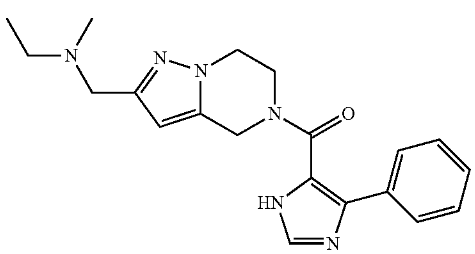 [SMILES: CCN(C)Cc1cc2n(n1)CCN(C(=O)c1[nH]cnc1-c1ccccc1)C2] | 409 | 4.50 |
| RU-0424553 | 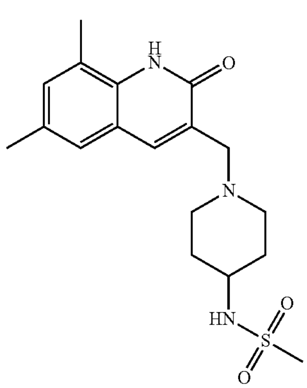 | 454 | 6.08 |

TABLE 6-continued

Structure-activity relationship analysis of chemical analogs (Refers to FIG. 1).

| Identifier | Compound Structure | RFU Score (10 μM) | % Activation |
| --- | --- | --- | --- |
| RU-0424552 | 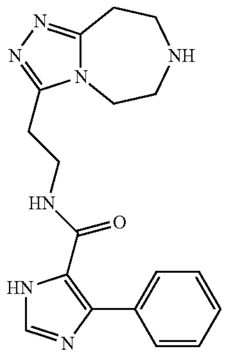 [SMILES: O=C(NCCc1nnc2n1CCNCC2)c1[nH]cnc1-c1ccccc1] | 485 | 7.18 |
| RU-0424551 | 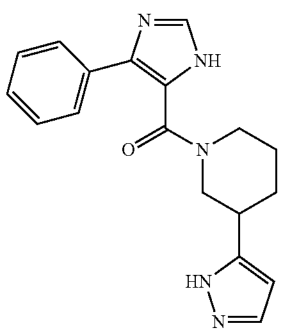 [SMILES: O=C(c1[nH]cnc1-c1ccccc1)N1CCCC(c2ccn[nH]2)C1] | 452 | 6.00 |
| RU-0424550 | 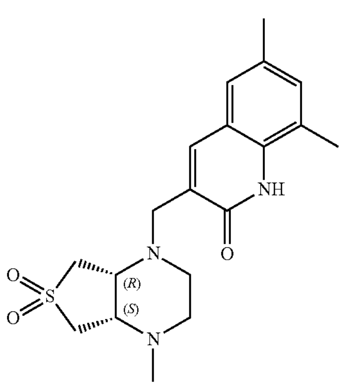 | 304 | 0.78 |
| RU-0424549 | 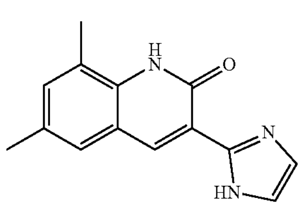 [SMILES: Cc1cc(C)c2[nH]c(=O)c(-c3ncc[nH]3)cc2c1] | 445 | 5.75 |

TABLE 6-continued
Structure-activity relationship analysis of chemical analogs (Refers to FIG. 1).
| Identifier | Compound Structure | RFU Score (10 μM) | % Activation |
|---|---|---|---|
| RU-0424548 | 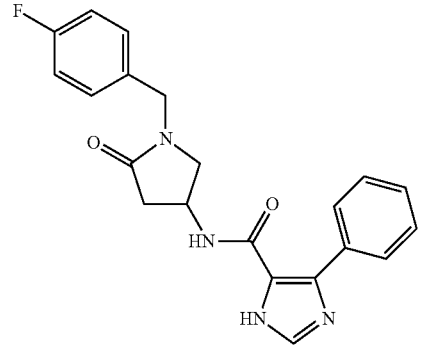 [SMILES: O=C(NC1CC(=O)N(Cc2ccc(F)cc2)C1)c1[nH]cnc1-c1ccccc1] | 467 | 6.54 |
| RU-0424547 | 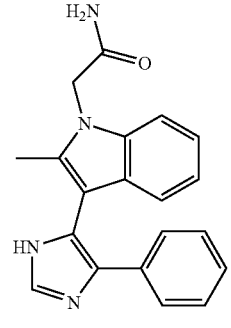 [SMILES: Cc1c(-c2[nH]cnc2-c2ccccc2)c2ccccc2n1CC(N)=O] | 518 | 8.34 |
| RU-0424546 | 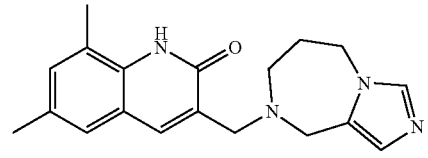 [SMILES: Cc1cc(C)c2[nH]c(=O)c(CN3CCCn4cncc4C3)cc2c1] | 460 | 6.30 |
| RU-0424545 | 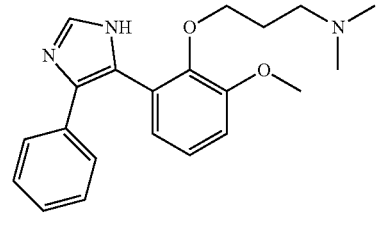 [SMILES: COc1cccc(-c2[nH]cnc2-c2ccccc2)c1OCCCN(C)C] | 433 | 5.33 |
| RU-0424544 | 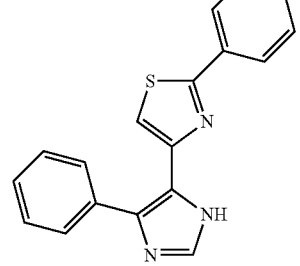 | 450 | 5.93 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424543 | 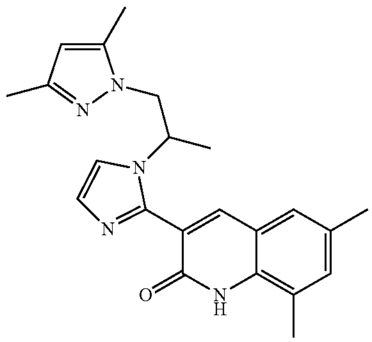 | 363 | 2.86 |
| RU-0424542 | 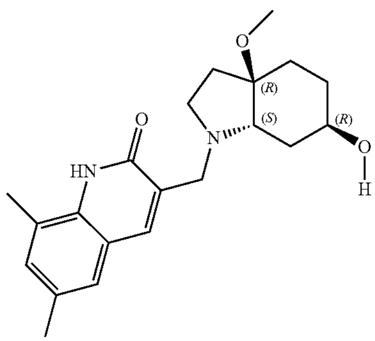 | 641 | 12.7 |
| RU-0424541 | 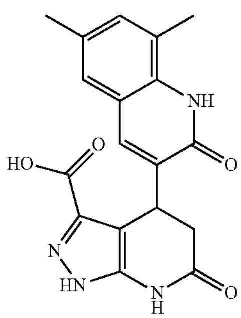 [SMILES: Cc1cc(C)c2[nH]c(=O)c(C3CC(=O)Nc4[nH]nc(C(=O)O)c43)cc2c1] | 646 | 12.9 |
| RU-0424540 | 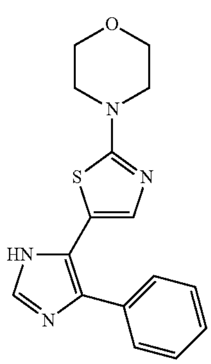 [SMILES: c1ccc(-c2nc[nH]c2-c2cnc(N3CCOCC3)s2)cc1] | 603 | 11.4 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424539 | 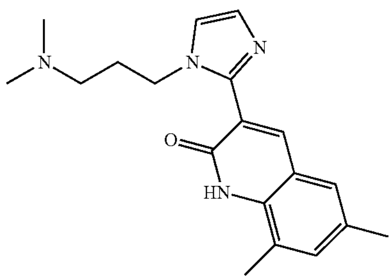 | 565 | 10.0 |
| RU-0424538 | 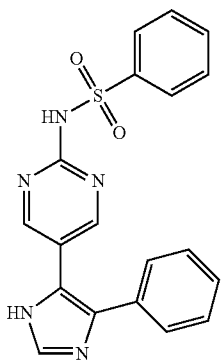 [SMILES: O=S(=O)(Nc1ncc(-c2[nH]cnc2-c2ccccc2)cn1)c1ccccc1] | 533 | 8.87 |
| RU-0424537 | 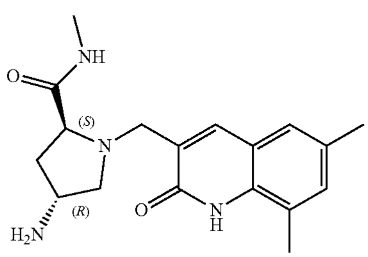 | 513 | 8.16 |
| RU-0424536 | 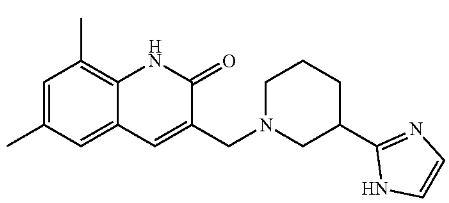 [SMILES: Cc1cc(C)c2[nH]c(=O)c(CN3CCCC(c4ncc[nH]4)C3)cc2c1] | 516 | 8.27 |
| RU-0424535 | 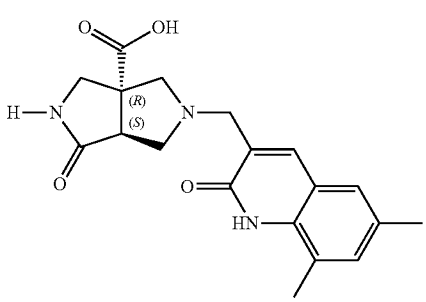 | 518 | 8.32 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424534 | 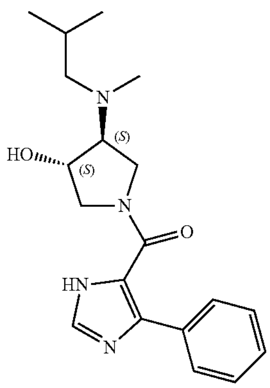 | 638 | 12.6 |
| RU-0424533 | 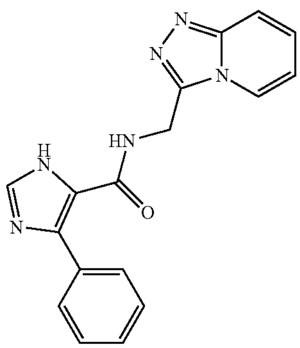 [SMILES: O=C(NCc1nnc2ccccn12)c1[nH]cnc1-c1ccccc1] | 607 | 11.5 |
| RU-0424532 | 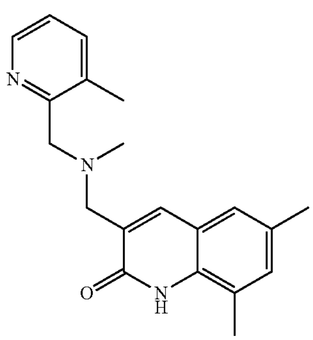 [SMILES: Cc1cc(C)c2[nH]c(=O)c(CN(C)Cc3ncccc3C)cc2c1] | 627 | 12.2 |
| RU-0424531 | 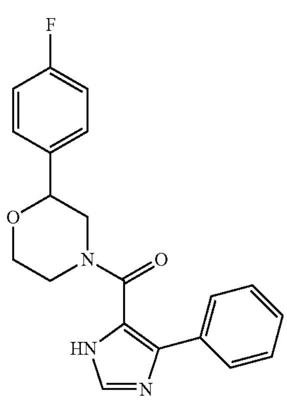 [SMILES: O=C(c1[nH]cnc1-c1ccccc1)N1CCOC(c2ccc(F)cc2)C1] | 478 | 6.93 |

TABLE 6-continued

Structure-activity relationship analysis of chemical analogs (Refers to FIG. 1).

| Identifier | Compound Structure | RFU Score (10 μM) | % Activation |
| --- | --- | --- | --- |
| RU-0424530 | 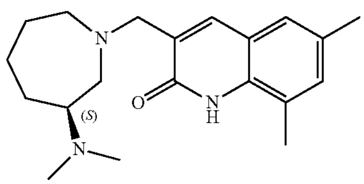 | 524 | 8.55 |
| RU-0424529 | 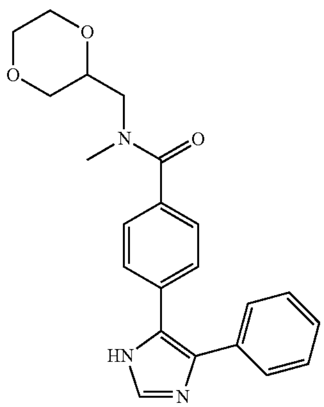 [SMILES: CN(CC1COCCO1)C(=O)c1ccc(-c2[nH]cnc2-c2ccccc2)cc1] | 504 | 7.85 |
| RU-0424528 | 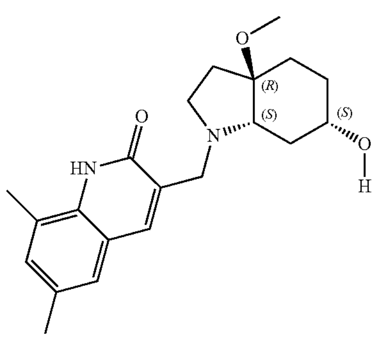 | 538 | 9.03 |
| RU-0424527 | 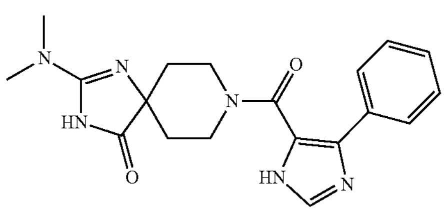 [SMILES: CN(C)C1=NC2(CCN(C(=O)c3[nH]cnc3-c3ccccc3)CC2)C(=O)N1] | 575 | 10.5 |
| RU-0424526 | 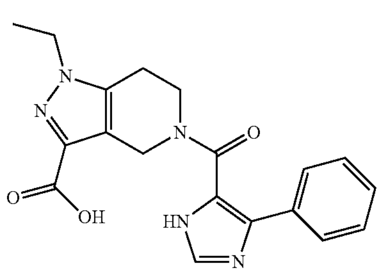 [SMILES: CCn1nc(C(=O)O)c2c1CCN(C(=O)c1[nH]cnc1-c1ccccc1)C2] | 545 | 9.28 |

TABLE 6-continued
Structure-activity relationship analysis of chemical analogs (Refers to FIG. 1).
| Identifier | Compound Structure | RFU Score (10 μM) | % Activation |
|---|---|---|---|
| RU-0424525 | 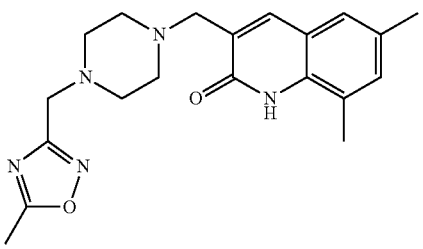 | 563 | 9.94 |
| RU-0424524 | 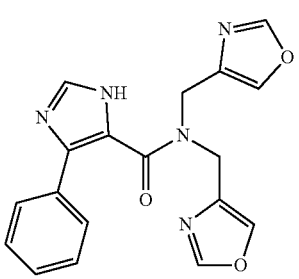 [SMILES: O=C(c1[nH]cnc1-c1ccccc1)N(Cc1cocn1)Cc1cocn1] | 549 | 9.42 |
| RU-0424523 | 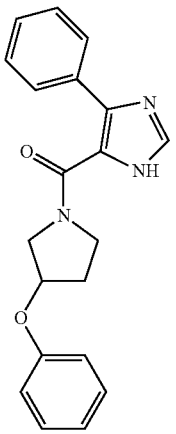 [SMILES: O=C(c1[nH]cnc1-c1ccccc1)N1CCC(Oc2ccccc2)C1] | 419 | 4.84 |
| RU-0424522 | 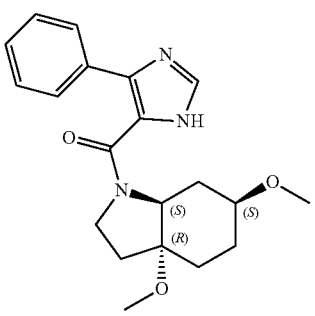 | 458 | 6.21 |
| RU-0424521 | 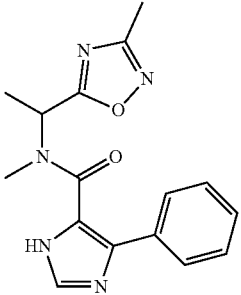 [SMILES: Cc1noc(C(C)N(C)C(=O)c2[nH]cnc2-c2ccccc2)n1] | 604 | 11.33 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424520 | 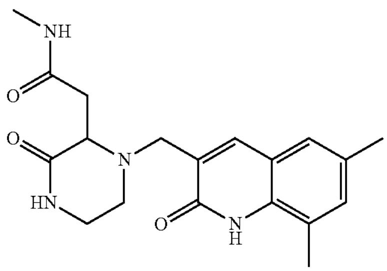 [SMILES: CNC(=O)CC1C(=O)NCCN1Cc1cc2cc(C)cc(C)c2[nH]c1=O] | 532 | 8.81 |
| RU-0424519 | 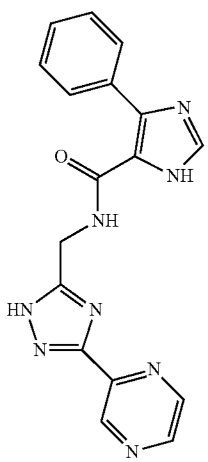 [SMILES: O=C(NCc1nc(-c2cnccn2)n[nH]1)c1[nH]cnc1-c1ccccc1] | 561 | 9.84 |
| RU-0424518 | 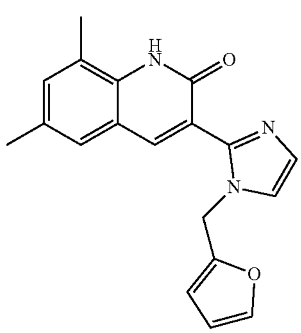 [SMILES: Cc1cc(C)c2[nH]c(=O)c(-c3nccn3Cc3ccco3)cc2c1] | 484 | 7.14 |
| RU-0424517 | 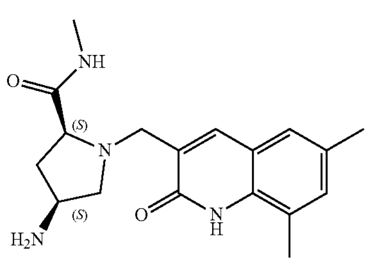 | 527 | 8.64 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424516 | 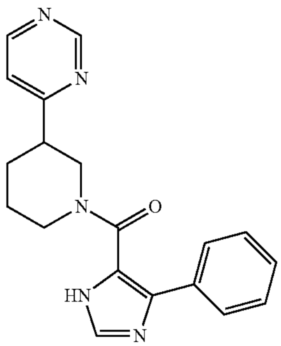 [SMILES: O=C(c1[nH]cnc1-c1ccccc1)N1CCCC(c2ccncn2)C1] | 392 | 3.89 |
| RU-0424515 | 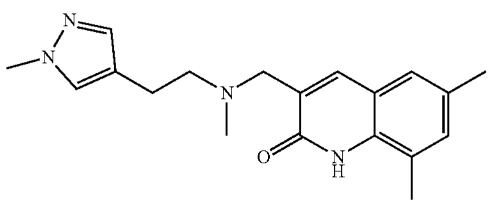 | 314 | 1.16 |
| RU-0424514 | 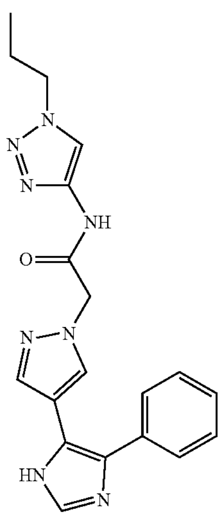 [SMILES: CCCn1cc(NC(=O)Cn2cc(-c3[nH]cnc3-c3ccccc3)cn2)nn1] | 386 | 3.69 |
| RU-0424513 | 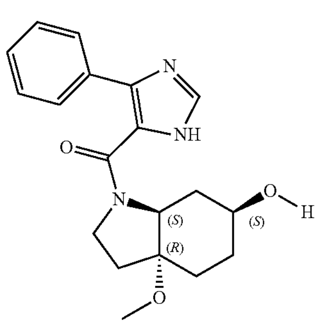 | 435 | 5.42 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424512 | 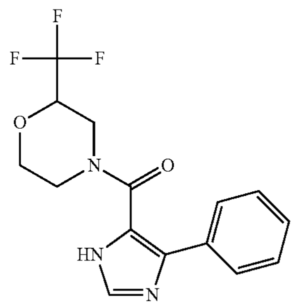 [SMILES: O=C(c1[nH]cnc1-c1ccccc1)N1CCOC(C(F)(F)F)C1] | 455 | 6.12 |
| RU-0424511 | 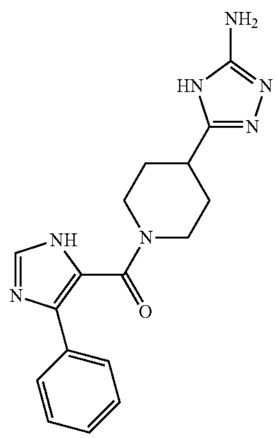 [SMILES: Nc1nnc(C2CCN(C(=O)c3[nH]cnc3-c3ccccc3)CC2)[nH]1] | 467 | 6.54 |
| RU-0424510 | 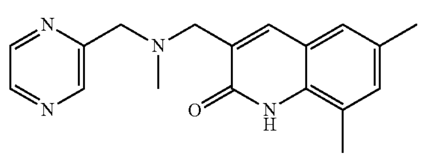 [SMILES: Cc1cc(C)c2[nH]c(=O)c(CN(C)Cc3cnccn3)cc2c1] | 484 | 7.14 |
| RU-0424509 | 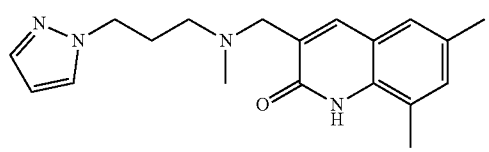 [SMILES: Cc1cc(C)c2[nH]c(=O)c(CN(C)CCCn3cccn3)cc2c1] | 486 | 7.19 |
| RU-0424508 | 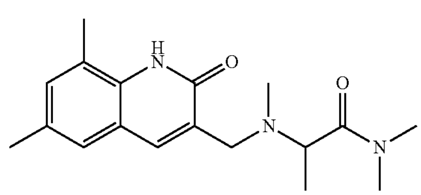 | 504 | 7.85 |
| RU-0424507 | 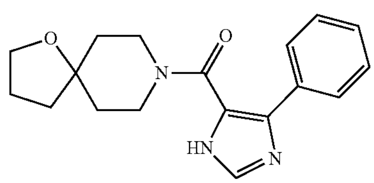 [SMILES: O=C(c1[nH]cnc1-c1ccccc1)N1CCC2(CCCO2)CC1] | 366 | 2.99 |

TABLE 6-continued
Structure-activity relationship analysis of chemical analogs (Refers to FIG. 1).
| Identifier | Compound Structure | RFU Score (10 μM) | % Activation |
|---|---|---|---|
| RU-0424506 | 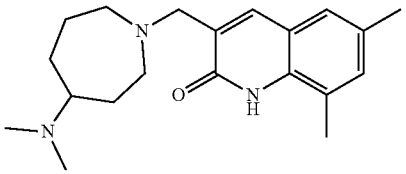 | 364 | 2.90 |
| RU-0424505 | 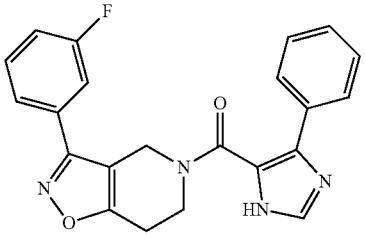 [SMILES: O=C(c1[nH]cnc1-c1ccccc1)N1CCc2onc(-c3cccc(F)c3)c2C1] | 326 | 1.56 |
| RU-0424504 | 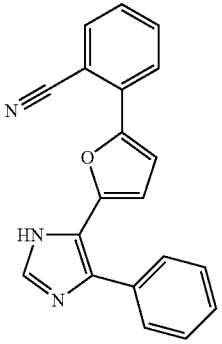 [SMILES: N#Cc1ccccc1-c1ccc(-c2[nH]cnc2-c2ccccc2)o1] | 309 | 0.96 |
| RU-0424503 | 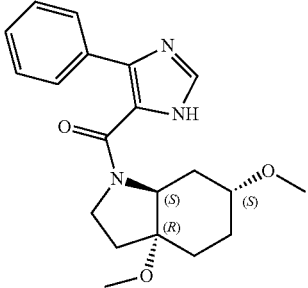 | 436 | 5.45 |
| RU-0424502 | 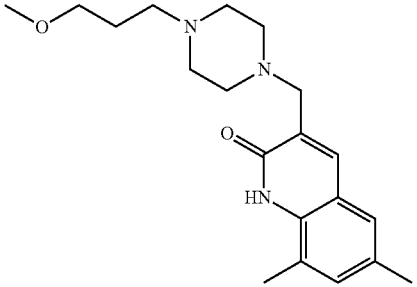 | 502 | 7.78 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424501 | 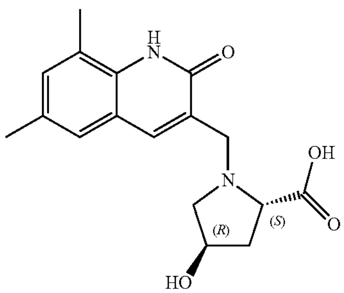 | 487 | 7.25 |
| RU-0424500 | 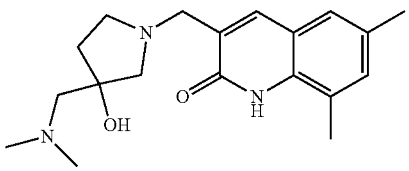 | 523 | 8.52 |
| RU-0424499 | 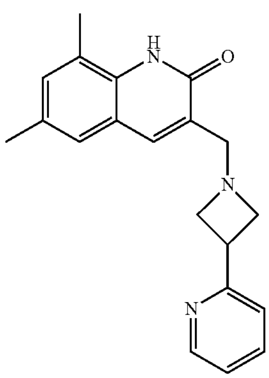 [SMILES: Cc1cc(C)c2[nH]c(=O)c(CN3CC(c4ccccn4)C3)cc2c1] | 498 | 7.62 |
| RU-0424498 | 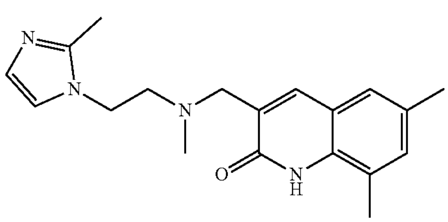 [SMILES: Cc1cc(C)c2[nH]c(=O)c(CN(C)CCn3ccnc3C)cc2c1] | 486 | 7.21 |
| RU-0424497 | 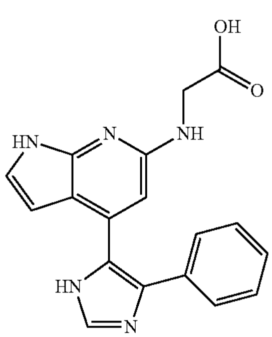 [SMILES: O=C(O)CNc1cc(-c2[nH]cnc2-c2ccccc2)c2cc[nH]c2n1] | 450 | 5.93 |

TABLE 6-continued

Structure-activity relationship analysis of chemical analogs (Refers to FIG. 1).

| Identifier | Compound Structure | RFU Score (10 µM) | % Activation |
|---|---|---|---|
| RU-0424496 | 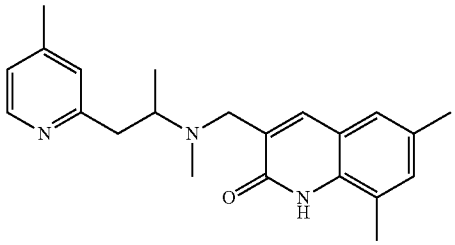 [SMILES: Cc1ccnc(CC(C)N(C)Cc2cc3cc(C)cc(C)c3[nH]c2=O)c1] | 516 | 8.27 |
| RU-0424495 | 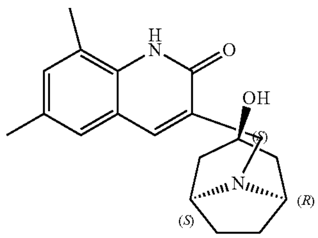 | 486 | 7.21 |
| RU-0424494 | 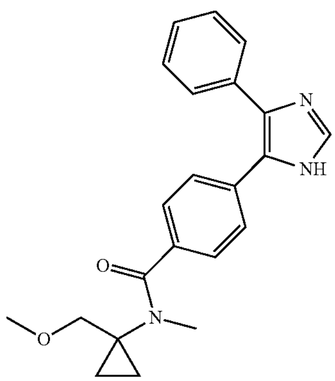 [SMILES: COCC1(N(C)C(=O)c2ccc(-c3[nH]cnc3-c3ccccc3)cc2)CC1] | 501 | 7.74 |
| RU-0424493 | 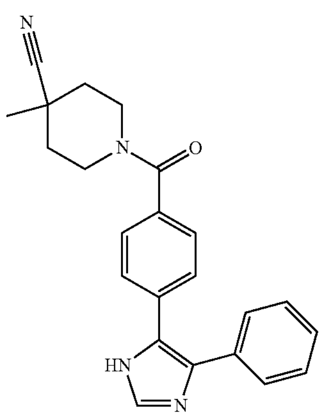 [SMILES: CC1(C#N)CCN(C(=O)c2ccc(-c3[nH]cnc3-c3ccccc3)cc2)CC1] | 551 | 9.53 |
| RU-0424492 | 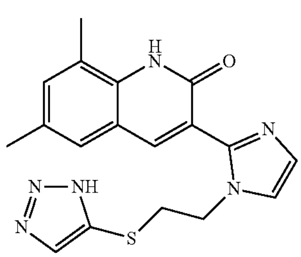 [SMILES: Cc1cc(C)c2[nH]c(=O)c(-c3nccn3CCSc3cnn[nH]3)cc2c1] | 455 | 6.11 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424491 | 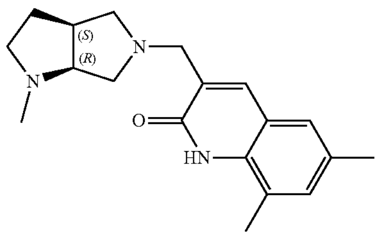 | 498 | 7.63 |
| RU-0424490 | 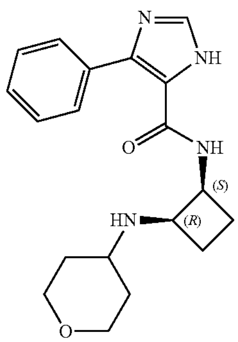 | 449 | 5.91 |
| RU-0424489 | 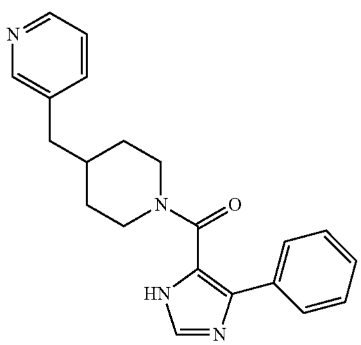 [SMILES: O=C(c1[nH]cnc1-c1ccccc1)N1CCC(Cc2cccnc2)CC1] | 551 | 9.48 |
| RU-0424488 | 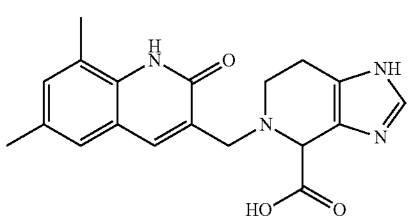 [SMILES: Cc1cc(C)c2[nH]c(=O)c(CN3CCc4[nH]cnc4C3C(=O)O)cc2c1] | 462 | 6.37 |
| RU-0424487 | 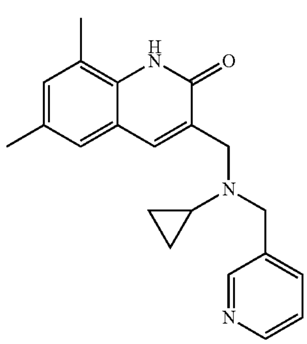 [SMILES: Cc1cc(C)c2[nH]c(=O)c(CN(Cc3cccnc3)C3CC3)cc2c1] | 501 | 7.72 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424486 | 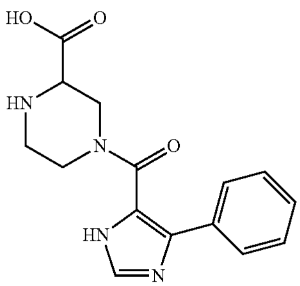 [SMILES: O=C(O)C1CN(C(=O)c2[nH]cnc2-c2ccccc2)CCN1] | 438 | 5.51 |
| RU-0424485 | 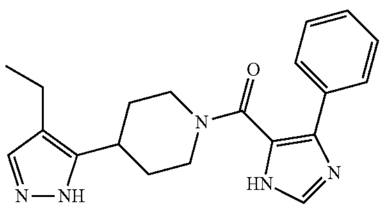 [SMILES: CCc1cn[nH]c1C1CCN(C(=O)c2[nH]cnc2-c2ccccc2)CC1] | 515 | 8.24 |
| RU-0424484 | 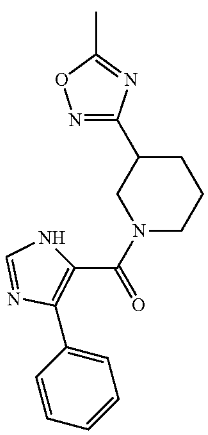 [SMILES: Cc1nc(C2CCCN(C(=O)c3[nH]cnc3-c3ccccc3)C2)no1] | 330 | 1.72 |
| RU-0424483 | 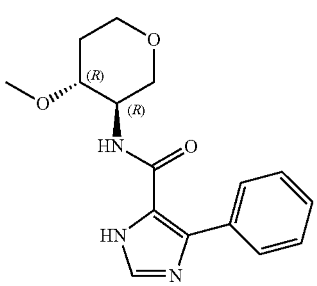 | 491 | 7.37 |

TABLE 6-continued
Structure-activity relationship analysis of chemical analogs (Refers to FIG. 1).
| Identifier | Compound Structure | RFU Score (10 µM) | % Activation |
|---|---|---|---|
| RU-0424482 | 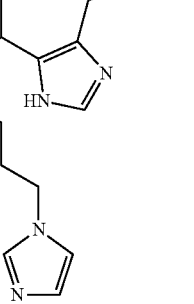 | 567 | 10.1 |
| RU-0424481 | 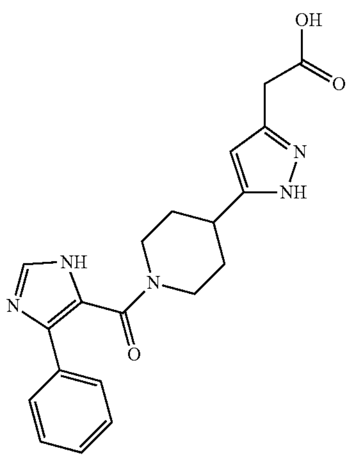 [SMILES: O=C(O)Cc1cc(C2CCN(C(=O)c3[nH]cnc3-c3ccccc3)CC2)[nH]n1] | 526 | 8.62 |
| RU-0424480 | 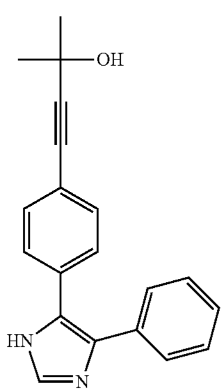 [SMILES: CC(C)(O)C#Cc1ccc(-c2[nH]cnc2-c2ccccc2)cc1] | 575 | 10.4 |
| RU-0424479 | 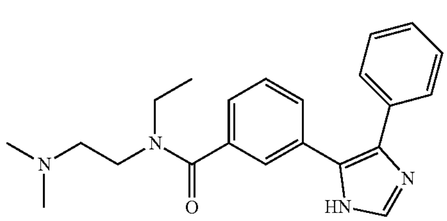 [SMILES: CCN(CCN(C)C)C(=O)c1cccc(-c2[nH]cnc2-c2ccccc2)c1] | 525 | 8.57 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424478 | 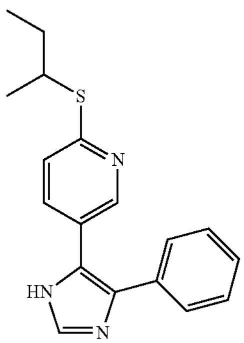 [SMILES: CCC(C)Sc1ccc(-c2[nH]cnc2-c2ccccc2)cn1] | 361 | 2.79 |
| RU-0424477 | 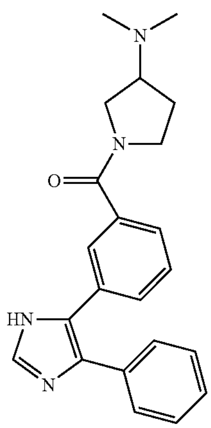 [SMILES: CN(C)C1CCN(C(=O)c2cccc(-c3[nH]cnc3-c3ccccc3)c2)C1] | 469 | 6.59 |
| RU-0424476 | 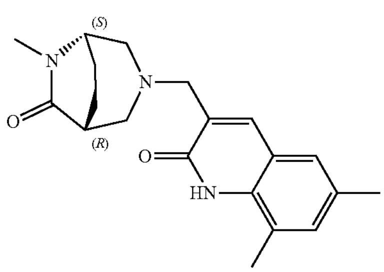 | 520 | 8.41 |
| RU-0424475 | 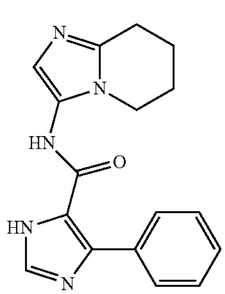 [SMILES: O=C(Nc1cnc2n1CCCC2)c1[nH]cnc1-c1ccccc1] | 491 | 6.39 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424474 | 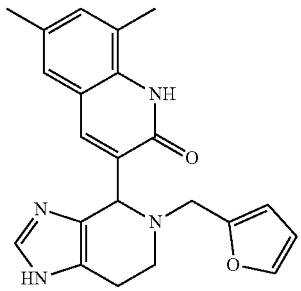 [SMILES: Cc1cc(C)c2[nH]c(=O)c(C3c4nc[nH]c4CCN3Cc3ccco3)cc2c1] | 566 | 10.0 |
| RU-0424473 | 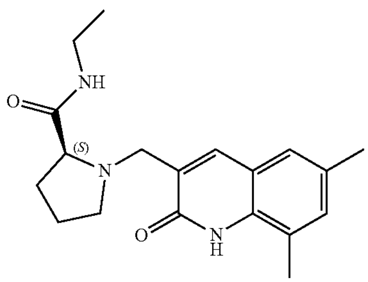 | 470 | 6.63 |
| RU-0424472 | 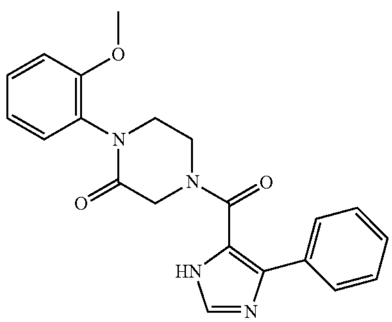 [SMILES: COc1ccccc1N1CCN(C(=O)c2[nH]cnc2-c2ccccc2)CC1=O] | 397 | 4.08 |
| RU-0424471 | 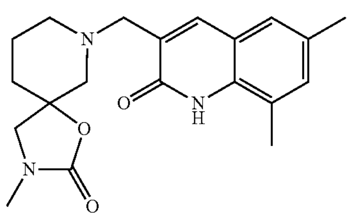 | 524 | 8.55 |
| RU-0424470 | 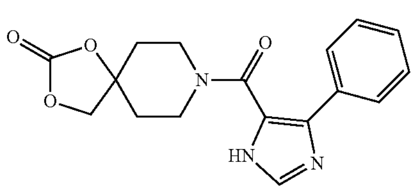 [SMILES: O=C1OCC2(CCN(C(=O)c3[nH]cnc3-c3ccccc3)CC2)O1] | 497 | 7.58 |
| RU-0424469 | 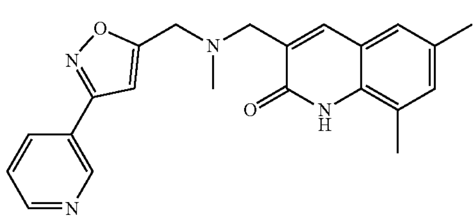 [SMILES: Cc1cc(C)c2[nH]c(=O)c(CN(C)Cc3cc(-c4cccnc4)no3)cc2c1] | 536 | 8.96 |

TABLE 6-continued

Structure-activity relationship analysis of chemical analogs (Refers to FIG. 1).

| Identifier | Compound Structure | RFU Score (10 µM) | % Activation |
|---|---|---|---|
| RU-0424468 | 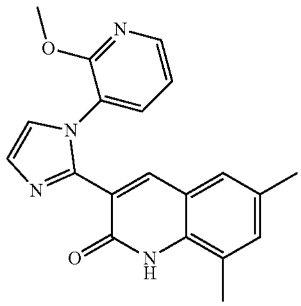 [SMILES: COc1ncccc1-n1ccnc1-c1cc2cc(C)cc(C)c2[nH]c1=O] | 508 | 7.97 |
| RU-0424467 | 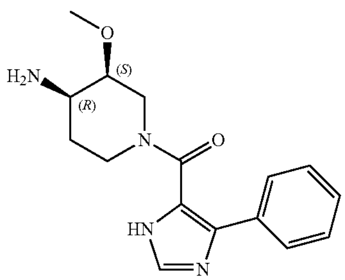 | 508 | 7.99 |
| RU-0424466 | 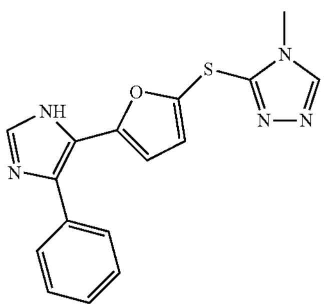 [SMILES: Cn1cnnc1Sc1ccc(-c2[nH]cnc2-c2ccccc2)o1] | 527 | 8.64 |
| RU-0424465 | 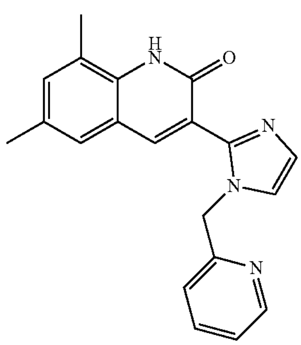 [SMILES: Cc1cc(C)c2[nH]c(=O)c(-c3nccn3Cc3ccccn3)cc2c1] | 427 | 5.14 |
| RU-0424464 | 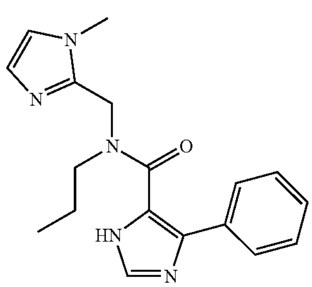 [SMILES: CCCN(Cc1nccn1C)C(=O)c1[nH]cnc1-c1ccccc1] | 330 | 1.72 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424463 | 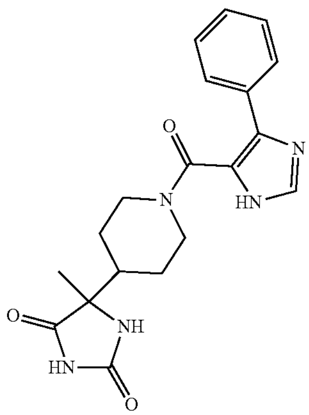 [SMILES: CC1(C2CCN(C(=O)c3[nH]cnc3-c3ccccc3)CC2)NC(=O)NC1=O] | 422 | 4.96 |
| RU-0424462 | 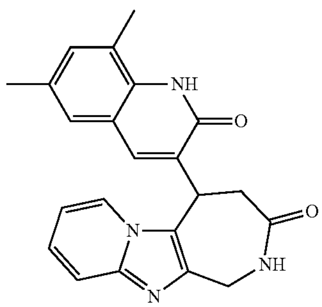 [SMILES: Cc1cc(C)c2[nH]c(=O)c(C3CC(=O)NCc4nc5ccccn5c43)cc2c1] | 503 | 7.81 |
| RU-0424461 | 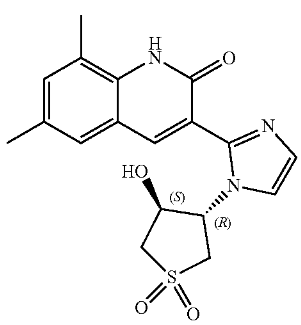 | 399 | 4.15 |
| RU-0424460 | 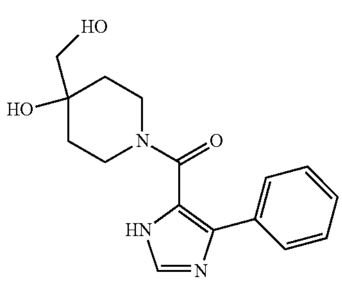 [SMILES: O=C(c1[nH]cnc1-c1ccccc1)N1CCC(O)(CO)CC1] | 429 | 5.19 |
| RU-0424459 | 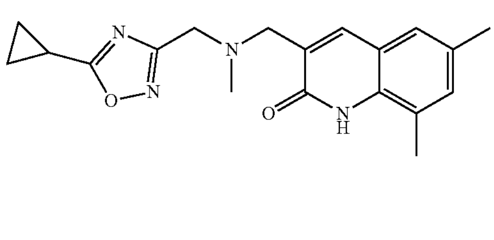 [SMILES: Cc1cc(C)c2[nH]c(=O)c(CN(C)Cc3noc(C4CC4)n3)cc2c1] | 383 | 3.58 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424458 | 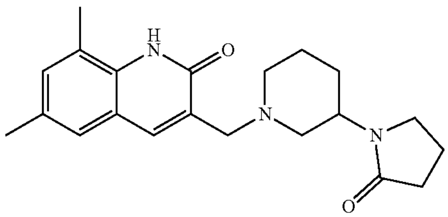 [SMILES: Cc1cc(C)c2[nH]c(=O)c(CN3CCCC(N4CCCC4=O)C3)cc2c1] | 306 | 0.87 |
| RU-0424457 | 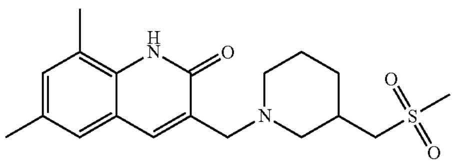 | 285 | 0.13 |
| RU-0424456 | 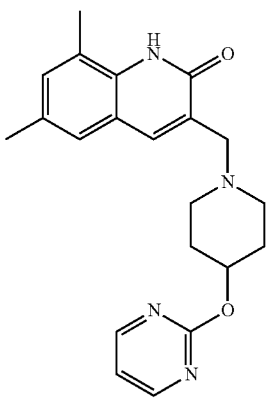 [SMILES: Cc1cc(C)c2[nH]c(=O)c(CN3CCC(Oc4ncccn4)CC3)cc2c1] | 310 | 0.99 |
| RU-0424455 | 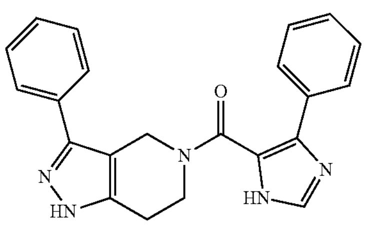 [SMILES: O=C(c1[nH]cnc1-c1ccccc1)N1CCc2[nH]nc(-c3ccccc3)c2C1] | 347 | 2.30 |
| RU-0424454 | 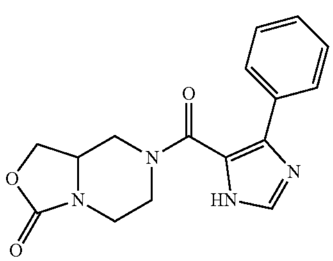 [SMILES: O=C(c1[nH]cnc1-c1ccccc1)N1CCN2C(=O)OCC2C1] | 333 | 1.83 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424453 | 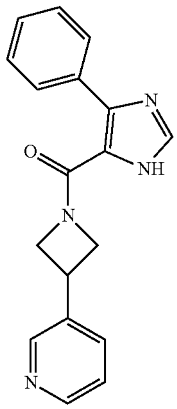 [SMILES: O=C(c1[nH]cnc1-c1ccccc1)N1CC(c2cccnc2)C1] | 323 | 1.46 |
| RU-0424452 | 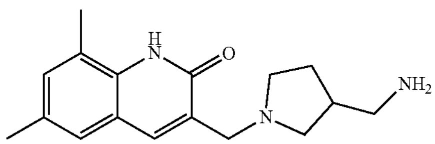 [SMILES: Cc1cc(C)c2[nH]c(=O)c(CN3CCC(CN)C3)cc2c1] | 328 | 1.65 |
| RU-0424451 | 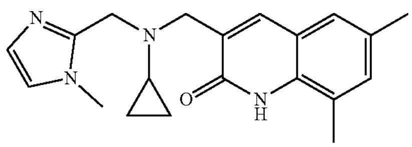 [SMILES: Cc1cc(C)c2[nH]c(=O)c(CN(Cc3nccn3C)C3CC3)cc2c1] | 305 | 0.82 |
| RU-0424450 | 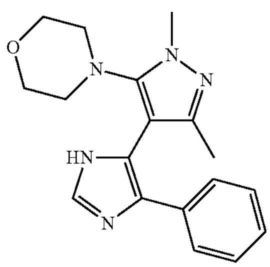 [SMILES: Cc1nn(C)c(N2CCOCC2)c1-c1[nH]cnc1-c1ccccc1] | 288 | 0.24 |
| RU-0424449 | 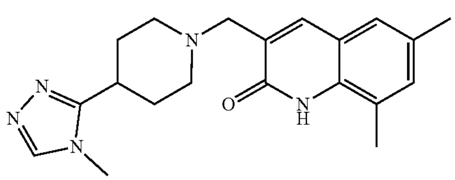 [SMILES: Cc1cc(C)c2[nH]c(=O)c(CN3CCC(c4nncn4C)CC3)cc2c1] | 284 | 0.10 |
| RU-0424448 | 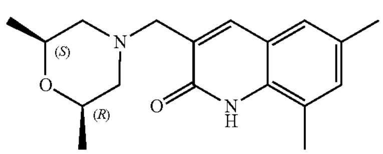 | 253 | −1.00 |
| RU-0424447 | 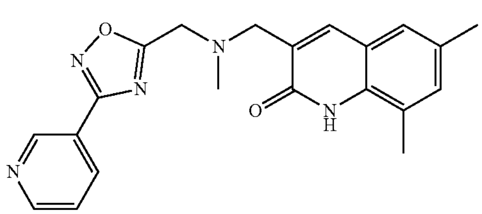 [SMILES: Cc1cc(C)c2[nH]c(=O)c(CN(C)Cc3nc(-c4cccnc4)no3)cc2c1] | 297 | 0.54 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0424446 | 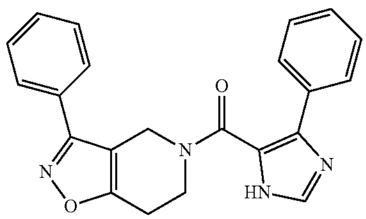 [SMILES: O=C(c1[nH]cnc1-c1ccccc1)N1CCc2onc(-c3ccccc3)c2C1] | 325 | 1.54 |
| RU-0424445 | 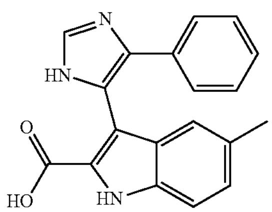 [SMILES: Cc1ccc2[nH]c(C(=O)O)c(-c3[nH]cnc3-c3ccccc3)c2c1] | 364 | 4.67 |
| RU-0424444 | 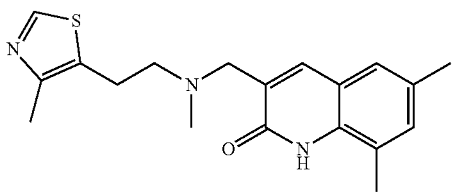 [SMILES: Cc1cc(C)c2[nH]c(=O)c(CN(C)CCc3scnc3C)cc2c1] | 446 | 5.79 |
| RU-0424443 | 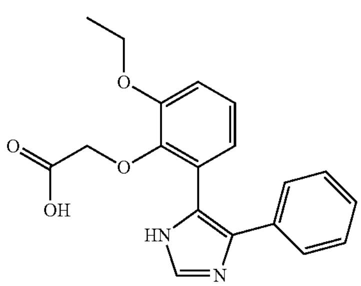 [SMILES: CCOc1cccc(-c2[nH]cnc2-c2ccccc2)c1OCC(=O)O] | 306 | 0.87 |
| RU-0424442 | 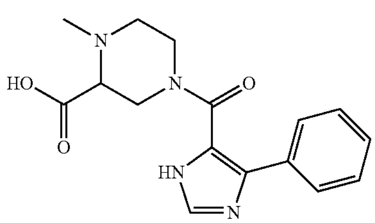 [SMILES: CN1CCN(C(=O)c2[nH]cnc2-c2ccccc2)CC1C(=O)O] | 287 | 0.18 |
| RU-0424441 | 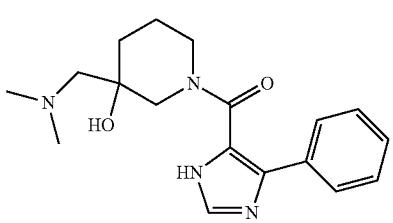 [SMILES: CN(C)CC1(O)CCCN(C(=O)c2[nH]cnc2-c2ccccc2)C1] | 368 | 3.04 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0268325 | 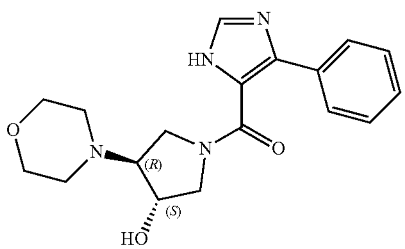 | 339 | 2.04 |
| RU-0267267 | 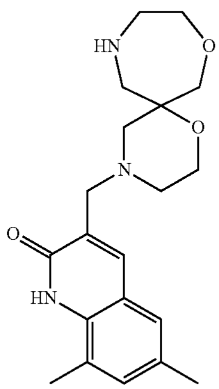 [SMILES: Cc1cc(C)c2[nH]c(=O)c(CN3CCOC4(CNCCOC4)C3)cc2c1] | 557 | 9.71 |
| RU-0265092 | 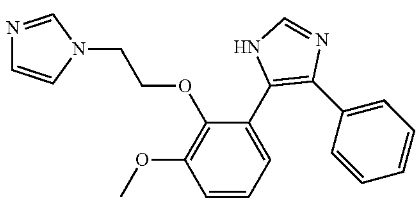 [SMILES: COc1cccc(-c2[nH]cnc2-c2ccccc2)c1OCCn1ccnc1] | 478 | 6.93 |
| RU-0264094 | 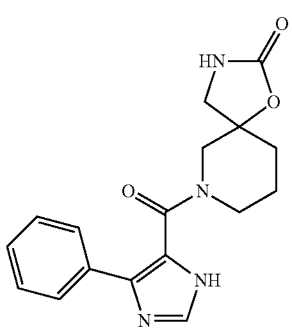 [SMILES: O=C1NCC2(CCCN(C(=O)c3[nH]cnc3-c3ccccc3)C2)O1] | 583 | 10.6 |
| RU-0262240 | 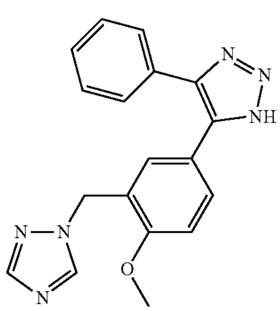 [SMILES: COc1ccc(-c2[nH]nnc2-c2ccccc2)cc1Cn1cncn1] | 496 | 7.55 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0261757 | 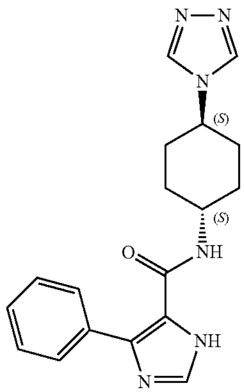 | 508 | 7.99 |
| RU-0261450 | 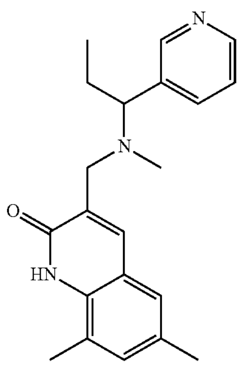 [SMILES: CCC(c1cccnc1)N(C)Cc1cc2cc(C)cc(C)c2[nH]c1=O] | 538 | 9.03 |
| RU-0261164 | 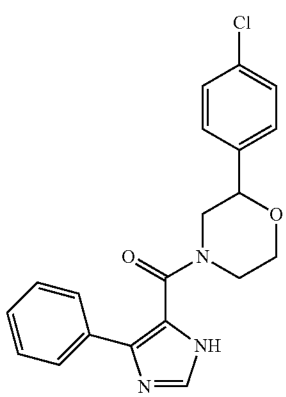 [SMILES: O=C(c1[nH]cnc1-c1ccccc1)N1CCOC(c2ccc(Cl)cc2)C1] | 544 | 9.24 |
| RU-0260066 | 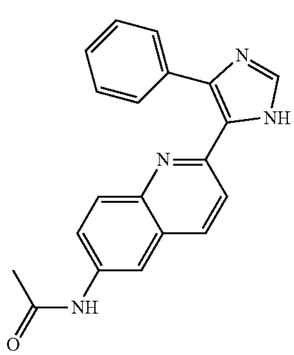 [SMILES: CC(=O)Nc1ccc2nc(-c3[nH]cnc3-c3ccccc3)ccc2c1] | 456 | 6.14 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0259020 | 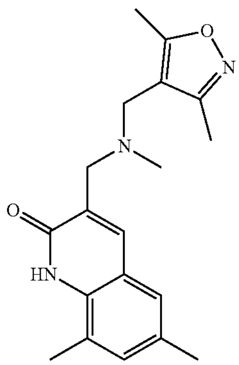 [SMILES: Cc1cc(C)c2[nH]c(=O)c(CN(C)Cc3c(C)noc3C)cc2c1] | 514 | 8.18 |
| RU-0253941 | 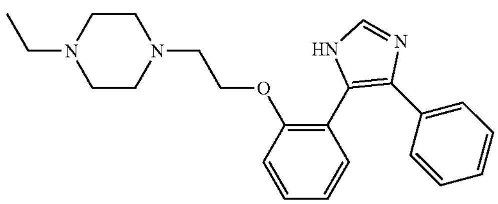 [SMILES: CCN1CCN(CCOc2ccccc2-c2[nH]cnc2-c2ccccc2)CC1] | 547 | 9.34 |
| RU-0253216 | 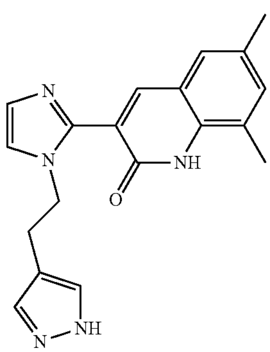 [SMILES: Cc1cc(C)c2[nH]c(=O)c(-c3nccn3CCc3cn[nH]c3)cc2c1] | 341 | 2.09 |
| RU-0253075 | 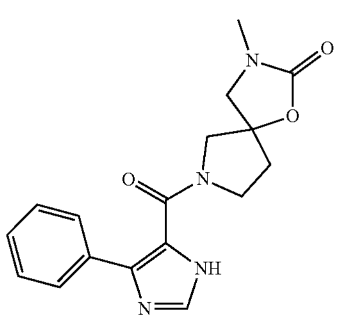 [SMILES: CN1CC2(CCN(C(=O)c3[nH]cnc3-c3ccccc3)C2)OC1=O] | 500 | 7.71 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0252250 | 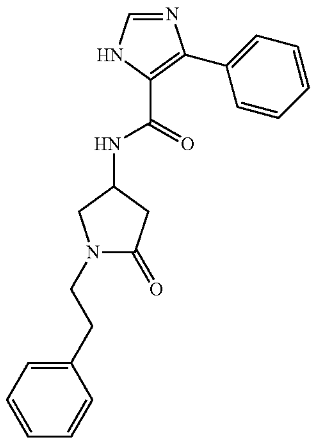 [SMILES: O=C(NC1CC(=O)N(CCc2ccccc2)C1)c1[nH]cnc1-c1ccccc1] | 533 | 8.85 |
| RU-0249817 | 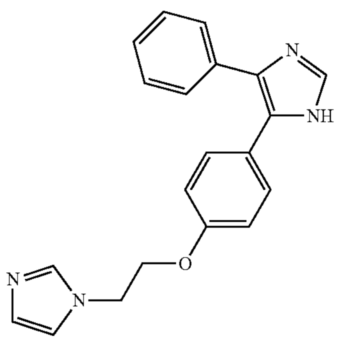 [SMILES: c1ccc(-c2nc[nH]c2-c2ccc(OCCn3ccnc3)cc2)cc1] | 561 | 9.84 |
| RU-0249023 | 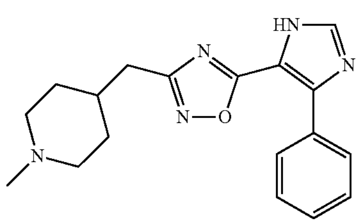 [SMILES: CN1CCC(Cc2noc(-c3[nH]cnc3-c3ccccc3)n2)CC1] | 293 | 0.40 |
| RU-0248967 | 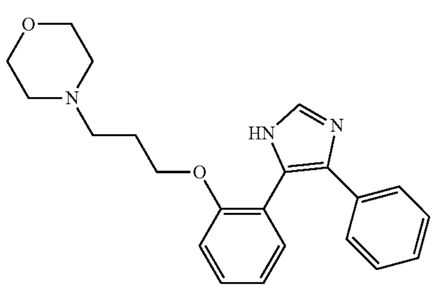 [SMILES: c1ccc(-c2nc[nH]c2-c2ccccc2OCCCN2CCOCC2)cc1] | 512 | 7.58 |

TABLE 6-continued

Structure-activity relationship analysis of chemical analogs (Refers to FIG. 1).

| Identifier | Compound Structure | RFU Score (10 μM) | % Activation |
|---|---|---|---|
| RU-0248829 | 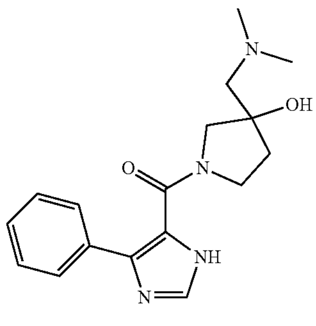 [SMILES: CN(C)CC1(O)CCN(C(=O)c2[nH]cnc2-c2ccccc2)C1] | 325 | 1.52 |
| RU-0248392 | 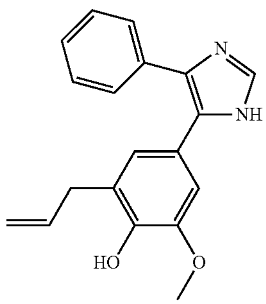 [SMILES: C=CCc1cc(-c2[nH]cnc2-c2ccccc2)cc(OC)c1O] | 423 | 4.98 |
| RU-0247047 | 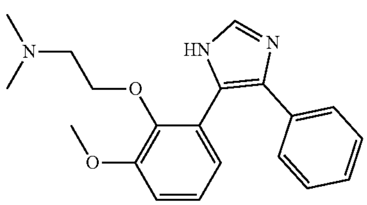 [SMILES: COc1cccc(-c2[nH]cnc2-c2ccccc2)c1OCCN(C)C] | 558 | 9.73 |
| RU-0245926 | 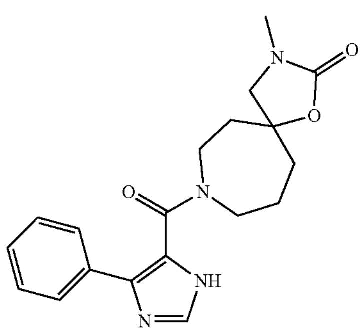 [SMILES: CN1CC2(CCCN(C(=O)c3[nH]cnc3-c3ccccc3)CC2)OC1=O] | 558 | 9.73 |
| RU-0239439 | 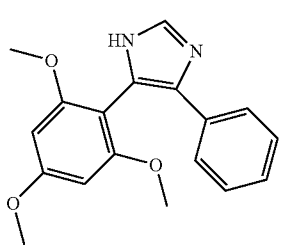 [SMILES: COc1cc(OC)c(-c2[nH]cnc2-c2ccccc2)c(OC)c1] | 472 | 6.72 |

TABLE 6-continued
Structure-activity relationship analysis of chemical analogs (Refers to FIG. 1).
| Identifier | Compound Structure | RFU Score (10 µM) | % Activation |
|---|---|---|---|
| RU-0238998 | 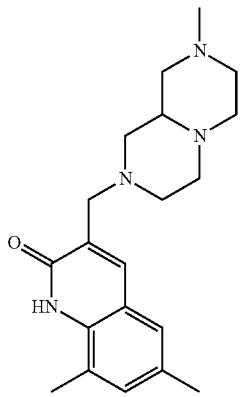 [SMILES: Cc1cc(C)c2[nH]c(=O)c(CN3CCN4CCN(C)CC4C3)cc2c1] | 469 | 6.62 |
| RU-0237450 | 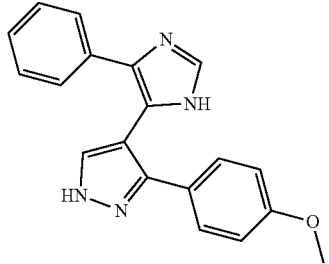 [SMILES: COc1ccc(-c2n[nH]cc2-c2[nH]cnc2-c2ccccc2)cc1] | 466 | 6.49 |
| RU-0237095 | 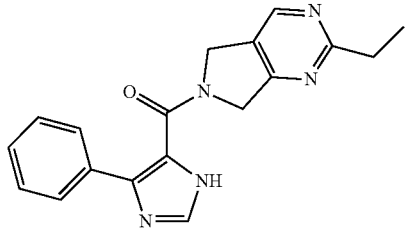 [SMILES: CCc1ncc2c(n1)CN(C(=O)c1[nH]cnc1-c1ccccc1)C2] | 453 | 6.04 |
| RU-0236307 | 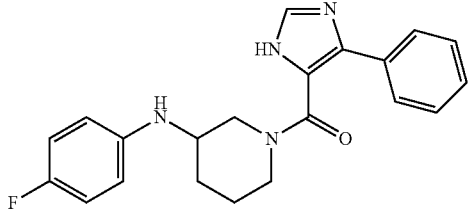 [SMILES: O=C(c1[nH]cnc1-c1ccccc1)N1CCCC(Nc2ccc(F)cc2)C1] | 473 | 6.76 |
| RU-0232369 | 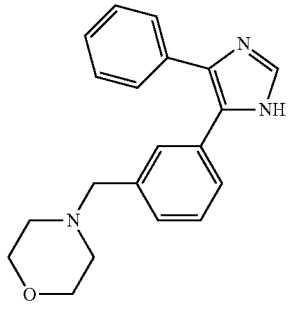 [SMILES: c1ccc(-c2nc[nH]c2-c2cccc(CN3CCOCC3)c2)cc1] | 294 | 0.43 |

TABLE 6-continued
Structure-activity relationship analysis of chemical analogs (Refers to FIG. 1).
| Identifier | Compound Structure | RFU Score (10 µM) | % Activation |
|---|---|---|---|
| RU-0231652 | 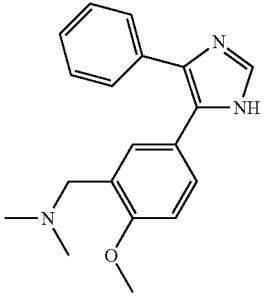 [SMILES: COc1ccc(-c2[nH]cnc2-c2ccccc2)cc1CN(C)C] | 299 | 0.62 |
| RU-0231240 | 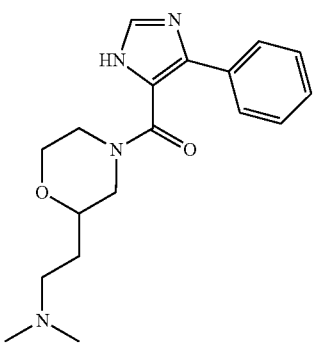 [SMILES: CN(C)CCC1CN(C(=O)c2[nH]cnc2-c2ccccc2)CCO1] | 596 | 11.1 |
| RU-0228904 | 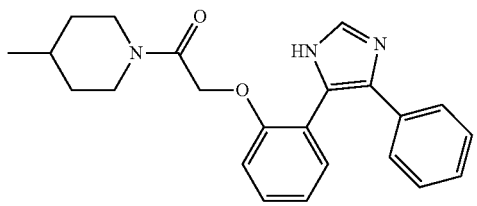 [SMILES: CC1CCN(C(=O)COc2ccccc2-c2[nH]cnc2-c2ccccc2)CC1] | 590 | 10.9 |
| RU-0228809 | 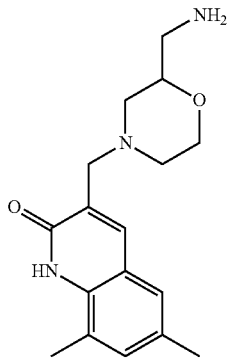 [SMILES: Cc1cc(C)c2[nH]c(=O)c(CN3CCOC(CN)C3)cc2c1] | 341 | 1.81 |
| RU-0227868 | 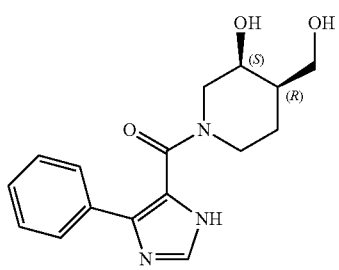 | 505 | 7.88 |

TABLE 6-continued
Structure-activity relationship analysis of chemical analogs (Refers to FIG. 1).
| Identifier | Compound Structure | RFU Score (10 μM) | % Activation |
|---|---|---|---|
| RU-0227648 | 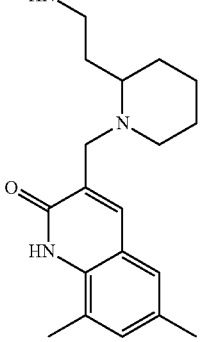 | 494 | 7.48 |
| RU-0227345 | 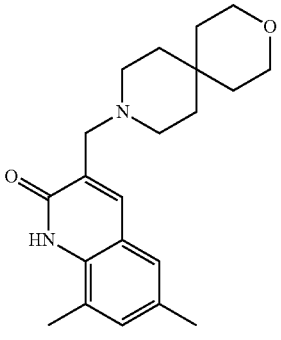 [SMILES: Cc1cc(C)c2[nH]c(=O)c(CN3CCC4(CCOCC4)CC3)cc2c1] | 384 | 3.6 |
| RU-0227342 | 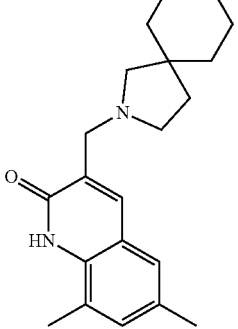 | 591 | 11.0 |
| RU-0222072 | 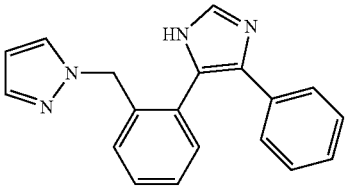 [SMILES: c1ccc(-c2nc[nH]c2-c2ccccc2Cn2cccn2)cc1] | 425 | 5.05 |

Although the present disclosure has been described with respect to one or more particular embodiments and/or examples, it will be understood that other embodiments and/or examples of the present disclosure may be made without departing from the scope of the present disclosure.

REFERENCE

Ando et al., (2017). Dev Cell 43, 643-650 e643.
Beederman et al., (2013). J Biomed Sci Eng 6, 32-52.
Bosnakovski et al., (2014). Skelet Muscle 4, 4.
Cabrera et al., (2012). J Biol Chem 287, 22759-22770.
Carragee et al., (2011). Spine J 11, 471-491.
Chen et al., (2012). Int J Biol Sci 8, 272-288.
Chen et al., (2004). J Am Chem Soc 126, 410-411.
Cosman et al., (2016). N Engl J Med 375, 1532-1543.
Drieling et al., (2016). Menopause 23, 1168-1175.
Fu et al., (2013). Ann Intern Med 158, 890-902.
Fux et al., (2004). Nucleic Acids Res 32, e1.
Greenblatt et al., (2015). J Biol Chem 290, 284-295.
Greenblatt et al. (2010). J Clin Invest 120, 2457-2473.
Huang, et al., (2007). Tissue Eng 13, 2311-2320.
Huycke, et al., (2012). Development 139, 2371-2380.
Inohaya et al., (2007). Dev Dyn 236, 3031-3046.
Jaiswal, et al., (1997). J Cell Biochem 64, 295-312.
Katagiri, et al., (1994). J Cell Biol 127, 1755-1766.
Kim, et al., (2013). Ther Adv Musculoskelet Dis 5, 13-31.
Laue, et al., (2008). Development 135, 3775-3787.
Lin, et al., (2011). J Cell Biochem 112, 3491-3501.
Livak, et al., (2001). Method. Methods 25, 402-408.
Lloyd, et al., (2017). Proc Natl Acad Sci USA 114, 8722-8727.
Ma, et al., (2017). Sci Rep 7, 43399.
Malo et al., (2006). Nat Biotechnol 24, 167-175.
Matsuguchi et al., (2009). J Bone Miner Res 24, 398-410.
Moorwood, et al., (2011). PLoS One 6, e26169.
Mullard, et al. (2016). Nat Rev Drug Discov 15, 669.
Rey et al., (2007). Bone 41, 59-67.
Rodda, et al., (2006). Development 133, 3231-3244.
Rutkovskiy, et al., (2016). Med Sci Monit Basic Res 22, 95-106.
Saita, et al., (2015). Ther Adv Chronic Dis 6, 185-193.
Thouverey, et al., (2015). Bonekey Rep 4, 711.
Vaccaro, et al., (2008). Spine J 8, 457-465.
Yadav et al., (2012). BRITER: PLoS One 7, e37134

What is claimed is:

1. A method for preventing or treating a bone disorder in a subject in need thereof comprising administering to the subject an effective amount of a compound to prevent or treat the bone disorder, said compound having the structure:

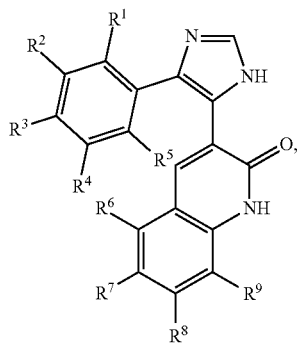

wherein $R^1$, $R^2$, $R^3$, $R^4$, $R^5$, $R^6$, $R^7$, $R^8$, and $R^9$ are individually —H, a methyl group, an ethyl group, a propyl group, an isopropyl group, an isobutyl group, a tert-butyl group, a neo-pentyl group, or an isopentyl group, and the bone disorder is osteoporosis, fracture, osteogenesis imperfecta, periodontal disease, or osteoarthritis.

2. The method of claim 1, wherein the compound has the structure:

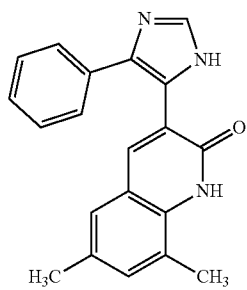 [SMILES: Cc1cc(C)c2[nH]c(=O)c(-c3[nH]cnc3-c3ccccc3)cc2c1]

(6,8-dimethyl-3-(4-phenyl-1H-imidazol-5-yl)quinolin-2 (1H)-one (DIPQUO)).

3. The method of claim 2, wherein the effective amount of DIPQUO is administered in conjunction with a cancer therapy.

4. The method of claim 3, wherein the cancer therapy is chemotherapy and/or radiation therapy.

5. A pharmaceutical composition comprising one or more compounds having the structure:

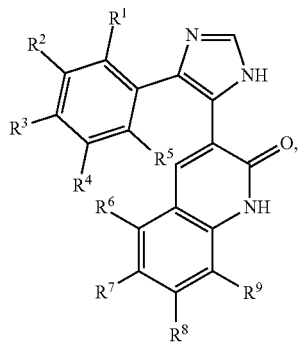

wherein $R'$, $R^2$, $R^3$, $R^4$, $R^5$, $R^6$, $R^7$, $R^8$, and $R^9$ are independently —H, a methyl group, an ethyl group, a propyl group, an isopropyl group, an isobutyl group, a tert-butyl group, a neo-pentyl group, or an isopentyl group, in a pharmaceutical carrier.

6. A pharmaceutical composition consisting essentially of:

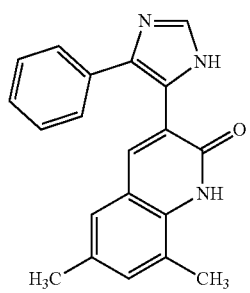 [SMILES: Cc1cc(C)c2[nH]c(=O)c(-c3[nH]cnc3-c3ccccc3)cc2c1]

(6,8-dimethyl-3-(4-phenyl-1H-imidazol-5-yl)quinolin-2 (1H)-one) in a pharmaceutical carrier.

7. The pharmaceutical composition of claim 5, wherein the composition does not contain an inhibitor of p38 MAPK.

8. The pharmaceutical composition of claim 6, wherein the composition does not contain an inhibitor of p38 MAPK.

* * * * *

SEQUENCE LISTING

<160> NUMBER OF SEQ ID NOS: 18

<210> SEQ ID NO 1
<211> LENGTH: 18
<212> TYPE: DNA
<213> ORGANISM: Artificial Sequence
<220> FEATURE:
<223> OTHER INFORMATION: mouse primer

<400> SEQUENCE: 1
cggccctccc tgaactct                                             18

<210> SEQ ID NO 2
<211> LENGTH: 19
<212> TYPE: DNA
<213> ORGANISM: Artificial Sequence
<220> FEATURE:
<223> OTHER INFORMATION: mouse primer

<400> SEQUENCE: 2
tgcctgcctg ggatctgta                                            19

<210> SEQ ID NO 3
<211> LENGTH: 18
<212> TYPE: DNA
<213> ORGANISM: Artificial Sequence
<220> FEATURE:
<223> OTHER INFORMATION: mouse primer

<400> SEQUENCE: 3
gcccctacca ccagtacg                                             18

<210> SEQ ID NO 4
<211> LENGTH: 19
<212> TYPE: DNA
<213> ORGANISM: Artificial Sequence
<220> FEATURE:
<223> OTHER INFORMATION: mouse primer

<400> SEQUENCE: 4
tcaccatcct cacctctgg                                            19

```
<210> SEQ ID NO 5
<211> LENGTH: 21
<212> TYPE: DNA
<213> ORGANISM: Artificial Sequence
<220> FEATURE:
<223> OTHER INFORMATION: mouse primer

<400> SEQUENCE: 5
agcgaccact tgagcaaaca t                                              21

<210> SEQ ID NO 6
<211> LENGTH: 20
<212> TYPE: DNA
<213> ORGANISM: Artificial Sequence
<220> FEATURE:
<223> OTHER INFORMATION: mouse primer

<400> SEQUENCE: 6
gcggctgatt ggcttcttct                                                20

<210> SEQ ID NO 7
<211> LENGTH: 20
<212> TYPE: DNA
<213> ORGANISM: Artificial Sequence
<220> FEATURE:
<223> OTHER INFORMATION: mouse primer

<400> SEQUENCE: 7
aacccagaca caagcattcc                                                20

<210> SEQ ID NO 8
<211> LENGTH: 20
<212> TYPE: DNA
<213> ORGANISM: Artificial Sequence
<220> FEATURE:
<223> OTHER INFORMATION: mouse primer

<400> SEQUENCE: 8
gagacatttt cccgttcacc                                                20

<210> SEQ ID NO 9
<211> LENGTH: 20
<212> TYPE: DNA
<213> ORGANISM: Artificial Sequence
<220> FEATURE:
<223> OTHER INFORMATION: mouse primer

<400> SEQUENCE: 9
gcagcttggt gcacacctag                                                20

<210> SEQ ID NO 10
<211> LENGTH: 22
<212> TYPE: DNA
<213> ORGANISM: Artificial Sequence
<220> FEATURE:
<223> OTHER INFORMATION: mouse primer

<400> SEQUENCE: 10
ggagctgctg tgacatccat ac                                             22

<210> SEQ ID NO 11
<211> LENGTH: 21
<212> TYPE: DNA
<213> ORGANISM: Artificial Sequence
<220> FEATURE:
```

<223> OTHER INFORMATION: mouse primer

<400> SEQUENCE: 11
tctgaaccga gccctgacat c                                              21

<210> SEQ ID NO 12
<211> LENGTH: 21
<212> TYPE: DNA
<213> ORGANISM: Artificial Sequence
<220> FEATURE:
<223> OTHER INFORMATION: mouse primer

<400> SEQUENCE: 12
agcagtagcg gccatgtgaa g                                              21

<210> SEQ ID NO 13
<211> LENGTH: 22
<212> TYPE: DNA
<213> ORGANISM: Artificial Sequence
<220> FEATURE:
<223> OTHER INFORMATION: mouse primer

<400> SEQUENCE: 13
aggcattgac tctgaagatg ct                                             22

<210> SEQ ID NO 14
<211> LENGTH: 20
<212> TYPE: DNA
<213> ORGANISM: Artificial Sequence
<220> FEATURE:
<223> OTHER INFORMATION: mouse primer

<400> SEQUENCE: 14
tccccacagg aatctctctg                                                20

<210> SEQ ID NO 15
<211> LENGTH: 22
<212> TYPE: DNA
<213> ORGANISM: Artificial Sequence
<220> FEATURE:
<223> OTHER INFORMATION: mouse primer

<400> SEQUENCE: 15
gcggacattg tcatccagtt tg                                             22

<210> SEQ ID NO 16
<211> LENGTH: 19
<212> TYPE: DNA
<213> ORGANISM: Artificial Sequence
<220> FEATURE:
<223> OTHER INFORMATION: mouse primer

<400> SEQUENCE: 16
cgtcgtcgaa atgggcatc                                                 19

<210> SEQ ID NO 17
<211> LENGTH: 21
<212> TYPE: DNA
<213> ORGANISM: Artificial Sequence
<220> FEATURE:
<223> OTHER INFORMATION: mouse primer

<400> SEQUENCE: 17
ctaacatcaa atggggtgag g                                              21

```
<210> SEQ ID NO 18
<211> LENGTH: 20
<212> TYPE: DNA
<213> ORGANISM: Artificial Sequence
<220> FEATURE:
<223> OTHER INFORMATION: mouse primer

<400> SEQUENCE: 18
cggagatgat gacccttttg                                           20
```